United States Patent
Weitekamp et al.

(10) Patent No.: US 10,799,613 B2
(45) Date of Patent: Oct. 13, 2020

(54) DIRECT PHOTOPATTERNING OF ROBUST AND DIVERSE MATERIALS

(71) Applicant: CALIFORNIA INSTITUTE OF TECHNOLOGY, Pasadena, CA (US)

(72) Inventors: Raymond Weitekamp, Glendale, CA (US); Robert H. Grubbs, South Pasadena, CA (US); Harry A. Atwater, South Pasadena, CA (US); James Fakonas, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 383 days.

(21) Appl. No.: 14/505,824

(22) Filed: Oct. 3, 2014

(65) Prior Publication Data

US 2015/0118188 A1  Apr. 30, 2015

Related U.S. Application Data

(60) Provisional application No. 61/897,304, filed on Oct. 30, 2013, provisional application No. 61/945,639, filed on Feb. 27, 2014, provisional application No. 62/032,343, filed on Aug. 1, 2014.

(51) Int. Cl.

| | |
|---|---|
| *C09K 11/00* | (2006.01) |
| *A61L 27/16* | (2006.01) |
| *C08G 61/08* | (2006.01) |
| *C08L 65/00* | (2006.01) |
| *A61L 27/50* | (2006.01) |
| *G03F 7/029* | (2006.01) |
| *G03F 7/004* | (2006.01) |
| *C07F 15/00* | (2006.01) |
| *C08F 232/08* | (2006.01) |

(52) U.S. Cl.
CPC .............. *A61L 27/16* (2013.01); *A61L 27/50* (2013.01); *C08G 61/08* (2013.01); *C08L 65/00* (2013.01); *G03F 7/0042* (2013.01); *G03F 7/029* (2013.01); *C08F 232/08* (2013.01); *C08G 2261/1426* (2013.01); *C08G 2261/1432* (2013.01); *C08G 2261/3325* (2013.01); *C08G 2261/3342* (2013.01); *C08G 2261/90* (2013.01); *C08G 2261/94* (2013.01)

(58) Field of Classification Search
CPC ........................... C09K 11/07; C07F 15/0046
USPC ............. 252/501.1, 182.13; 502/155; 546/10
See application file for complete search history.

(56) References Cited

U.S. PATENT DOCUMENTS

| | | | |
|---|---|---|---|
| 2,726,229 A * | 12/1955 | Padbury | C08F 220/12 526/261 |
| 5,191,026 A | 3/1993 | Nishi et al. | |
| 5,312,940 A | 5/1994 | Grubbs et al. | |
| 5,342,909 A | 8/1994 | Grubbs et al. | |
| 5,571,471 A | 11/1996 | Hull | |
| 5,750,815 A | 5/1998 | Grubbs et al. | |
| 5,831,108 A | 11/1998 | Grubbs et al. | |
| 5,917,071 A | 6/1999 | Grubbs et al. | |
| 5,969,170 A | 10/1999 | Grubbs et al. | |
| 5,977,393 A | 11/1999 | Grubbs et al. | |
| 6,008,298 A | 12/1999 | Hatke et al. | |
| 6,048,993 A | 4/2000 | Grubbs et al. | |
| 6,077,805 A | 6/2000 | Van et al. | |
| 6,111,121 A | 8/2000 | Grubbs et al. | |
| 6,114,082 A | 9/2000 | Hakey et al. | |
| 6,153,778 A | 11/2000 | Grubbs et al. | |
| 6,190,829 B1 | 2/2001 | Holmes et al. | |
| 6,211,391 B1 | 4/2001 | Grubbs et al. | |
| 6,284,852 B1 | 9/2001 | Lynn et al. | |
| 6,313,332 B1 | 11/2001 | Grubbs et al. | |
| 6,391,436 B1 | 5/2002 | Xu et al. | |
| 6,426,419 B1 | 7/2002 | Grubbs et al. | |
| 6,486,279 B2 | 11/2002 | Lynn et al. | |
| 6,504,041 B2 | 1/2003 | Grubbs et al. | |
| 6,514,666 B1 | 2/2003 | Choi et al. | |
| 6,515,084 B2 | 2/2003 | Grubbs et al. | |
| 6,552,139 B1 | 4/2003 | Herrmann et al. | |
| 6,624,265 B2 | 9/2003 | Grubbs et al. | |

(Continued)

FOREIGN PATENT DOCUMENTS

| | | |
|---|---|---|
| EP | 2903996 | 8/2015 |
| JP | 2001-278959 A | 10/2001 |

(Continued)

OTHER PUBLICATIONS

International Patent Application No. PCT/US2014/059028: International Search Report and the Written Opinion dated Jan. 14, 2015, 15 pages.

Louie et al, "Metathesis of Electron-Rich Olefins: Structure and Reactivity of Electron-Rich Carbene Complexes", Organometallics, 2002, 21(11), 2153-2164, Published online: Apr. 25, 2002.

Love et al, "A practical and Highly Active Ruthenium-Based Catalyst That Effects the Cross Metathesis of Acrylonitrile", Angew., 504, Chem., Int. Ed., Nov. 2002, 41(21), 4035-4037.

Miyake et al, "Precisely Tunable Photonic Crystals From Rapidly Self-Assembling Brush Block Copolymer Blends", Angewandte Chemie International Edition, 2012, 51, 11246-11248.

(Continued)

*Primary Examiner* — Charanjit Aulakh
(74) *Attorney, Agent, or Firm* — BakerHostetler

(57) ABSTRACT

The present invention relates to methods of metathesizing olefins using catalysts previously considered to be practically inactive. The present invention further relates to novel photosensitive compositions, their use as photoresists, and methods related to patterning polymer layers on substrates. Further, modifications to the compositions and method provide for an unprecedented functionalization of the compositions, useful for example in the preparation of sensors, drug delivery systems, and tissue scaffolds. The novel compositions and associated methods also provide for the opportunity to prepare 3-dimensional objects which provide new access to critically dimensioned devices, including for example photonic devices.

58 Claims, 8 Drawing Sheets

(56) References Cited

U.S. PATENT DOCUMENTS

| | | | |
|---|---|---|---|
| 6,635,768 B1 | 10/2003 | Herrmann et al. | |
| 6,759,537 B2 | 7/2004 | Grubbs et al. | |
| 6,767,828 B2 * | 7/2004 | Andry | H01L 21/288 257/E21.009 |
| 6,787,620 B2 | 9/2004 | Herrmann et al. | |
| 6,806,325 B2 | 10/2004 | Grubbs et al. | |
| 6,818,586 B2 | 11/2004 | Grubbs et al. | |
| 7,102,047 B2 | 9/2006 | Grubbs et al. | |
| 7,288,666 B2 | 10/2007 | Grubbs et al. | |
| 7,294,717 B2 | 11/2007 | Herrmann et al. | |
| 7,329,758 B1 | 2/2008 | Grubbs et al. | |
| 7,378,528 B2 | 5/2008 | Herrmann et al. | |
| 7,557,051 B2 * | 7/2009 | Ryu | B29C 33/424 264/328.16 |
| 7,652,145 B2 | 1/2010 | Herrmann et al. | |
| 7,750,172 B2 | 7/2010 | Grubbs et al. | |
| 8,771,927 B2 | 7/2014 | Tang | |
| 2001/0039360 A1 | 11/2001 | Grubbs et al. | |
| 2002/0013473 A1 | 1/2002 | Grubbs et al. | |
| 2002/0022733 A1 | 2/2002 | Grubbs et al. | |
| 2002/0055598 A1 | 5/2002 | Lynn et al. | |
| 2002/0177710 A1 | 11/2002 | Grubbs et al. | |
| 2003/0069374 A1 | 4/2003 | Grubbs et al. | |
| 2003/0181609 A1 | 9/2003 | Grubbs et al. | |
| 2005/0113590 A1 | 5/2005 | Grubbs et al. | |
| 2006/0011470 A1 | 3/2006 | Showa | |
| 2006/0241317 A1 | 10/2006 | Grubbs et al. | |
| 2008/0118874 A1 | 5/2008 | Robinson et al. | |
| 2008/0261150 A1 | 10/2008 | Tsubaki et al. | |
| 2009/0012248 A1 | 1/2009 | Grubbs et al. | |
| 2009/0012254 A1 | 1/2009 | Grubbs et al. | |
| 2009/0054597 A1 | 2/2009 | Ong et al. | |
| 2011/0003905 A1 | 1/2011 | Guciimeiser et al. | |
| 2011/0124868 A1 | 5/2011 | Grubbs et al. | |
| 2012/0251953 A1 | 10/2012 | Robinson et al. | |
| 2012/0329954 A1 | 12/2012 | Ong et al. | |
| 2013/0096314 A1 | 4/2013 | Kunz et al. | |
| 2013/0129988 A1 | 5/2013 | Yasuda et al. | |
| 2013/0296491 A1 | 11/2013 | Xia et al. | |
| 2013/0324666 A1 | 12/2013 | Xia et al. | |
| 2014/0011958 A1 | 1/2014 | Miyake et al. | |
| 2014/0099573 A1 | 4/2014 | Weitekamp et al. | |
| 2014/0255849 A1 | 9/2014 | Robinson et al. | |
| 2015/0118188 A1 | 4/2015 | Weitekamp et al. | |
| 2015/0126683 A1 | 5/2015 | Obrecht et al. | |
| 2015/0166686 A1 | 6/2015 | Liu et al. | |
| 2015/0249222 A1 | 9/2015 | Szigethy et al. | |

FOREIGN PATENT DOCUMENTS

| | | |
|---|---|---|
| JP | 2008-096880 A | 4/2008 |
| WO | 20091097955 A1 | 8/2009 |
| WO | 20141055720 A1 | 4/2014 |

OTHER PUBLICATIONS

Miyake et al, "Synthesis of Isocyanate-Based Brush Block Copolymers and Their Rapid Self-Assembly to Infrared-Reflecting Photonic Crystals", J. Amer. Chem. Soc., 2012, 134, 14249-14254.

Piunova et al, "Highly Ordered Dielectric Mirrors via the Self-Assembly of Dendronized Block Copolymers", J. Amer. Chem. Soc., 2013, 135(41), 15609-15616.

Sveinbjornsson et al, "Rapid Self-Assembly of Brush Block Copolymers to Photonic Crystals", PNAS, 2012, 109, 14332-14336.

Vldavsky, et al., "Light-Induced Olefin Metathesis", Beilstein Journal of Organic Chemistry, 2010, 6, 1106-1119.

Wang et al, "Cationic Ruii Complexes with N-Heterocyclic Carbene Ligands for UV-Induced Ring-Opening Metathesis Polymerization". Angewandte Chemie International Edition, 2008, 47(17), 3267-3270.

Hone, etal., Poly(thienylvinylene); Polymer 51 (2010) 1541-1547.

Khalimon et al., Photogeneration of a Phosphomium Alkylidene Olefin Metethesis Catalyst, Organometallics, 2012, 5634-5637.

P.F. Jacobs; The University of Texas at Austin, Fundamentals of Stereolithography, 1992, pp. 196-211.

Weitekamp, Raymond, et al., "Photolithographic olefin metathesis polymerization," Journal of the American Chemical Society, 2013, vol. 135, No. 45, pp. 16817-16820.

* cited by examiner

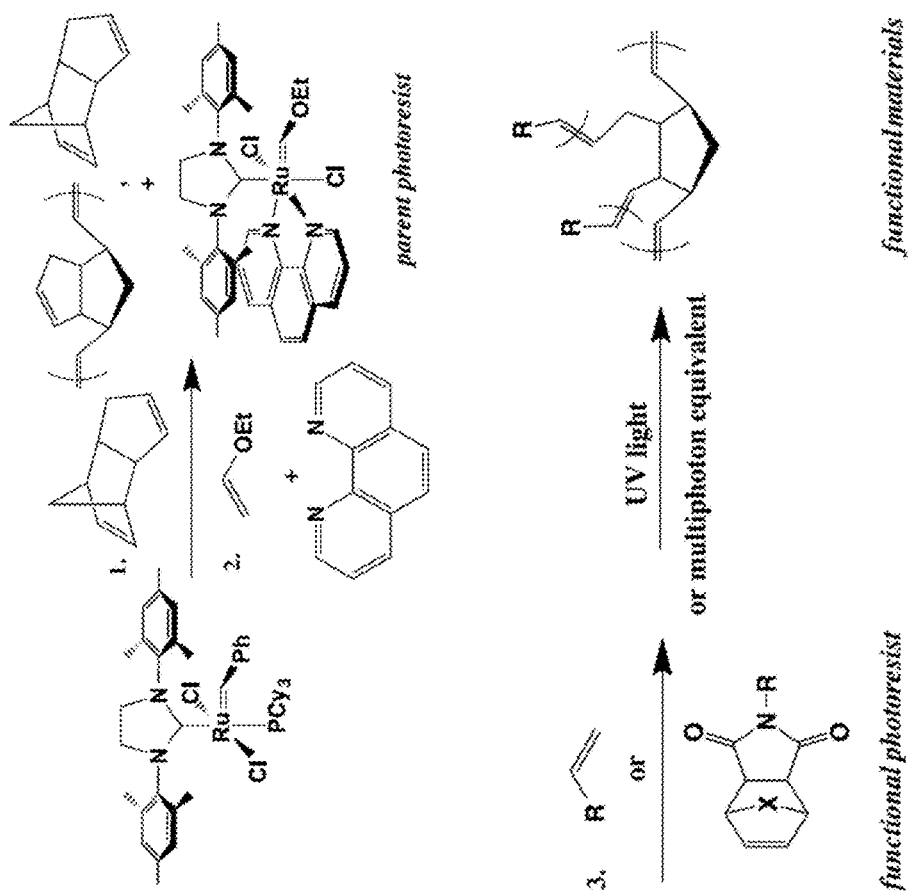

DIRECT PHOTOPATTERNING OF ROBUST AND DIVERSE MATERIALS

CROSS REFERENCE TO RELATED APPLICATIONS

This application claims the benefit of priority to U.S. Patent Application Ser. No. 61/897,304, filed Oct. 30, 2013, U.S. Patent Application Ser. No. 61/945,639, filed Feb. 27, 2014, and U.S. Patent Application Ser. No. 62/032,343, filed Aug. 1, 2014, the contents of which are each incorporated by reference in their entirety for any and all purposes.

GOVERNMENT RIGHTS

This invention was made with government support under Grant No. DE-SC0001293 awarded by the U.S. Department of Energy and under Grant No. N00014-13-0895 awarded by the U.S. Office of Naval Research. The government has certain rights in the invention.

TECHNICAL FIELD

The present invention relates to functionalized photolithographic compositions. It also relates to metathesis reactions catalyzed by organometallic coordination compounds, particularly by Fischer-type ruthenium carbene catalysts.

BACKGROUND

Photolithography is the patterning technique at the foundation of microfabrication, the core of modern integrated circuit technology. In a photoresist, the pattern of optical irradiation is converted to a pattern of chemically distinct regions, typically through photoinitiated functional group cleavage or crosslinking. Many modern photoresists employ the concept of "chemical amplification," in which a photogenerated catalyst reacts with many sites. For example, photoacid generators are commonly employed in chemically amplified resists, either to catalyze a ring opening polymerization or initiate a cascade of deprotective bond scissions within a polymer matrix, imparting new solubility properties to the irradiated regions. While there are a number of light-mediated reactions that could be, in principle, employed in photolithography, very few have been implemented. Despite the fact that there are hundreds of commercially available photoresists, the functional diversity amongst these materials is severely limited. In most applications, the photoresist serves the sole purpose of a sacrificial mask or mold; very rarely is the resist material incorporated as a structural element or chemically functional interface. The ability to generate new kinds of chemically functional materials directly via photolithography would enable a host of new applications, for example in microelectromechanical systems (MEMS), microfluidics, patterned biomaterials and artificial optical materials. Olefin metathesis is a robust synthetic methodology that has led to new polymeric materials with many applications, such as drug delivery, organic electronics, and photonic crystals.

SUMMARY

Certain embodiments provide photosensitive compositions, each composition comprising a ruthenium carbene metathesis catalyst of Formula (II):

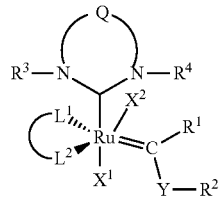

(II)

admixed within a polymerizable material matrix comprising at least one unsaturated organic precursor, including ROMP or cross-metathesis precursors;

wherein $L^1$, and $L^2$ are independently neutral electron donor ligands, linked by a hydrocarbylene linking group such as an alkylene, substituted alkylene, heteroalkylene, substituted heteroalkene, arylene, substituted arylene, heteroarylene, or substituted heteroarylene linkage, such that when taken together with the Ru to which they are bound or coordinated, form a 5, 6, or 7-membered ring;

$X^1$ and $X^2$ are independent anionic ligands, positioned cis with respect to one;

Y is O, N—$R^1$, or S, preferably O; and

Q is a two-atom linkage having the structure —$CR^{11}R^{12}$—$CR^{13}R^{14}$— or —$CR^{11}$=$CR^{13}$—, preferably —$CR^{11}R^{12}$—$CR^{13}R^{14}$—, wherein $R^{11}$, $R^{12}$, $R^{13}$, and $R^{14}$ are independently selected from hydrogen, hydrocarbyl, substituted hydrocarbyl, heteroatom-containing hydrocarbyl, substituted heteroatom-containing hydrocarbyl, and functional groups.

$R^1$ and $R^2$ are independently hydrogen, optionally substituted hydrocarbyl, optionally substituted heteroatom-containing hydrocarbyl, functional groups, or may be linked to form a cyclic group, which may be aliphatic or aromatic, and may contain substituents and/or heteroatoms;

$R^3$ and $R^4$ are independently optionally substituted hydrocarbyl, or optionally substituted heteroatom-containing hydrocarbyl, preferably a substituted adamantyl or substituted phenyl, and may contain substituents and/or heteroatoms; and In some of these compositions

is an aromatic bidentate diamine, for example a substituted phenanthroline.

In some specific embodiments, the metathesis catalyst comprises a compound having a structure:

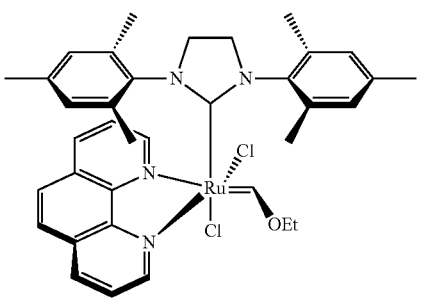

In other specific embodiments, the metathesis catalyst of the photosensitive composition, upon activation by irradiation of light of at least one wavelength in a range of from about 150 nm to about 800 nm, can crosslink or polymerize at least one of the unsaturated organic precursors.

Other embodiments provide methods of patterning polymeric image on a substrate, each method comprising; (a) depositing a layer of one of the inventive photosensitive compositions on a substrate; (b) irradiating a portion of the layer of photosensitive composition with a light comprising at least one wavelength in a range of from about 150 to about 800 nm, or a sub-range therewithin, so as to polymerize the irradiated portion of the layer, thereby providing polymerized and unpolymerized nor non-irradiated regions in the layer. In other embodiments, the methods further comprise removing the unpolymerized region of the pattern. Still other embodiments include polymerized compositions or articles prepared according to one of these methods. In more particular embodiments, the formed polymer layers are resistant to chemical reagents, including corrosive reagents, such as aqueous HF.

Still other embodiments provide photosensitive compositions, each comprising a more general range of Fischer-type carbene ruthenium metathesis catalysts admixed or dissolved within a polymerizable material matrix comprising at least one unsaturated organic precursor and at least one unsaturated tethered organometallic precursor, each organic and organometallic precursor having at least one alkene or one alkyne bond, wherein the ruthenium carbene catalyst can be activated by irradiation by light having at least one wavelength in a range of from about 150 to about 800 nm. The term, "a more general range of Fischer-type carbene ruthenium metathesis catalysts" is intended to include any one of the ruthenium metathesis catalysts described within this specification. In some of these embodiments, the at least one unsaturated organic precursor is a ROMP or cross-metathesis precursor. In some of these embodiments, the organometallic moiety comprises a Group 3 to Group 12 transition metal, preferably Fe, Co, Ni, Ti, Al, Cu, Zn, Ru, Rh, Ag, Ir, Pt, Au, or Hg, which may be capable of catalyzing the oxidation or reduction of an organic substrate under oxidizing or reducing conditions, or both. The organometallic moiety may also be capable of catalyzing metathesis or cross-coupling reactions or splitting water.

Other embodiments provide photosensitive compositions, each also comprising a more general range of Fischer-type carbene ruthenium metathesis catalyst admixed or dissolved within a polymerizable material matrix comprising at least one unsaturated organic precursor, each organic precursor having at least one alkene or one alkyne bond; wherein the ruthenium carbene catalyst can be activated by irradiation by light having at least one wavelength in a range of from about 150 to about 800 nm, or a sub-range therewithin; where the at least one unsaturated organic precursor comprises a compound having a structure:

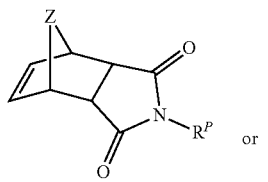 or 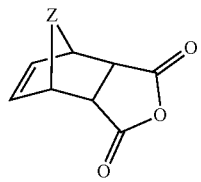 or

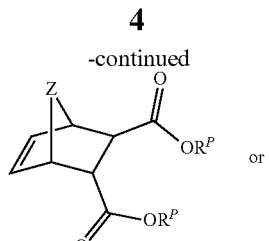 or

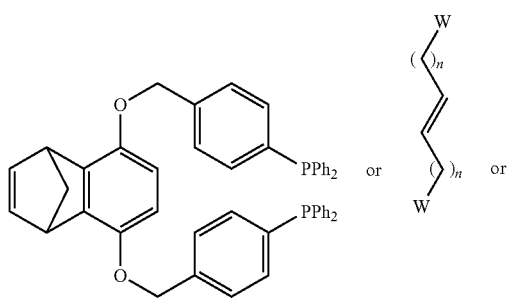 or

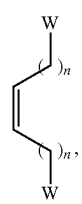

wherein

Z is —O— or $C(R_a)(R_b)$;

$R^P$ is independently H; or $C_{1-6}$ alkyl optionally substituted at the distal terminus with —N(Ra)(R$_b$), —O—R$_a$, —C(O)O—R$_a$, —OC(O)—($C_{1-6}$ alkyl), or —OC(O)—($C_{6-10}$ aryl); or an optionally protected sequence of 3 to 10 amino acids (preferably including R-G-D or arginine-glycine-aspartic acid);

W is independently —N(Ra)(R$_b$), —O—R$_a$, or —C(O)O—R$_a$, —P(O)(OR$_a$)$_2$, —SO$_2$(OR$_a$), or SO$_3^-$;

R$_a$ and R$_b$ are independently H or $C_{1-6}$ alkyl;

the $C_{6-10}$ aryl is optionally substituted with 1, 2, 3, 4, or 5 optionally protected hydroxyl groups (the protected hydroxyl groups preferably being benzyl); and n is independently 1, 2, 3, 4, 5, or 6.

In some embodiments, the unsaturated organic precursor may be mono- or poly-functionalized In those compositions or methods described as using the more general range of Fischer-type carbene ruthenium metathesis catalyst, such catalysts may comprise:

(a) a catalyst generated in situ by the reaction between:
a quenching agent, such as

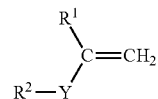

and a metathesis catalyst of Formula (IA), (IB), (IIIA), or (IIIB);

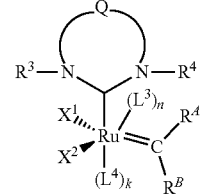
(IA)

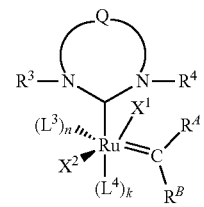
(IB)

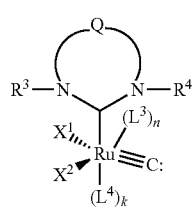
(IIIA)

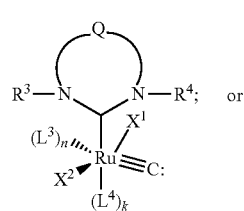
(IIIB)

or (b) a catalyst generated in situ by the reaction between

a quenching agent of

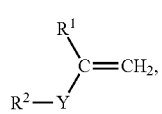

and a metathesis catalyst of Formula (IA), (IB), (IIIA), or (IIIB); or (c) a metathesis catalyst of Formula (II)

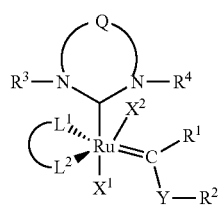
(II)

wherein:

$L^1$, $L^2$, $L^3$, and $L^4$ are independently neutral electron donor ligands;

$L^1$ and $L^2$ are linked by a hydrocarbylene linking group such as an alkylene, substituted alkylene, heteroalkylene, substituted heteroalkene, arylene, substituted arylene, heteroarylene, or substituted heteroarylene linkage, such that when taken together with the Ru to which they are bound or coordinated, form a 5, 6, or 7-membered ring.

k and n are independently 0 or 1;

$X^1$ and $X^2$ are anionic ligands;

Y is O, N—$R^1$, or S; and

Q is a two-atom linkage having the structure —$CR^{11}R^{12}$—$CR^{13}R^{14}$— or —$CR^{11}$=$CR^{13}$—, preferably —$CR^{11}R^{12}$—$CR^{13}R^{14}$—, wherein $R^{11}$, $R^{12}$, $R^{13}$, and $R^{14}$ are independently selected from hydrogen, hydrocarbyl, substituted hydrocarbyl, heteroatom-containing hydrocarbyl, substituted heteroatom-containing hydrocarbyl, and functional groups.

$R^1$, $R^2$, $R^A$, and $R^B$ are independently hydrogen, optionally substituted hydrocarbyl, optionally substituted heteroatom-containing hydrocarbyl, functional groups, or may be linked to form a cyclic group, which may be aliphatic or aromatic, and may contain substituents and/or heteroatoms;

$R^3$ and $R^4$ are independently optionally substituted hydrocarbyl, or optionally substituted heteroatom-containing hydrocarbyl; and wherein any two or more of $X^1$, $X^2$, $L^1$, $L^2$, $L^3$, $R^1$, and $R^2$ can be taken together to form one or more cyclic groups.

Particularly attractive catalysts include those having structures such as

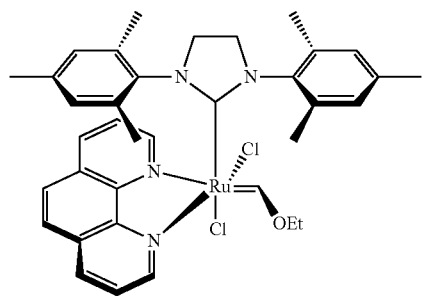

or substituted analogs thereof, or where the metathesis catalyst is generated in situ by the reaction between:

a quenching agent of

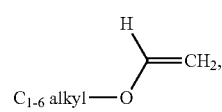

preferably

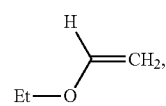

and a metathesis catalyst of structure:

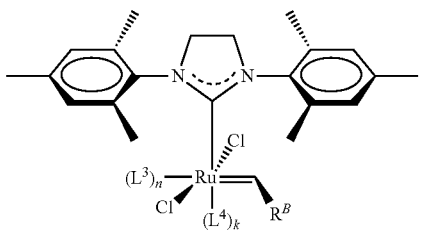

where $L^3$, $L^4$, $R^B$, n and k are defined as above.

Typically, the ruthenium metathesis catalyst is present at a concentration in the compositions in a range of from about 0.001% to about 5% by weight, relative to the weight of the entire composition.

The photosensitive compositions may be liquids, having a viscosity suitable for spin coating, dip coating, or spraying, or may be gelled, semi-solid or solid films.

The methods of using these photosensitive composition may comprise: (a) depositing at least one layer of a photosensitive composition on a substrate; (b) irradiating a portion of the layer of photosensitive composition with a light comprising a wavelength in a range of from about 150 to about 800 nm, or a sub-range therewithin, so as to polymerize the irradiated portion of the layer, thereby providing a patterned layer of polymerized and unpolymerized regions. Such methods may also further comprise removing the unpolymerized region of the pattern.

Additional embodiments provide polymerized composition or an article of manufacture comprising the polymerize composition as prepared according to any one of the methods described herein. The compositions may be patterned layers or solid objects. In certain embodiments, the compositions can be used to form tissue scaffolds, the scaffolds being either alone or populated with tissue or cell populations (for example, stem cells) and methods of treatment using such scaffolds.

While the compositions and methods are suitable for forming patterned polymer layers, the same compositions and analogous methods can also be used to prepare three-dimensional structures. Certain embodiments provide, then, methods comprising: (a) depositing at least two layers of a composition having at least one alkene or alkyne capable of undergoing a metathesis polymerization or crosslinking reaction, said deposition forming a stacked assembly; (b) irradiating at least a portion of the stacked assembly with light, such that light penetrates and irradiates at least two layers of the stacked assembly, under conditions sufficient to polymerize or crosslink at least portions of adjacent layers of the stacked assembly; wherein each layer comprises a Fischer-type carbene ruthenium metathesis catalyst admixed or dissolved therein. The Fischer-type carbene ruthenium metathesis catalyst may be one of those metathesis catalysts described herewithin.

Some of the embodiments involving stacked assemblies provide that the light passes through and irradiates at all layers of the stacked assembly, under conditions sufficient to polymerize or crosslink at least portions of adjacent layers of the stacked assembly. The irradiating may be done by patterned exposure of light to the stacked composition, so as to provide a three-dimensional pattern of polymerized and unpolymerized regions through the stacked assembly. Such patterning may be accomplished, as generally applicable in the other compositions and methods, through use of a photomask, by a direct writing application of light, or by interference, nanoimprint, or diffraction gradient lithography.

In these methods, each layer of comprises a pre-formed polymer which may be the same or different from other pre-formed polymer(s) in the other layer(s). Adjacent layers may be compositionally the same or different. Block co-polymers are attractive in this regard, particularly where the at least one layer of block copolymer comprises a dendritic (wedge) or brush (graft, bottlebrush) copolymer. Block co-polymers are also attractive in this regard wherein the polymer is at least one layer of block copolymer exhibiting domains having dimensions in a range of from about 5 to about 1500 nanometer domains, or in a range of from about 75 to about 300 nm.

Such 3-dimensional compositions (including their methods of preparation) are attractive as photonic or chemochromic structures having specifically tailored dimensions and feature sizes.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings:

FIGS. 3A and 3B illustrate embodiments of the present disclosure related to the polymerization of dicyclopentadiene and functionalized polymers.

DETAILED DESCRIPTION OF ILLUSTRATIVE EMBODIMENTS

Figure 1:
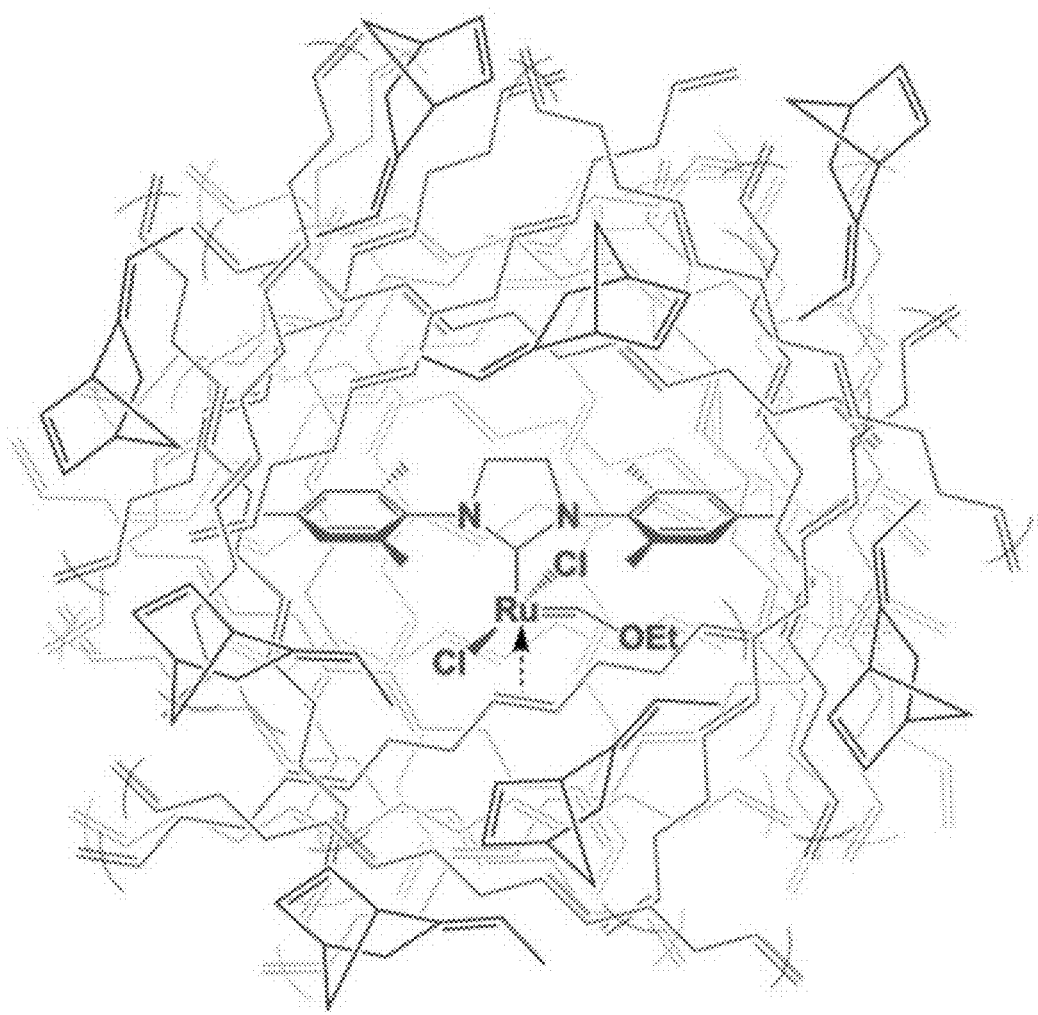
FIG. 1 is a cartoon depicting the proposed environment of the PLOMP resist. While not being bound by the correctness of any particular theory, it is believed that the viscous, olefin rich solution stabilized the sensitive vinyl ether complex through dative bonding, as depicted. The photoactivated catalyst crosslinks the ethylidene norbornene molecules into the polymerizable material matrix of poly(COD).

The present invention relates to method of metathesizing olefins using catalysts previously considered to be practically inactive. These methods provide for novel photosensitive compositions, their use as photoresists, and methods related to patterning polymer layers on substrates. Further, modifications to the compositions and method provide for an unprecedented functionalization of the compositions, useful for example in the preparation of sensors, drug delivery systems, and tissue scaffolds. The novel compositions and associated methods also provide for the opportunity to prepare 3-dimensional objects which provide new access to critically dimensioned devices, including for example photonic devices.

Patterning functional materials is a central challenge across many fields of science. The ability to lithographically fabricate micro- and nanostructures has been one of the most impactful technological breakthroughs of the last century. In part due to the complexity of the chemical processes in photoresists, there is a limited variety of materials that can currently be patterned with photolithography. The present invention provides for the use of a wide variety of materials in negative tone photoresists using photoactivated olefin metathesis catalysts, which can be quickly prepared in a one-pot synthesis from commercially available starting materials. In some embodiments, the resist is based on substituted ruthenium vinyl ether complexes, widely regarded as practically inactive towards olefin metathesis. The combination of these photoactivated catalysts with the fidelity and functional group tolerance of ruthenium-mediated olefin metathesis enables a host of new possibilities for photopatterned materials.

Further, the methods and polymerized compositions described herein may serve as templates for the adhesion of biological material, catalyst-functionalized surfaces for electrochemical devices, and unique nanostructures with resonant optical properties. Additionally, the (patterned) polymerized materials may be designed to be more susceptible to a specific chemical or physical decomposition processes or to serve as a sacrificial scaffold or template. As well, the methods and compositions provide an ability to tune the crosslinking density of the polymerized compositions through, for example, optical gradients or patterning, which affect the material properties, including the mechanical modulus, density, degree of functional group incorporation, refractive index and permeability to gas and liquids.

The present invention may be understood more readily by reference to the following description taken in connection with the accompanying Figures and Examples, all of which form a part of this disclosure. It is to be understood that this invention is not limited to the specific products, methods, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer to compositions and methods of making and using said compositions. That is, where the disclosure describes or claims a feature or embodiment associated with a composition or a method of making or using a composition, it is appreciated that such a description or claim is intended to extend these features or embodiment to embodiments in each of these contexts (i.e., compositions, methods of making, and methods of using).

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially" of. For those embodiments provided in terms of "consisting essentially of," the basic and novel characteristic(s) is the operability of the methods (or the compositions or devices derived therefrom) as providing a photochemically activated metathesis system.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

Throughout this specification, words are to be afforded their normal meaning, as would be understood by those skilled in the relevant art. However, so as to avoid misunderstanding, the meanings of certain terms will be specifically defined or clarified.

The present invention(s) include a range of pre-polymerized compositions comprising at least one ruthenium carbene metathesis catalyst, methods of polymerizing these compositions, as well as their polymerized products, including the specific devices or articles derived therefrom. While not intending to be limited to any particular embodiment(s), these compositions may be described as including (1) novel and non-obvious ruthenium carbene metathesis catalysts, operable over the range of polymer compositions, structures and products; (2) novel and non-obvious olefin precursors and polymerizable matrices, each of which may include any one or more of the range of ruthenium carbene metathesis catalysts described herein (these may be described as one of "a more general range of Fischer-type carbene ruthenium metathesis catalysts"); and (3) novel and non-obvious superstructures which can be prepared using any one or more of ruthenium carbene metathesis catalyst and one or more reactive polymers or polymerizable matrices. Each of these is described more fully below. For wording efficiency, the various elements of the invention(s) are described individually, though it should be recognized that the invention contemplates combinations thereof.

General Metathesis Description

The present disclosure describes compositions which are novel both in their choice of olefinic substrates and in the catalysts used to prepare the prepolymerized and polymerized compositions. These combinations of novel substrates and catalysts offer materials which exhibit properties or ways of handling these materials not previously recognized. These novel substrates and catalysts will be discussed separately, but it should be appreciated that the present invention considers each combination to be within the scope of the invention.

The present invention includes embodiments related to compositions and methods of metathesizing unsaturated organic precursors, each method comprising irradiating a Fischer-type carbene ruthenium metathesis catalyst with at least one wavelength of light in the presence of at least one unsaturated organic precursor, so as to metathesize at least one alkene or one alkyne bond within the matrices of the at least one precursors. For purposes of the present disclosure, so-called "Fischer-type" carbenes are defined, as comprising a non-persistent carbene having pi-donor substituents, such as alkoxy and alkylated amino groups, as well as hydrogen and alkyl substituents on the non-persistent carbenoid carbon. Alkoxy and alkylated amino groups on the carbene carbon render Fischer-type carbenes, especially those of ruthenium, virtually inert relative to their "Schrock-type" cogeners. In fact, the addition of substituted vinyl ethers or vinyl amines, for example, can virtually inactivate a ruthenium metathesis catalyst containing a "Schrock-type" carbene, by forming the corresponding Fischer-type derivative. These Fischer-type carbene complexes are widely considered inactive due to the electronics of the carbene. In fact, ethyl vinyl ether is commonly used to quench ROMP (Ring Opening Metathesis Polymerization) reactions. The following descriptions now demonstrate that these Ruthenium complexes and their "quenched" derivatives undergo further chemistry when photochemically activated.

Catalysts

The primary, though not exclusive focus, of the present invention involves the use of higher oxidation state metals, including complexes based on Group 8 metals, such as Os and Ru. In the present invention, Fischer-type carbene complexes based on ruthenium are especially preferred, particularly those further characterized as Grubbs' catalysts. These catalysts have been described, inter alia, in U.S. Pat. Nos. 5,312,940; 5,342,909; 5,750,815; 5,831,108; 5,917, 071; 5,969,170; 5,977,393; 6,048,993; 6,111,121; 6,153, 778; 6,211,391; 6,284,852; 6,313,332; 6,426,419; 6,486, 279; 6,504,041; 6,515,084; 6,624,265; 6,759,537; 6,806, 325; 6,818,586; 7,102,047; 7,288,666; 7,329,758; and 7,750,172 and U.S. Patent Application Publ. Nos. 2001/ 0039360; 2002/0013473; 2002/0022733; 2002/0055598; 2002/0177710; 2003/0069374; 2003/0181609; 2005/ 0113590; 2006/0241317; 2009/0012248; 2009/0012254; and 2011/0124868, each of which is incorporated by reference for its teaching of catalyst and catalyst precursor structure. The present invention is especially directed to compounds which may be characterized by the umbrella moniker of "Grubb's catalysts" in which the non-persistent carbene is contains an O, N, or S bonded directly to the Ru=C carbene moiety; i.e., is also described as containing a Fischer-type carbene.

In certain embodiments, the Fischer-type carbene ruthenium metathesis catalyst used in the photochemically activated metathesis compositions is a metathesis catalyst generated in situ by the reaction between a quenching agent of formula

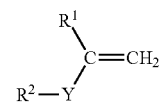

and a metathesis catalyst of Formula (IA) or (IB).

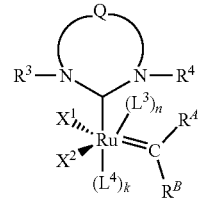

(IA)

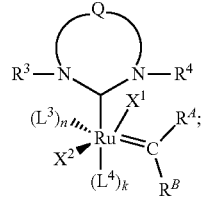

(IB)

wherein:

$L^3$, and $L^4$ are independently neutral electron donor ligands;

k and n are independently 0 or 1;

$X^1$ and $X^2$ are anionic ligands;

Y is O, N—$R^1$, or S; preferably O or N(H); and

Q is a two-atom linkage having the structure —$CR^{11}R^{12}$—$CR^{13}R^{14}$— or —$CR^{11}$=$CR^{13}$—, preferably —$CR^{11}R^{12}$—$CR^{13}R^{14}$—, wherein $R^{11}$, $R^{12}$, $R^{13}$, and $R^{14}$ are independently selected from hydrogen, hydrocarbyl, substituted hydrocarbyl, heteroatom-containing hydrocarbyl, substituted heteroatom-containing hydrocarbyl, and functional groups.

$R^1$, $R^2$, $R^A$, and $R^B$ are independently hydrogen, optionally substituted hydrocarbyl, optionally substituted heteroatom-containing hydrocarbyl, functional groups, or may be linked to form a cyclic group, which may be aliphatic or aromatic, and may contain substituents and/or heteroatoms;

$R^3$ and $R^4$ are independently optionally substituted hydrocarbyl, or optionally substituted heteroatom-containing hydrocarbyl; and wherein any two or more of $X^1$, $X^2$, $R^1$, and $R^2$ can be taken together to form one or more cyclic groups.

The Fischer-type carbene ruthenium metathesis catalyst may also be separately described or represented by the isomer structures (IIA) and (IIB):

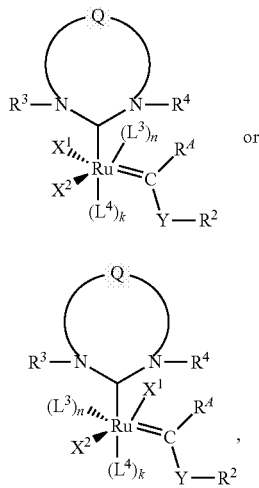

wherein $L^3$, $L^4$, k, n, $X^1$, $X^2$, Y, Q, $R^2$, $R^3$, and $R^4$ are as described above.

In some embodiments, photoresists may also be prepared using and comprising ruthenium carbide catalysts generated in situ by the reaction between a quenching agent formula

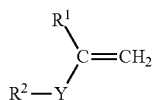

and metathesis catalysts having a structure of Formula (IIIA or IIIB), or acidified derivatives thereof:

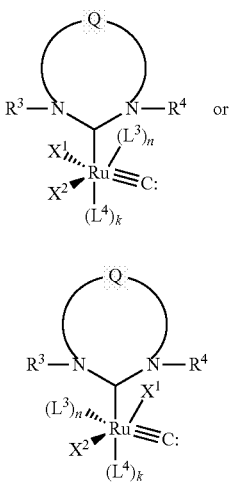

where $L^2$, $L^3$, k, n, $X^1$, $X^2$, Y, Q, $R^3$, and $R^4$ are as described above. See Example 7.

In particular embodiments, the metathesis catalyst is generated in situ by the reaction between:
a quenching agent of

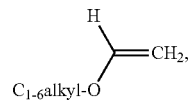

where $C_{1-6}$ is ethyl, propyl, or butyl, preferably

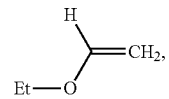

and a metathesis catalyst of structure:

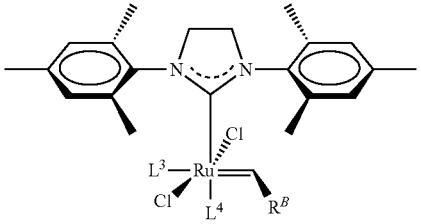

In certain additional embodiments of the present invention, $X^1$, $X^2$, $L^2$, $L^3$, $R^1$, and $R^2$ are described as follows.

Throughout this specification, words are to be afforded their normal meaning, as would be understood by those skilled in the relevant art. However, so as to avoid misunderstanding, the meanings of certain terms will be specifically defined or clarified.

Where a given catalyst structure is provided, that structure is considered a specific embodiment. However, it should be appreciated that catalytic cycles by their nature involve transient intermediates or compounds which are transformed during the course of their reaction. As such, the term catalyst, when applied to a given structure, should also be considered to include those transient structures associated with the catalytic cycles of the provided structures By "substituted" as in "substituted hydrocarbyl," "substituted alkyl," "substituted aryl," and the like, as alluded to in some of the aforementioned definitions, is meant that in the hydrocarbyl, alkyl, aryl, heteroaryl, or other moiety, at least one hydrogen atom bound to a carbon (or other) atom is replaced with one or more non-hydrogen substituents. Examples of such substituents include, without limitation: functional groups referred to herein as "Fn," such as halo (e.g., F, Cl, Br, I), hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_1$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl ((CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO—), carbamoyl (—(CO)—NH$_2$), mono-($C_1$-$C_{24}$ alkyl)-substituted carbamoyl (—(CO)NH($C_1$-$C_{24}$ alkyl)), di- ($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ alkyl)), di-($C_1$-$C_{24}$ haloalkyl)-substituted carbamoyl (—(CO)—N($C_1$-$C_{24}$ alkyl)$_2$), mono-($C_5$-$C_{24}$ aryl)-substituted carbamoyl (—(CO)—NH-aryl), di-($C_5$-$C_{24}$ aryl)substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl, thiocarbamoyl (—(CS)—NH$_2$), mono-($C_1$-$C_{24}$ alkyl)-substituted thiocarbamoyl (—(CO)—NH($C_1$-$C_{24}$ alkyl)), di-($C_1$-$C_{24}$ alkyl)-substituted thiocarbamoyl (—(CO)—N($C_1$-$C_{24}$ alkyl)$_2$), mono-($C_5$-$C_{24}$ aryl)substituted thiocarbamoyl (—(CO)—NH-aryl), di-($C_5$-$C_{24}$ aryl)-substituted thiocarbamoyl (—(CO)—N($C_5$-$C_{24}$ aryl)$_2$), di-N—($C_1$-$C_{24}$ alkyl), N—($C_5$-$C_{24}$ aryl)-substituted thiocarbamoyl, carbamido (—NH—(CO)—NH$_2$), cyano (—C≡N), cyanato (—O—C≡N), thiocyanato (—S—C≡N), formyl (—(CO)—H), thioformyl (—(CS)—H), amino (—NH$_2$), mono-($C_1$-$C_{24}$ alkyl)-substituted amino, di-($C_1$-$C_{24}$ alkyl)-substituted amino, mono-($C_5$-$C_{24}$ aryl)substituted amino, di-($C_5$-$C_{24}$ aryl)-substituted amino, $C_1$-$C_{24}$ alkylamido (—NH—(CO)-alkyl), $C_6$-$C_{24}$ arylamido (—NH—(CO)-aryl), imino (—CR=NH where R=hydrogen, $C_1$-$C_{24}$ alkyl, C5-C24 aryl, $C_6$-$C_{24}$ alkaryl, $C_6$-$C_{24}$ aralkyl, etc.), $C_2$-$C_{20}$ alkylimino (—CR=N(alkyl), where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$OH), sulfonate (SO$_2$O—), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_1$-$C_{24}$ monoalkylaminosulfonyl-SO$_2$—N(H) alkyl), $C_1$-$C_{24}$ dialkylaminosulfonyl-SO$_2$—N(alkyl)$_2$, $C_5$-$C_{24}$ arylsulfonyl (—SO$_2$-aryl), boryl (—BH$_2$), borono (—B(OH)$_2$), boronato (—B(OR)$_2$ where R is alkyl or other hydrocarbyl), phosphono (—P(O)(OH)$_2$), phosphonato (—P(O)(O)$_2$), phosphinato (P(O)(O—)), phospho (—PO$_2$), and phosphine (—PH$_2$); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably C2-C6 alkynyl), $C_5$-$C_{24}$ aryl (preferably $C_5$-$C_{24}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl). Within these substituent structures, the "alkyl," "alkylene," "alkenyl," "alkenylene," "alkynyl," "alkynylene," "alkoxy," "aromatic," "aryl," "aryloxy," "alkaryl," and "aralkyl" moieties may be optionally fluorinated or perfluorinated. Additionally, reference to alcohols, aldehydes, amines, carboxylic acids, ketones, or other similarly reactive functional groups also includes their protected analogs. For example, reference to hydroxy or alcohol also includes those substituents wherein the hydroxy is protected by acetyl (Ac), benzoyl (Bz), benzyl (Bn, Bnl), β-Methoxyethoxymethyl ether (MEM), dimethoxytrityl, [bis-(4-methoxyphenyl)phenylmethyl] (DMT), methoxymethyl ether (MOM), methoxytrityl [(4-methoxyphenyl)diphenylmethyl, MMT), p-methoxybenzyl ether (PMB), methylthiomethyl ether, pivaloyl (Piv), tetrahydropyranyl (THP), tetrahydrofuran (THF), trityl (triphenylmethyl, Tr), silyl ether (most popular ones include trimethylsilyl (TMS), tert-butyldimethylsilyl (TBDMS), tri-isopropylsilyloxymethyl (TOM), and triisopropylsilyl (TIPS) ethers), ethoxyethyl ethers (EE). Reference to amines also includes those substituents wherein the amine is protected by a BOC glycine, carbobenzyloxy (Cbz), p-methoxybenzyl carbonyl (Moz or MeOZ), tert-butyloxycarbonyl (BOC), 9-fluorenylmethyloxycarbonyl (FMOC), acetyl (Ac), benzoyl (Bz), benzyl (Bn), carbamate, p-methoxybenzyl (PMB), 3,4-dimethoxybenzyl (DMPM), p-methoxyphenyl (PMP), tosyl (Ts) group, or sulfonamide (Nosyl & Nps) group. Reference to substituent containing a carbonyl group also includes those substituents wherein the carbonyl is protected by an acetal or ketal, acylal, or diathane group. Reference to substituent containing a carboxylic acid or carboxylate group also includes those substituents wherein the carboxylic acid or carboxylate group is protected by its methyl ester, benzyl ester, tert-butyl ester, an ester of 2,6-disubstituted phenol (e.g. 2,6-dimethylphenol, 2,6-diisopropylphenol, 2,6-di-tert-butylphenol), a silyl ester, an orthoester, or an oxazoline.

By "functionalized" as in "functionalized hydrocarbyl," "functionalized alkyl," "functionalized olefin," "functionalized cyclic olefin," and the like, is meant that in the hydrocarbyl, alkyl, aryl, heteroaryl, olefin, cyclic olefin, or other moiety, at least one hydrogen atom bound to a carbon (or other) atom is replaced with one or more functional groups such as those described herein and above. The term "functional group" is meant to include any functional species that is suitable for the uses described herein. In particular, as used herein, a functional group would necessarily possess the ability to react with or bond to corresponding functional groups on a substrate surface.

In addition, the aforementioned functional groups may, if a particular group permits, be further substituted with one or more additional functional groups or with one or more hydrocarbyl moieties such as those specifically enumerated above. Analogously, the abovementioned hydrocarbyl moieties may be further substituted with one or more functional groups or additional hydrocarbyl moieties such as those specifically enumerated.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

A neutral electron donor is any ligand which, when removed from a metal center in its closed shell electron configuration, has a neutral charge, i.e., is a Lewis base. In independent embodiments, the neutral electron donor comprises a phosphine, sulfonated phosphine, phosphite, phosphinite, phosphonite, arsine, stibine, ether, amine, amide, imine, sulfoxide, carboxyl, carbonyl, nitrosyl, a heterocycle containing nitrogen, sulfur, oxygen, or a mixture thereof (for example, pyridine), or thioether. In some embodiments, $L^4$ is phosphine, sulfonated phosphine, phosphite, phosphinite, phosphonite, arsine, stibine, ether, (including cyclic ethers), amine, amide, imine, sulfoxide, carboxyl, nitrosyl, pyridine, substituted pyridine, imidazole, substituted imidazole, pyrazine, substituted pyrazine or thioether. Exemplary ligands are trisubstituted phosphines. Preferred trisubstituted phosphines are of the formula $PR^{H1}R^{H2}R^{H3}$, where $R^{H1}$, $R^{H2}$, and $R^{H3}$ are each independently substituted or unsubstituted aryl or $C_1$-$C_{10}$ alkyl, particularly primary alkyl, secondary alkyl, or cycloalkyl. In other embodiments $L^4$ is trimethylphosphine (PMe$_3$), triethylphosphine (PEt$_3$), tri-n-butylphosphine (PBu$_3$), tri(ortho-tolyl)phosphine (P-o-tolyl$_3$), tri-tert-butylphosphine (P-tert-Bu$_3$), tricyclopentylphosphine (PCyclopentyl$_3$), tricyclohexylphosphine (PCy$_3$), triisopropylphosphine (P-i-Pr$_3$), trioctylphosphine (POct$_3$), triisobutylphosphine, (P-i-Bu$_3$), triphenylphosphine (PPh$_3$), tri(pentafluorophenyl)phosphine (P(C$_6$F$_5$)$_3$), methyldiphenylphosphine (PMePh$_2$), dimethylphenylphosphine (PMe$_2$Ph), or diethylphenylphosphine (PEt$_2$Ph).

In other embodiments, L$^3$ and L$^4$ include, without limitation, heterocycles containing nitrogen, sulfur, oxygen, or a mixture thereof.

Examples of nitrogen-containing heterocycles appropriate for L$^3$ and L$^4$ include pyridine, bipyridine, pyridazine, pyrimidine, bipyridamine, pyrazine, 1,3,5-triazine, 1,2,4-triazine, 1,2,3-triazine, pyrrole, 2H-pyrrole, 3H-pyrrole, pyrazole, 2H-imidazole, 1,2,3-triazole, 1,2,4-triazole, indole, 3H-indole, 1H-isoindole, cyclopenta(b)pyridine, indazole, quinoline, bisquinoline, isoquinoline, bisisoquinoline, cinnoline, quinazoline, naphthyridine, piperidine, piperazine, pyrrolidine, pyrazolidine, quinuclidine, imidazolidine, picolylimine, purine, benzimidazole, bisimidazole, phenazine, acridine, and carbazole. Additionally, the nitrogen-containing heterocycles may be optionally substituted on a non-coordinating heteroatom with a non-hydrogen substituent.

Examples of sulfur-containing heterocycles appropriate for L$^3$ and L$^4$ include thiophene, 1,2-dithiole, 1,3-dithiole, thiepin, benzo(b)thiophene, benzo(c)thiophene, thionaphthene, dibenzothiophene, 2H-thiopyran, 4H-thiopyran, and thioanthrene.

Examples of oxygen-containing heterocycles appropriate for L$^3$ and L$^4$ include 2H-pyran, 4H-pyran, 2-pyrone, 4-pyrone, 1,2-dioxin, 1,3-dioxin, oxepin, furan, 2H-1-benzopyran, coumarin, coumarone, chromene, chroman-4-one, isochromen-1-one, isochromen-3-one, xanthene, tetrahydrofuran, 1,4-dioxan, and dibenzofuran.

Examples of mixed heterocycles appropriate for L$^3$ and L$^4$ include isoxazole, oxazole, thiazole, isothiazole, 1,2,3-oxadiazole, 1,2,4-oxadiazole, 1,3,4-oxadiazole, 1,2,3,4-oxatriazole, 1,2,3,5-oxatriazole, 3H-1,2,3-dioxazole, 3H-1,2-oxathiole, 1,3-oxathiole, 4H-1,2-oxazine, 2H-1,3-oxazine, 1,4-oxazine, 1,2,5-oxathiazine, o-isooxazine, phenoxazine, phenothiazine, pyrano[3,4-b]pyrrole, indoxazine, benzoxazole, anthranil, and morpholine. Preferred L$^3$ and L$^4$ ligands are aromatic nitrogen-containing and oxygen-containing heterocycles, and particularly preferred L$^3$ and L$^4$ ligands are monocyclic N-heteroaryl ligands that are optionally substituted with 1 to 3, preferably 1 or 2, substituents. Specific examples of particularly preferred L$^3$ and L$^4$ ligands are pyridine and substituted pyridines, such as 3-bromopyridine, 4-bromopyridine, 3,5-dibromopyridine, 2,4,6-tribromopyridine, 2,6-dibromopyridine, 3-chloropyridine, 4-chloropyridine, 3,5-dichloropyridine, 2,4,6-trichloropyridine, 2,6-dichloropyridine, 4-iodopyridine, 3,5-diiodopyridine, 3,5-dibromo-4-methylpyridine, 3,5-dichloro-4-methylpyridine, 3,5-dimethyl-4-bromopyridine, 3,5-dimethylpyridine, 4-methylpyridine, 3,5-diisopropylpyridine, 2,4,6-trimethylpyridine, 2,4,6-triisopropylpyridine, 4-(tert-butyl)pyridine, 4-phenylpyridine, 3,5-diphenylpyridine, 3,5-dichloro-4-phenylpyridine, and the like.

In general, any substituents present on L$^3$ and L$^4$ are selected from halo, C$_1$-C$_{20}$ alkyl, substituted C$_1$-C$_{20}$ alkyl, C$_1$-C$_{20}$ heteroalkyl, substituted C$_1$-C$_{20}$ heteroalkyl, C$_5$-C$_{24}$ aryl, substituted C$_5$-C$_{24}$ aryl, C$_5$-C$_{24}$ heteroaryl, substituted C$_5$-C$_{24}$ heteroaryl, C$_6$-C$_{24}$ alkaryl, substituted C$_6$-C$_{24}$ alkaryl, C$_6$-C$_{24}$ heteroalkaryl, substituted C$_6$-C$_{24}$ heteroalkaryl, C$_6$-C$_{24}$ aralkyl, substituted C$_6$-C$_{24}$ aralkyl, C$_6$-C$_{24}$ heteroaralkyl, substituted C$_6$-C$_{24}$ heteroaralkyl, and functional groups, with suitable functional groups including, without limitation, C$_1$-C$_{20}$ alkoxy, C$_5$-C$_{24}$ aryloxy, C$_2$-C$_{20}$ alkylcarbonyl, C$_6$-C$_{24}$ arylcarbonyl, C$_2$-C$_{20}$ alkylcarbonyloxy, C$_6$-C$_{24}$ arylcarbonyloxy, C$_2$-C$_{20}$ alkoxycarbonyl, C$_6$-C$_{24}$ aryloxycarbonyl, halocarbonyl, C$_2$-C$_{20}$ alkylcarbonato, C$_6$-C$_{24}$ arylcarbonato, carboxy, carboxylato, carbamoyl, mono-(C$_1$-C$_{20}$ alkyl)-substituted carbamoyl, di-(C$_1$-C$_{20}$ alkyl)-substituted carbamoyl, di-N—(C$_1$-C$_{20}$ alkyl), N—(C$_5$-C$_{24}$ aryl)-substituted carbamoyl, mono-(C$_5$-C$_{24}$ aryl)-substituted carbamoyl, di-(C$_6$-C$_{24}$ aryl)-substituted carbamoyl, thiocarbamoyl, mono-(C$_1$-C$_{20}$ alkyl)-substituted thiocarbamoyl, di-(C$_1$-C$_{20}$ alkyl)-substituted thiocarbamoyl, di-N—(C$_1$-C$_{20}$ alkyl)-N—(C$_6$-C$_{24}$ aryl)-substituted thiocarbamoyl, mono-(C$_6$-C$_{24}$ aryl)-substituted thiocarbamoyl, di-(C$_6$-C$_{24}$ aryl)-substituted thiocarbamoyl, carbamido, formyl, thioformyl, amino, mono-(C$_1$-C$_{20}$ alkyl)-substituted amino, di-(C$_1$-C$_{20}$ alkyl)-substituted amino, mono-(C$_5$-C$_{24}$ aryl)-substituted amino, di-(C$_5$-C$_{24}$ aryl)-substituted amino, di-N—(C$_1$-C$_{20}$ alkyl), N—(C$_5$-C$_{24}$ aryl)-substituted amino, C$_2$-C$_{20}$ alkylamido, C$_6$-C$_{24}$ arylamido, imino, C$_1$-C$_{20}$ alkylimino, C$_5$-C$_{24}$ arylimino, nitro, and nitroso. In addition, two adjacent substituents may be taken together to form a ring, generally a five- or six-membered alicyclic or aryl ring, optionally containing 1 to 3 heteroatoms and 1 to 3 substituents as above.

Preferred substituents on L$^3$ and L$^4$ include, without limitation, halo, C$_1$-C$_{12}$ alkyl, substituted C$_1$-C$_{12}$ alkyl, C$_1$-C$_{12}$ heteroalkyl, substituted C$_1$-C$_{12}$ heteroalkyl, C$_5$-C$_{14}$ aryl, substituted C$_5$-C$_{14}$ aryl, C$_5$-C$_{14}$ heteroaryl, substituted C$_5$-C$_{14}$ heteroaryl, C$_6$-C$_{16}$ alkaryl, substituted C$_6$-C$_{16}$ alkaryl, C$_6$-C$_{16}$ heteroalkaryl, substituted C$_6$-C$_{16}$ heteroalkaryl, C$_6$-C$_{16}$ aralkyl, substituted C$_6$-C$_{16}$ aralkyl, C$_6$-C$_{16}$ heteroaralkyl, substituted C$_6$-C$_{16}$ heteroaralkyl, C$_1$-C$_{12}$ alkoxy, C$_5$-C$_{14}$ aryloxy, C$_2$-C$_{12}$ alkylcarbonyl, C$_6$-C$_{14}$ arylcarbonyl, C$_2$-C$_{12}$ alkylcarbonyloxy, C$_6$-C$_{14}$ arylcarbonyloxy, C$_2$-C$_{12}$ alkoxycarbonyl, C$_6$-C$_{14}$ aryloxycarbonyl, halocarbonyl, formyl, amino, mono-(C$_1$-C$_{12}$ alkyl)-substituted amino, di-(C$_1$-C$_{12}$ alkyl)-substituted amino, mono-(C$_5$-C$_{14}$ aryl)-substituted amino, di-(C$_5$-C$_{14}$ aryl)-substituted amino, and nitro.

Of the foregoing, the most preferred substituents are halo, C$_1$-C$_6$ alkyl, C$_1$-C$_6$ haloalkyl, C$_1$-C$_6$ alkoxy, phenyl, substituted phenyl, formyl, N,N-di(C$_1$-C$_6$ alkyl)amino, nitro, and nitrogen heterocycles as described above (including, for example, pyrrolidine, piperidine, piperazine, pyrazine, pyrimidine, pyridine, pyridazine, etc.).

In certain embodiments, L$^3$ and L$^4$ may also be taken together to form a bidentate or multidentate ligand containing two or more, generally two, coordinating heteroatoms such as N, O, S, or P, with preferred such ligands being diimine ligands of the Brookhart type. One representative bidentate ligand has the structure of formula (VI)

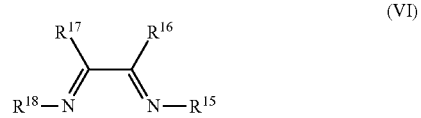

(VI)

wherein R$^{15}$, R$^{16}$, R$^{17}$, and R$^{18}$ hydrocarbyl (e.g., C$_1$-C$_{20}$ alkyl, C$_2$-C$_{20}$ alkenyl, C$_2$-C$_{20}$ alkynyl, C$_5$-C$_{24}$ aryl, C$_6$-C$_{24}$ alkaryl, or C$_6$-C$_{24}$ aralkyl), substituted hydrocarbyl (e.g., substituted C$_1$-C$_{20}$ alkyl, C$_2$-C$_{20}$ alkenyl, C$_2$-C$_{20}$ alkynyl, C$_5$-C$_{24}$ aryl, C$_6$-C$_{24}$ alkaryl, or C$_6$-C$_{24}$ aralkyl), heteroatom-containing hydrocarbyl (e.g., C$_1$-C$_{20}$ heteroalkyl, C$_5$-C$_{24}$ heteroaryl, heteroatom-containing C$_6$-C$_{24}$ aralkyl, or heteroatom-containing C$_6$-C$_{24}$ alkaryl), or substituted heteroatom-containing hydrocarbyl (e.g., substituted C$_1$-C$_{20}$ heteroalkyl, C$_5$-C$_{24}$ heteroaryl, heteroatom-containing C$_6$-C$_{24}$ aralkyl, or heteroatom-containing $C_6$-$C_{24}$ alkaryl), or (1) $R^{15}$ and $R^{16}$, (2) $R^{17}$ and $R^{18}$, (3) $R^{16}$ and $R^{17}$, or (4) both $R^{15}$ and $R^{16}$, and $R^{17}$ and $R^{18}$, may be taken together to form a ring, i.e., an N-heterocycle. Preferred cyclic groups in such a case are five- and six-membered rings, typically aromatic rings.

$X^1$ and $X^2$ are anionic ligands, and may be the same or different, or are linked together to form a cyclic group, typically although not necessarily a five- to eight-membered ring. In preferred embodiments, $X^1$ and $X^2$ are each independently hydrogen, halide, or one of the following groups: $C_1$-$C_{20}$ alkyl, $C_5$-$C_{24}$ aryl, $C_1$-$C_{20}$ alkoxy, $C_5$-$C_{24}$ aryloxy, $C_2$-$C_{20}$ alkoxycarbonyl, $C_6$-$C_{24}$ aryloxycarbonyl, $C_2$-$C_{24}$ acyl, $C_2$-$C_{24}$ acyloxy, $C_1$-$C_{20}$ alkylsulfonato, $C_5$-$C_{24}$ arylsulfonato, $C_1$-$C_{20}$ alkylsulfanyl, $C_5$-$C_{24}$ arylsulfanyl, $C_1$-$C_{20}$ alkylsulfinyl, $NO_3$, —N=C=O, —N=C=S, or $C_5$-$C_{24}$ arylsulfinyl. Optionally, $X^1$ and $X^2$ may be substituted with one or more moieties selected from $C_1$-$C_{12}$ alkyl, $C_1$-$C_{12}$ alkoxy, $C_5$-$C_{24}$ aryl, and halide, which may, in turn, with the exception of halide, be further substituted with one or more groups selected from halide, $C_1$-$C_6$ alkyl, $C_1$-$C_6$ alkoxy, and phenyl. In more preferred embodiments, $X^1$ and $X^2$ are halide, benzoate, $C_2$-$C_6$ acyl, $C_2$-$C_6$ alkoxycarbonyl, $C_1$-$C_6$ alkyl, phenoxy, $C_1$-$C_6$ alkoxy, $C_1$-$C_6$ alkylsulfanyl, aryl, or $C_1$-$C_6$ alkylsulfonyl. In even more preferred embodiments, $X^1$ and $X^2$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethane-sulfonate. In the most preferred embodiments, $X^1$ and $X^2$ are each chloride.

$R^1$ and $R^2$ are independently selected from hydrogen, hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), heteroatom-containing hydrocarbyl (e.g., heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and substituted heteroatom-containing hydrocarbyl (e.g., substituted heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and functional groups. $R^1$ and $R^2$ may also be linked to form a cyclic group, which may be aliphatic or aromatic, and may contain substituents and/or heteroatoms. Generally, such a cyclic group will contain 4 to 12, preferably 5, 6, 7, or 8 ring atoms. In certain embodiments, $R^2$ is not hydrogen.

In some embodiments, $R^1$ is hydrogen and $R^2$ is selected from $C_1$-$C_{20}$ alkyl, $C_2$-$C_{20}$ alkenyl, and $C_5$-$C_{24}$ aryl, more preferably $C_1$-$C_6$ alkyl, $C_2$-$C_6$ alkenyl, and $C_5$-$C_{14}$ aryl. Still more preferably, $R^2$ is phenyl, methyl, ethyl, isopropyl, or t-butyl, optionally substituted with one or more moieties selected from $C_1$-$C_6$ alkyl, $C_1$-$C_6$ alkoxy, phenyl, and a functional group Fn as defined earlier herein. Most preferably, $R^2$ is phenyl or ethyl optionally substituted with one or more moieties selected from methyl, ethyl, chloro, bromo, iodo, fluoro, nitro, dimethylamino, methyl, methoxy, and phenyl. Optimally, $R^2$ is phenyl or ethyl.

Any two or more (typically two, three, or four) of $X^1$, $X^2$, $L^3$, $L^4$, $R^1$, and $R^2$ can be taken together to form a cyclic group, including bidentate or multidentate ligands, as disclosed, for example, in U.S. Pat. No. 5,312,940, the disclosure of which is incorporated herein by reference. When any of $X^1$, $X^2$, $L^3$, $L^4$, $R^1$, and $R^2$ are linked to form cyclic groups, those cyclic groups may contain 4 to 12, preferably 4, 5, 6, 7 or 8 atoms, or may comprise two or three of such rings, which may be either fused or linked. The cyclic groups may be aliphatic or aromatic, and may be heteroatom-containing and/or substituted. The cyclic group may, in some cases, form a bidentate ligand or a tridentate ligand. Examples of bidentate ligands include, but are not limited to, bisphosphines, dialkoxides, alkyldiketonates, and aryldiketonates.

In some embodiments, $R^3$ and $R^4$ are as defined above, with preferably at least one of $R^3$ and $R^4$, and more preferably both $R^3$ and $R^4$, being alicyclic or aromatic of one to about five rings, and optionally containing one or more heteroatoms and/or substituents. Q is a linker, typically a hydrocarbylene linker, including substituted hydrocarbylene, heteroatom-containing hydrocarbylene, and substituted heteroatom-containing hydrocarbylene linkers, wherein two or more substituents on adjacent atoms within Q may also be linked to form an additional cyclic structure, which may be similarly substituted to provide a fused polycyclic structure of two to about five cyclic groups. Q is often, although not necessarily, a two-atom linkage or a three-atom linkage.

Examples of N-heterocyclic carbene (NHC) ligands and acyclic diaminocarbene ligands include, but are not limited to, the following where DIPP or DiPP is diisopropylphenyl and Mes is 2,4,6-trimethylphenyl:

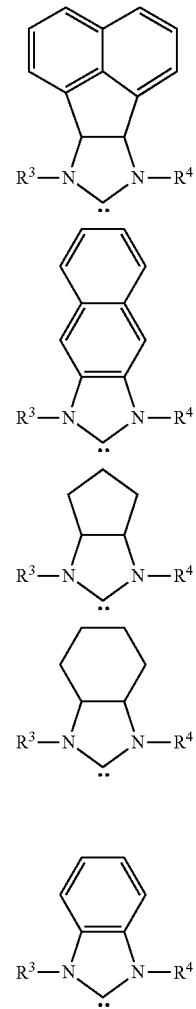

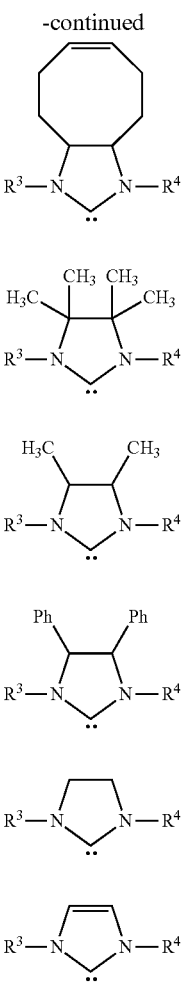

Additional examples of N-heterocyclic carbene (NHC) ligands and acyclic diaminocarbene ligands suitable as $L^1$ thus include, but are not limited to the following:

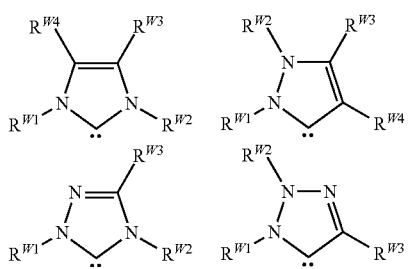

wherein $R^{W1}$, $R^{W2}$, $R^{W3}$, $R^{W4}$ are independently hydrogen, unsubstituted hydrocarbyl, substituted hydrocarbyl, or heteroatom containing hydrocarbyl, and where one or both of $R^{W3}$ and $R^{W4}$ may be in independently selected from halogen, nitro, amido, carboxyl, alkoxy, aryloxy, sulfonyl, carbonyl, thio, or nitroso groups.

Additional examples of suitable N-heterocyclic carbene (NHC) ligands are further described in U.S. Pat. Nos. 7,378,528; 7,652,145; 7,294,717; 6,787,620; 6,635,768; and 6,552,139 the contents of each are incorporated herein by reference.

In a more preferred embodiment, Q is a two-atom linkage having the structure —$CR^{11}R^{12}$—$CR^{13}R^{14}$—, or —$CR^{11}$=$CR^{13}$—, preferably —$CR^{11}R^{12}$—$CR^{13}R^{14}$—, wherein $R^{11}$, $R^{12}$, $R^{13}$, and $R^{14}$ are independently selected from hydrogen, hydrocarbyl, substituted hydrocarbyl, heteroatom-containing hydrocarbyl, substituted heteroatom-containing hydrocarbyl, and functional groups. Examples of functional groups here include without limitation carboxyl, $C_1$-$C_{20}$ alkoxy, $C_5$-$C_{24}$ aryloxy, $C_2$-$C_{20}$ alkoxycarbonyl, $C_5$-$C_{24}$ alkoxycarbonyl, $C_2$-$C_{24}$ acyloxy, $C_1$-$C_{20}$ alkylthio, $C_5$-$C_{24}$ arylthio, $C_1$-$C_{20}$ alkylsulfonyl, and $C_1$-$C_{20}$ alkylsulfinyl, optionally substituted with one or more moieties selected from $C_1$-$C_{12}$ alkyl, $C_1$-$C_{12}$ alkoxy, $C_5$-$C_{14}$ aryl, hydroxyl, sulfhydryl, formyl, and halide. $R^{11}$, $R^{12}$, $R^{13}$, and $R^{14}$ are preferably independently selected from hydrogen, $C_1$-$C_{12}$ alkyl, substituted $C_1$-$C_{12}$ alkyl, $C_1$-$C_{12}$ heteroalkyl, substituted $C_1$-$C_{12}$ heteroalkyl, phenyl, and substituted phenyl. Alternatively, any two of $R^{11}$, $R^{12}$, $R^{13}$, and $R^{14}$ may be linked together to form a substituted or unsubstituted, saturated or unsaturated ring structure, e.g., a $C_4$-$C_{12}$ alicyclic group or a $C_5$ or $C_6$ aryl group, which may itself be substituted, e.g., with linked or fused alicyclic or aromatic groups, or with other substituents. In one further aspect, any one or more of $R^{11}$, $R^{12}$, $R^{13}$, and $R^{14}$ comprises one or more of the linkers. Additionally, $R^3$ and $R^4$ may be unsubstituted phenyl or phenyl substituted with one or more substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide. Furthermore, $X^1$ and $X^2$ may be halogen.

When $R^3$ and $R^4$ are aromatic, they are typically although not necessarily composed of one or two aromatic rings, which may or may not be substituted, e.g., $R^3$ and $R^4$ may be phenyl, substituted phenyl, biphenyl, substituted biphenyl, or the like. In one preferred embodiment, $R^3$ and $R^4$ are the same and are each unsubstituted phenyl or phenyl substituted with up to three substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide. Preferably, any substituents present are hydrogen, $C_1$-$C_{12}$ alkyl, $C_1$-$C_{12}$ alkoxy, $C_5$-$C_{14}$ aryl, substituted $C_5$-$C_{14}$ aryl, or halide. As an example, $R^3$ and $R^4$ are mesityl (i.e. Mes as defined herein).

In certain preferred embodiments, Ru'C($R^1$)(Y—$R^2$) moiety is a substituted vinyl ether carbene or vinyl amine carbene. In other embodiments, $R^2$ is $C_{1-6}$ alkyl, preferably ethyl, propyl, or butyl. In still other embodiments, Q is —$CH_2$—$CH_2$— and $R^3$ and $R^4$ are mesityl.

In some embodiments, the metathesis catalyst is generated in situ by the reaction between a quenching agent of structure:

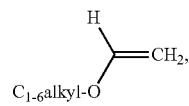

preferably

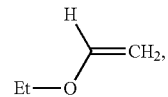

and a metathesis catalyst of structure:

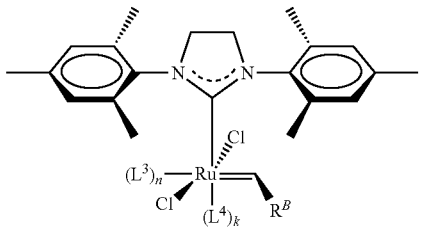

The catalytic precursors may also have a structure shown below, as applied and exemplified in the Examples

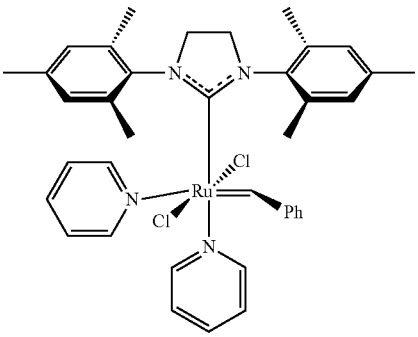

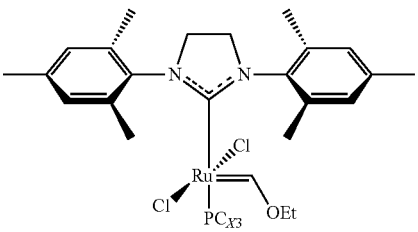

One particularly attractive series of compositions include those where the compositions contain the metathesis catalysts described above as well as added aromatic bidentate ligands,

In more specific embodiments,

is an optionally substituted phenanthroline, optionally substituted with electron-withdrawing or electron-donating groups. When such ligands are incorporated into the compositions, the catalysts are converted to compounds having structures according to Formula (II):

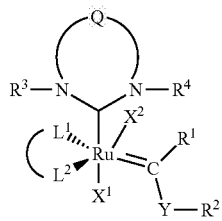

(II)

wherein:

$L^1$, $L^2$ are neutral electron donor ligands and

when taken together with the Ru to which they are bound or coordinated, form a 5, 6, or 7-membered ring.

$X^1$ and $X^2$ are anionic ligands (as generally described herein, but preferably halo (chloro));

Y is O, N—$R^1$, or S; and

Q is a two-atom linkage having the structure —$CR^{11}R^{12}$—$CR^{13}R^{14}$— or —$CR^{11}$=$CR^{13}$—, preferably —$CR^{11}R^{12}$—$CR^{13}R^{14}$—, wherein $R^{11}$, $R^{12}$, $R^{13}$, and $R^{14}$ are independently selected from hydrogen, hydrocarbyl, substituted hydrocarbyl, heteroatom-containing hydrocarbyl, substituted heteroatom-containing hydrocarbyl, and functional groups.

$R^1$, $R^2$, $R^A$, and $R^B$ are independently, as described above including hydrogen, optionally substituted hydrocarbyl, optionally substituted heteroatom-containing hydrocarbyl, functional groups, or may be linked to form a cyclic group, which may be aliphatic or aromatic, and may contain substituents and/or heteroatoms; R2 is preferably $C_{1-6}$ alkyl, more preferably ethyl, propyl, or butyl;

$R^3$ and $R^4$ are independently, as described above including optionally substituted hydrocarbyl, or optionally substituted heteroatom-containing hydrocarbyl (bulky hydrocarbyls are preferred, for example substituted phenyl or adamantyl); and wherein any two or more of $X^1$, $X^2$, $R^1$, and $R^2$ can be taken together to form one or more cyclic groups.

Alternatively, catalysts of this form may be preformed before adding to the polymerizable material matrices. Accordingly, such compounds may be generated in situ, or added as pre-formed materials. In certain embodiments within this class,

is an aromatic bidentate diamine. In more specific embodiments,

is an optionally substituted phenanthroline, optionally substituted with electron-withdrawing or electron-donating groups. Such ligands may be described generically in terms of

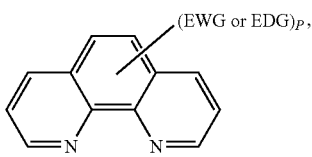

where "EWG or EDG" refers independently to Electron Withdrawing Groups or Electron Donating groups, respectively, and P is 0, 1, 2, 3, 4, 5, 6, 7, or 8, preferably 1 or 2, and the descriptor:

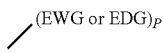

indicates that the 0, 1, 2, 3, 4, 5, 6, 7, or 8 EWG or EDG may independently replace any one or more H on the phenanthroline ring. Such EWG or EDG provide an opportunity to "tune" the reactivity of the metathesis catalyst or to improve solubility in the material matrices or both. The EWG or EDG may include, independently at each occurrence, —$NH_2$, —NHR, —$NR_2$ (where R is $C_{1-18}$ alkyl), hydroxide, $C_{1-18}$ alkoxide, —NHC(O)($C_{1-18}$ alkyl), $C_{1-18}$ alkyl, $C_{6-10}$ aryl, nitro, quaternary amines, halo- or perhalo-$C_{1-18}$ alkyl, —CN, —$C_{0-6}$ alkylsulfonate, —$C_{0-6}$ alkyl phosphonate, —$C_{1-6}$ alkyl-C(O)—R (where R is $C_{1-18}$ alkyl), or —$C_{1-6}$alkoxycarbonyls. In preferred embodiments, the EWG or EDG include, independently at each occurrence —$NH_2$, —NHR, —$NR_2$ (where R is $C_{1-3}$ alkyl), hydroxide, $C_{1-3}$ alkoxide, —NHC(O)($C_{1-3}$ alkyl), $C_{1-6}$ alkyl, $C_6$aryl, nitro, quaternary amines, $CF_3$, —CN, —$C_{1-6}$ alkylsulfonate, —$C_{0-3}$ alkyl phosphonate, -carboxylate, or —$C_{1-3}$alkoxycarbonyl.

In some embodiments, the Ru=C($R^1$)(Y—$R^2$) moiety is a substituted vinyl ether carbene. $R^2$ may be $C_{1-6}$ alkyl, preferably ethyl, propyl, or butyl.

In other cases, Q may be defined as having the structure —$CH_2$—$CH_2$— and either $R^3$ or $R^4$, or both $R^3$ and $R^4$ are phenyl groups, optionally substituted in the 2, 4, 6 positions with independent $C_{1-6}$ alkyl groups, where $C_{3-6}$ alkyl groups may be branched or linear, e.g., including methyl, ethyl, n-propyl, iso-propyl, n-butyl, sec-butyl, tert-butyl. In certain preferred embodiments, the phenyl groups are optionally substituted in the 2,6 positions with independent $C_{1-6}$ alkyl groups, and the 4-position is optionally substituted with an electron-withdrawing or -donating group as described herein, for example, alkyl, alkoxy, nitro, or halo. In other embodiments, Q is —$CH_2$—$CH_2$— and $R^3$ and $R^4$ are independently mesityl or optionally substituted adamantyl.

A particular attractive catalyst useful within this class of compositions and methods is one characterized as:

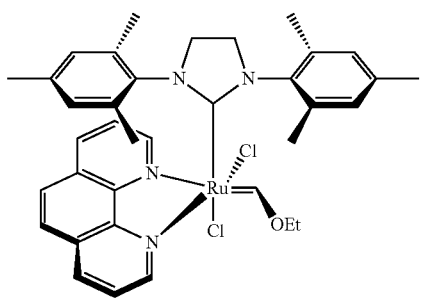

In many other cases, even compositions comprising catalysts described as having reduced metathesis activity polymerized or crosslinked highly reactive olefins (such as dicyclopentadiene, DCPD) over time even without exposure to light, or exhibited variable activity over time. By contrast, the addition of the phenanthroline ligand into the resist materials or use of phenanthroline substituted catalysts led to improved stability and processability. While resists using other ligands were found to be susceptible to thermally-activated crosslinking, films of the phenanthroline-based catalyst resist could be heated at 100° C. for many minutes and are still able to be patterned with light afterwards. Additionally, whereas early versions of the photoresist were air sensitive after long periods, resists comprising this catalyst demonstrated significantly improved air and moisture stability. A large number of functionalized olefinic monomers (including alcohols, carboxylic acids, fluorocarbons, amines, imides, quaternary ammonium ions, halogens, styrenes, phosphonates, phosphonic acids, aromatics, fluorescent molecular dyes, NHS esters, pigments such as carotene, and polypeptides) have been incorporated into the resist, further demonstrating the tolerance of this system. As well, the processing of such resists appear to be unaffected by the addition of many solvents, including water, acetonitrile and chloroform.

Photochemical Conditions

As used herein, and unless otherwise stated, the term "activates" refers to the fact that the irradiated catalyst metathesizes (i.e., polymerizes or crosslinks) olefins or alkynes at a rate that is faster at least 10 times faster than metathesizes the same olefins or alkynes before irradiation. Having said this, and when so specified, independent embodiments provide that the irradiated catalyst metathesizes olefins or alkynes at a rate that is faster at least 2 times, 5 times, 50 times, 100 times, or 1000 times faster than the metathesis of the same olefins or alkynes before or without irradiation.

It is not clear as to the detailed mechanism by which light activates the Fischer-type carbene catalysts, but it appears that the wavelength of irradiation is important. In certain embodiments, the Fischer-type carbene catalyst (at least for the Fischer-type carbene ruthenium metathesis catalyst) is irradiated with light comprising a wavelength in a range of from about 150 to about 800 nm, or in a range of from about 220 to about 440 nm, preferably in a range of from about 240 to about 260 nm, or from about 260 nm to about 340 nm, or from about 340 to about 360 nm, or a combination thereof. Additional embodiments provide that the light comprises at least one wavelength in a range of from about 150 to about 200 nm, from about 200 to about 220 nm, from about 220 to about 240 nm, from about 240 to about 260 nm, from about 260 to about 280 nm, from about 280 to about 300 nm, from about 300 to about 320 nm, from about 320 to about 340 nm, from about 340 to about 360 nm, from about 360 to about 380 nm, from about 380 to about 400 nm, from about 400 to about 500 nm, from about 500 to about 600 nm, from about 600 to about 700 nm, from about 700 to about 800 nm, or a combination thereof. In other preferred embodiments, this wavelength is in a range of from about 240 to about 260 nm or from about 340 to about 360 nm. This is consistent with currently available dry-polymer photopolymers used in the printed circuit industry (e.g. photoresist and solder mask) function when exposed to ultraviolet (UV) radiation in the range of about 300 nm to about 440 nm in a production environment.

Additional embodiments provide that the compositions may be activated by two- or three-photon energy sources.

For example, use of a focused 790 nm laser has yielded good results: three-dimensional structures have been written using this multi-photon absorption. Specifically, certain of the disclosed resists have been employed successfully in the Photonic Professional System from Nanoscribe. Other multi-photon lithography methods may also be employed, including interference lithography techniques such as phase mask lithography and proximity field nanopatterning. Other patterning strategies, including nanoimprint lithography, substrate conformal imprint lithography, stimulated emission and depletion lithography, are also methods which can be used in concert with the present compositions and methods.

Figure 5:
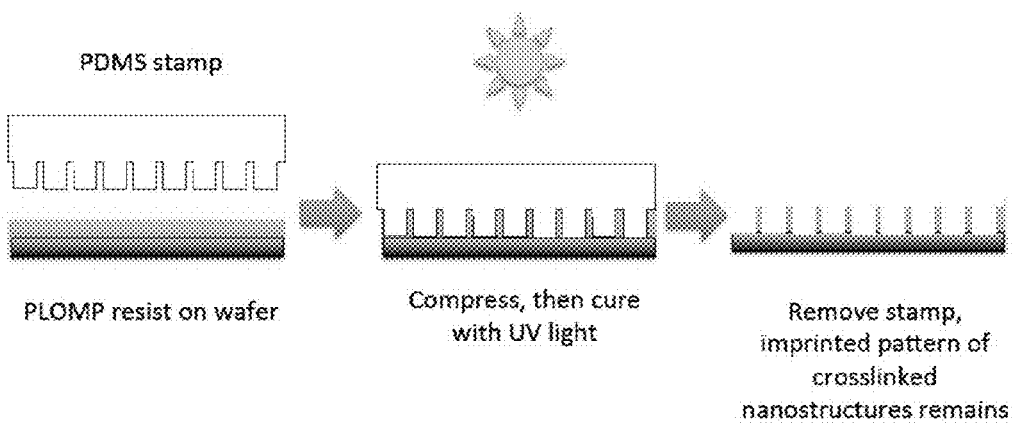
FIG. 5 illustrates the concept of nanoimprint lithography, as applied to the methods and compositions of the present disclosure.

In particular, nanoimprint lithography is a technique that is widely used to replicate nanostructured layers. This technique has the advantage that the imprinting stamp can be reused many times. The time-intensive process of making a 'master' for the stamp need only be performed once, enabling rapid duplication applicable to industrial scale micro- and nanofabrication. This method has been shown to be applicable with the present methods and compositions (see Example 16), thereby enabling the rapid and large-area fabrication of chemically functional nanostructures (see FIG. 5).

Similarly, these Fischer-type carbene ruthenium metathesis catalysts become activated after being irradiated with a light having an intensity in a range of about 2 watts to about 6000 watts, preferably in a range of from about 2 watts to about 10 watts, at least one wavelength in one of the ranges described above, for example in a range of about 220 to 440 nm. Small UV lamps are typically commercially available in range of from about 6 to about 40 watts and the catalysts described herein have been demonstrated to respond well (i.e., become activated) at these levels (see Examples). For some systems, depending on the reactivity of the specific catalyst and/or olefins, the energy of sunlight is sufficient to activate these materials. Larger UV lamps start at about 1000 watts, and commercial exposure equipment routinely provides as much as 6000 watts of irradiation from banks of high-pressure mercury arc-lamps. It is expected that the catalysts described herein will work at these levels, if necessary to go there.

Unsaturated Precursors

The methods of the present invention also consider that the Fischer-type carbene ruthenium metathesis catalyst as described herein, may be dissolved in a solvent in the presence of at least one unsaturated organic precursor or are admixed or dissolved in at least one unsaturated organic precursor. As used herein, the term "at least one unsaturated organic precursor" is intended to connote one or more molecular compound or oligomer, or combination thereof, each comprising at least one olefinic (alkene) or one acetylenic (alkyne) bond per molecule or oligomeric unit. These precursors comprise cyclic or alicyclic cis- or trans-olefins or cyclic or alicyclic acetylenes, or a structure having both types of bonds (including alicyclic or cyclic enynes).

The photosensitive, polymerizable compositions may also be described as being dissolved or admixed within polymerizable material matrix. Such matrices include those comprising polymers, polymer precursors, or a combination thereof, provided that the matrix contains at least one olefinic (alkene) or one acetylenic (alkyne) bond per molecule, oligomeric unit, or polymeric unit. Such compositions may include crosslinking polymers. In some cases, the mixture of polymerized and non-polymerized materials may result from the incomplete polymerization of the polymer precursor. In other cases, the polymerized and non-polymerized materials may be chemically unrelated.

The inventive compositions and methods may also comprise alkynyl precursors. As used herein, the term "alkynyl" (or "acetylenic") or "alkyne" refers to a linear or branched hydrocarbon group or compound of 2 to about 24 carbon atoms containing at least one triple bond, such as ethynyl, n-propynyl, and the like. Preferred alkynyl groups herein contain 2 to about 12 carbon atoms, preferably containing a terminal alkyne bond. The term "lower alkynyl" refers to an alkynyl group of 2 to 6 carbon atoms. The term "substituted alkynyl" refers to alkynyl substituted with one or more substituent groups. As used herein, the terms "optional" or "optionally" mean that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

Olefinic precursors may be used in tandem with the alkynes, either employed as part of the feedstock mixtures, or in sequential processing of the product polymers. Suitable options for such precursors are those ring systems, particularly strained ring systems, which are useful for ROMP reactions. One such class of compounds in this regard is substituted or unsubstituted cyclooctatetraenes, including cyclooctatetraene itself.

As described above, suitable options for such olefinic or acetylenic precursors include ring systems, particularly strained ring systems, which are useful for ROMP reactions. Such cyclic olefins may be optionally substituted, optionally heteroatom-containing, mono-unsaturated, di-unsaturated, or poly-unsaturated $C_5$ to $C_{24}$ hydrocarbons that may be mono-, di-, or poly-cyclic. The cyclic olefin may generally be any strained or unstrained cyclic olefin, provided the cyclic olefin is able to participate in a ROMP reaction either individually or as part of a ROMP cyclic olefin composition. While certain unstrained cyclic olefins such as cyclohexene are generally understood to not undergo ROMP reactions by themselves, under appropriate circumstances, such unstrained cyclic olefins may nonetheless be ROMP active. For example, when present as a co-monomer in a ROMP composition, unstrained cyclic olefins may be ROMP active. Accordingly, as used herein and as would be appreciated by the skilled artisan, the term "unstrained cyclic olefin" is intended to refer to those unstrained cyclic olefins that may undergo a ROMP reaction under any conditions, or in any ROMP composition, provided the unstrained cyclic olefin is ROMP active.

In general, the cyclic olefin may be represented by the structure of formula (A)

(A)

wherein J, $R^{41}$, and $R^{42}$ are as follows:

$R^{41}$ and $R^{42}$ is selected independently from the group consisting of hydrogen, hydrocarbyl (e.g., $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), and substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl) and, if substituted hydrocarbyl or substituted heteroatom-containing hydrocarbyl, wherein the substituents may be functional groups ("Fn") such as alkene, alkyne, phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group (wherein the metal may be, for example, Sn or Ge). $R^{A1}$ and $R^{A2}$ may itself be one of the aforementioned groups, such that the Fn moiety is directly bound to the olefinic carbon atom indicated in the structure. In the latter case, however, the functional group will generally not be directly bound to the olefinic carbon through a heteroatom containing one or more lone pairs of electrons, e.g., an oxygen, sulfur, nitrogen, or phosphorus atom, or through an electron-rich metal or metalloid such as Ge, Sn, As, Sb, Se, Te, etc. With such functional groups, there will normally be an intervening linkage $Z^*$, such that $R^{A1}$ and/or $R^{A2}$ then has the structure —$(Z^*)_n$-Fn wherein n is 1, Fn is the functional group, and $Z^*$ is a hydrocarbylene linking group such as an alkylene, substituted alkylene, heteroalkylene, substituted heteroalkene, arylene, substituted arylene, heteroarylene, or substituted heteroarylene linkage.

J is a saturated or unsaturated hydrocarbylene, substituted hydrocarbylene, heteroatom-containing hydrocarbylene, or substituted heteroatom-containing hydrocarbylene linkage, wherein when J is substituted hydrocarbylene or substituted heteroatom-containing hydrocarbylene, the substituents may include one or more —$(Z^*)_n$-Fn groups, wherein n is zero or 1, and Fn and $Z^*$ are as defined previously. Additionally, two or more substituents attached to ring carbon (or other) atoms within J may be linked to form a bicyclic or polycyclic olefin. J will generally contain in the range of approximately 5 to 14 ring atoms, typically 5 to 8 ring atoms, for a monocyclic olefin, and, for bicyclic and polycyclic olefins, each ring will generally contain 4 to 8, typically 5 to 7, ring atoms.

Mono-unsaturated cyclic olefins encompassed by structure (A) may be represented by the structure (B)

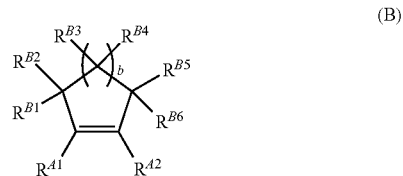

(B)

wherein b is an integer generally although not necessarily in the range of 1 to 10, typically 1 to 5, $R^{A1}$ and $R^{A2}$ are as defined above for structure (A), and $R^{B1}$, $R^{B2}$, $R^{B3}$, $R^{B4}$, $R^{B5}$, and $R^{B6}$ are independently selected from the group consisting of hydrogen, hydrocarbyl, substituted hydrocarbyl, heteroatom-containing hydrocarbyl, substituted heteroatom-containing hydrocarbyl and —$(Z^*)_n$-Fn where n, $Z^*$ and Fn are as defined previously, and wherein if any of the $R^{B1}$ through $R^{B6}$ moieties is substituted hydrocarbyl or substituted heteroatom-containing hydrocarbyl, the substituents may include one or more —$(Z^*)_n$-Fn groups. Accordingly, $R^{B1}$, $R^{B2}$, $R^{B3}$, $R^{B4}$, $R^{B5}$, and $R^{B6}$ may be, for example, hydrogen, hydroxyl, $C_1$-$C_{20}$ alkyl, $C_5$-$C_{20}$ aryl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, amino, amido, nitro, etc.

Furthermore, any of the $R^{B1}$, $R^{B2}$, $R^{B3}$, $R^{B4}$, $R^{B5}$, and $R^{B6}$ moieties can be linked to any of the other $R^{B1}$, $R^{B2}$, $R^{B3}$, $R^{B4}$, $R^{B5}$, and $R^{B6}$ moieties to provide a substituted or unsubstituted alicyclic group containing 4 to 30 ring carbon atoms or a substituted or unsubstituted aryl group containing 6 to 18 ring carbon atoms or combinations thereof and the linkage may include heteroatoms or functional groups, e.g. the linkage may include without limitation an ether, ester, thioether, amino, alkylamino, imino, or anhydride moiety. The alicyclic group can be monocyclic, bicyclic, or polycyclic. When unsaturated the cyclic group can contain monounsaturation or multiunsaturation, with monounsaturated cyclic groups being preferred. When substituted, the rings contain monosubstitution or multisubstitution wherein the substituents are independently selected from hydrogen, hydrocarbyl, substituted hydrocarbyl, heteroatom-containing hydrocarbyl, substituted heteroatom-containing hydrocarbyl, —$(Z^*)_n$-Fn where n is zero or 1, $Z^*$ and Fn are as defined previously, and functional groups (Fn) provided above.

Examples of mono-unsaturated, monocyclic olefins encompassed by structure (B) include, without limitation, cyclopentene, cyclohexene, cycloheptene, cyclooctene, cyclononene, cyclodecene, cycloundecene, cyclododecene, tricyclodecene, tetracyclodecene, octacyclodecene, and cycloeicosene, and substituted versions thereof such as 1-methylcyclopentene, 1-ethylcyclopentene, 1-isopropylcyclohexene, 1-chloropentene, 1-fluorocyclopentene, 4-methylcyclopentene, 4-methoxy-cyclopentene, 4-ethoxy-cyclopentene, cyclopent-3-ene-thiol, cyclopent-3-ene, 4-methylsulfanyl-cyclopentene, 3-methylcyclohexene, 1-methylcyclooctene, 1,5-dimethylcyclooctene, etc.

Monocyclic diene reactants encompassed by structure (A) may be generally represented by the structure (C)

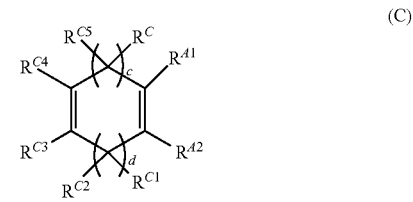

(C)

wherein c and d are independently integers in the range of 1 to about 8, typically 2 to 4, preferably 2 (such that the reactant is a cyclooctadiene), $R^{A1}$ and $R^{A2}$ are as defined above for structure (A), and $R^{C1}$, $R^{C2}$, $R^{C3}$, $R^{C4}$, $R^{C5}$, and $R^{C6}$ are defined as for $R^{B1}$ through $R^{B6}$. In this case, it is preferred that $R^{C3}$ and $R^{C4}$ be non-hydrogen substituents, in which case the second olefinic moiety is tetrasubstituted. Examples of monocyclic diene reactants include, without limitation, 1,3-cyclopentadiene, 1,3-cyclohexadiene, 1,4-cyclohexadiene, 5-ethyl-1,3-cyclohexadiene, 1,3-cycloheptadiene, cyclohexadiene, 1,5-cyclooctadiene, 1,3-cyclooctadiene, and substituted analogs thereof. Triene reactants are analogous to the diene structure (C), and will generally contain at least one methylene linkage between any two olefinic segments. Bicyclic and polycyclic olefins encompassed by structure (A) may be generally represented by the structure (D)

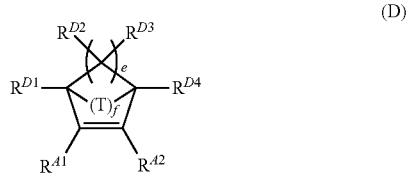

(D)

wherein $R^{A1}$ and $R^{A2}$ are as defined above for structure (A), $R^{D1}$, $R^{D2}$, $R^{D3}$, and $R^{D4}$ are as defined for $R^{B1}$ through $R^{B6}$, e is an integer in the range of 1 to 8 (typically 2 to 4) f is generally 1 or 2; T is lower alkylene or alkenylene (generally substituted or unsubstituted methyl or ethyl), $CHR^{G1}$, $C(R^{G1})_2$, O, S, N—$R^{G1}$, P—$R^{G1}$, O=P—$R^{G1}$, $Si(R^{G1})_2$, B—$R^{G1}$, or As—$R^{G1}$ where $R^{G1}$ is alkyl, alkenyl, cycloalkyl, cycloalkenyl, aryl, alkaryl, aralkyl, or alkoxy. Furthermore, any of the $R^{D1}$, $R^{D2}$, $R^{D3}$, and $R^{D4}$ moieties can be linked to any of the other $R^{D1}$, $R^{D2}$, $R^{D3}$, and $R^{D4}$ moieties to provide a substituted or unsubstituted alicyclic group containing 4 to 30 ring carbon atoms or a substituted or unsubstituted aryl group containing 6 to 18 ring carbon atoms or combinations thereof and the linkage may include heteroatoms or functional groups, e.g. the linkage may include without limitation an ether, ester, thioether, amino, alkylamino, imino, or anhydride moiety. The cyclic group can be monocyclic, bicyclic, or polycyclic. When unsaturated the cyclic group can contain mono-unsaturation or multi-unsaturation, with mono-unsaturated cyclic groups being preferred. When substituted, the rings contain monosubstitution or multisubstitution wherein the substituents are independently selected from hydrogen, hydrocarbyl, substituted hydrocarbyl, heteroatom-containing hydrocarbyl, substituted heteroatom-containing hydrocarbyl, —$(Z^*)_n$-Fn where n is zero or 1, $Z^*$ and Fn are as defined previously, and functional groups (Fn) provided above.

Cyclic olefins encompassed by structure (D) are in the norbornene family. As used herein, norbornene means any compound that includes at least one norbornene or substituted norbornene moiety, including without limitation norbornene, substituted norbornene(s), norbornadiene, substituted norbornadiene(s), polycyclic norbornenes, and substituted polycyclic norbornene(s). Norbornenes within this group may be generally represented by the structure (E)

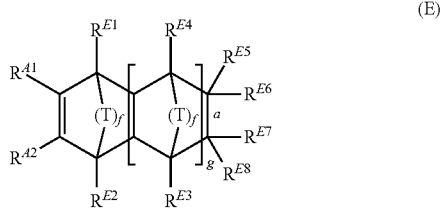

(E)

wherein $R^{A1}$ and $R^{A2}$ are as defined above for structure (A), T is as defined above for structure (D), $R^{E1}$, $R^{E2}$, $R^{E3}$, $R^{E4}$, $R^{E5}$, $R^{E6}$, $R^{E7}$, and $R^{E8}$ are as defined for $R^{B1}$ through $R^{B6}$, and "a" represents a single bond or a double bond, f is generally 1 or 2, "g" is an integer from 0 to 5, and when "a" is a double bond one of $R^{E5}$, $R^{E6}$ and one of $R^{E7}$, $R^{E8}$ is not present. Furthermore, any of the $R^{E5}$, $R^{E6}$, $R^{E7}$, and $R^{E8}$ moieties can be linked to any of the other $R^{E5}$, $R^{E6}$, $R^{E7}$, and $R^{E8}$ moieties to provide a substituted or unsubstituted alicyclic group containing 4 to 30 ring carbon atoms or a substituted or unsubstituted aryl group containing 6 to 18 ring carbon atoms or combinations thereof and the linkage may include heteroatoms or functional groups, e.g. the linkage may include without limitation an ether, ester, thioether, amino, alkylamino, imino, or anhydride moiety. The cyclic group can be monocyclic, bicyclic, or polycyclic. When unsaturated the cyclic group can contain monounsaturation or multiunsaturation, with monounsaturated cyclic groups being preferred. When substituted, the rings contain monosubstitution or multisubstitution wherein the substituents are independently selected from hydrogen, hydrocarbyl, substituted hydrocarbyl, heteroatom-containing hydrocarbyl, substituted heteroatom-containing hydrocarbyl, —$(Z^*)_n$-Fn where n is zero or 1, $Z^*$ and Fn are as defined previously, and functional groups (Fn) provided above.

More preferred cyclic olefins possessing at least one norbornene moiety have the structure (F):

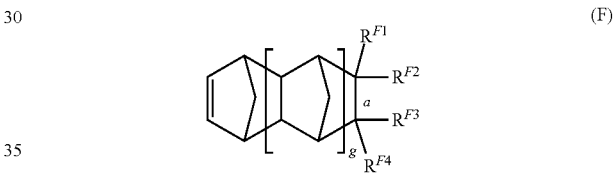

(F)

wherein, $R^{F1}$, $R^{F2}$, $R^{F3}$, and $R^{F4}$, are as defined for $R^{B1}$ through $R^{B6}$, and "a" represents a single bond or a double bond, "g" is an integer from 0 to 5, and when "a" is a double bond one of $R^{F1}$, $R^{F2}$ and one of $R^{F3}$, $R^{F4}$ is not present.

Furthermore, any of the $R^{F1}$, $R^{F2}$, $R^{F3}$, and $R^{F4}$ moieties can be linked to any of the other $R^{F1}$, $R^{F2}$, $R^{F3}$, and $R^{F4}$ moieties to provide a substituted or unsubstituted alicyclic group containing 4 to 30 ring carbon atoms or a substituted or unsubstituted aryl group containing 6 to 18 ring carbon atoms or combinations thereof and the linkage may include heteroatoms or functional groups, e.g. the linkage may include without limitation an ether, ester, thioether, amino, alkylamino, imino, or anhydride moiety. The alicyclic group can be monocyclic, bicyclic, or polycyclic. When unsaturated the cyclic group can contain monounsaturation or multiunsaturation, with monounsaturated cyclic groups being preferred. When substituted, the rings contain monosubstitution or multisubstitution wherein the substituents are independently selected from hydrogen, hydrocarbyl, substituted hydrocarbyl, heteroatom-containing hydrocarbyl, substituted heteroatom-containing hydrocarbyl, —$(Z^*)_n$-Fn where n is zero or 1, $Z^*$ and Fn are as defined previously, and functional groups (Fn) provided above.

One route for the preparation of hydrocarbyl substituted and functionally substituted norbornenes employs the Diels-Alder cycloaddition reaction in which cyclopentadiene or substituted cyclopentadiene is reacted with a suitable dienophile at elevated temperatures to form the substituted norbornene adduct generally shown by the following reaction Scheme 1:

SCHEME 1

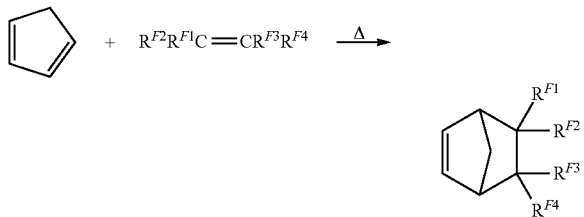

wherein $R^{F1}$ to $R^{F4}$ are as previously defined for structure (F).

Other norbornene adducts can be prepared by the thermal pyrolysis of dicyclopentadiene in the presence of a suitable dienophile. The reaction proceeds by the initial pyrolysis of dicyclopentadiene to cyclopentadiene followed by the Diels-Alder cycloaddition of cyclopentadiene and the dienophile to give the adduct shown below in Scheme 2:

SCHEME 2

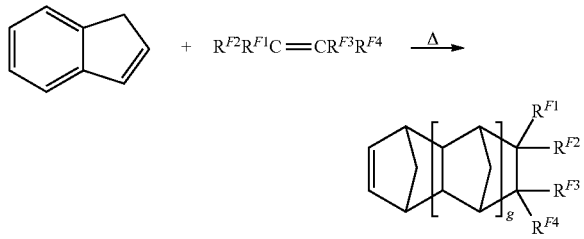

wherein "g" is an integer from 0 to 5, and $R^{F1}$ to $R^{F4}$ are as previously defined for structure (F).

Norbornadiene and higher Diels-Alder adducts thereof similarly can be prepared by the thermal reaction of cyclopentadiene and dicyclopentadiene in the presence of an acetylenic reactant as shown below in Scheme 3:

SCHEME 3

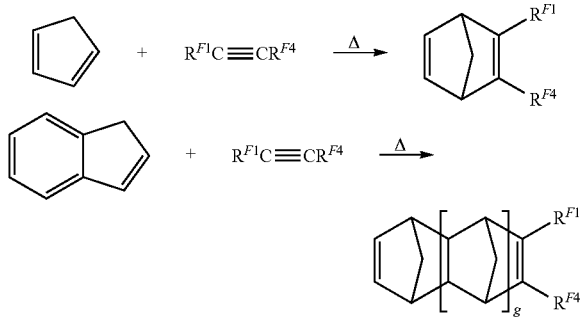

wherein "g" is an integer from 0 to 5, $R^{F1}$ and $R^{F4}$ are as previously defined for structure (F) Examples of bicyclic and polycyclic olefins thus include, without limitation, dicyclopentadiene (DCPD); trimer and other higher order oligomers of cyclopentadiene including without limitation tricyclopentadiene (cyclopentadiene trimer), cyclopentadiene tetramer, and cyclopentadiene pentamer; ethylidenenorbornene; dicyclohexadiene; norbornene; 5-methyl-2-norbornene; 5-ethyl-2-norbornene; 5-isobutyl-2-norbornene; 5,6-dimethyl-2-norbornene; 5-phenylnorbornene; 5-benzylnorbornene; 5-acetylnorbornene; 5-methoxycarbonylnorbornene; 5-ethyoxycarbonyl-1-norbornene; 5-methyl-5-methoxy-carbonylnorbornene; 5-cyanonorbornene; 5,5,6-trimethyl-2-norbornene; cyclo-hexenylnorbornene; endo, exo-5,6-dimethoxynorbornene; endo, endo-5,6-dimethoxynorbornene; endo, exo-5,6-dimethoxycarbonylnorbornene; endo,endo-5,6-dimethoxycarbonylnorbornene; 2,3-dimethoxynorbornene; norbornadiene; tricycloundecene; tetracyclododecene; 8-methyltetracyclododecene; 8-ethyltetracyclododecene; 8-methoxycarbonyltetracyclododecene; 8-methyl-8-tetracyclododecene; 8-cyanotetracyclododecene; pentacyclopentadecene; pentacyclohexadecene; and the like, and their structural isomers, stereoisomers, and mixtures thereof. Additional examples of bicyclic and polycyclic olefins include, without limitation, $C_2$-$C_{12}$ hydrocarbyl substituted norbornenes such as 5-butyl-2-norbornene, 5-hexyl-2-norbornene, 5-octyl-2-norbornene, 5-decyl-2-norbornene, 5-dodecyl-2-norbornene, 5-vinyl-2-norbornene, 5-ethylidene-2-norbornene, 5-isopropenyl-2-norbornene, 5-propenyl-2-norbornene, and 5-butenyl-2-norbornene, and the like.

Preferred cyclic olefins include $C_5$ to $C_{24}$ unsaturated hydrocarbons. Also preferred are $C_5$ to $C_{24}$ cyclic hydrocarbons that contain one or more (typically 2 to 12) heteroatoms such as O, N, S, or P. For example, crown ether cyclic olefins may include numerous O heteroatoms throughout the cycle, and these are within the scope of the invention. In addition, preferred cyclic olefins are $C_5$ to $C_{24}$ hydrocarbons that contain one or more (typically 2 or 3) olefins. For example, the cyclic olefin may be mono-, di-, or tri-unsaturated. Examples of cyclic olefins include without limitation cyclooctene, cyclododecene, and (c,t,t)-1,5,9-cyclododecatriene.

The cyclic olefins may also comprise multiple (typically 2 or 3) rings. For example, the cyclic olefin may be mono-, di-, or tri-cyclic. When the cyclic olefin comprises more than one ring, the rings may or may not be fused. Preferred examples of cyclic olefins that comprise multiple rings include norbornene, dicyclopentadiene, tricyclopentadiene, and 5-ethylidene-2-norbornene.

The cyclic olefin may also be substituted, for example, a $C_5$ to $C_{24}$ cyclic hydrocarbon wherein one or more (typically 2, 3, 4, or 5) of the hydrogens are replaced with non-hydrogen substituents. Suitable non-hydrogen substituents may be chosen from the substituents described hereinabove. For example, functionalized cyclic olefins, i.e., $C_5$ to $C_{24}$ cyclic hydrocarbons wherein one or more (typically 2, 3, 4, or 5) of the hydrogens are replaced with functional groups, are within the scope of the invention. Suitable functional groups may be chosen from the functional groups described hereinabove. For example, a cyclic olefin functionalized with an alcohol group may be used to prepare a telechelic polymer comprising pendent alcohol groups. Functional groups on the cyclic olefin may be protected in cases where the functional group interferes with the metathesis catalyst, and any of the protecting groups commonly used in the art may be employed. Acceptable protecting groups may be found, for example, in Greene et al., Protective Groups in Organic Synthesis, 3rd Ed. (New York: Wiley, 1999). A non-limiting list of protecting groups includes: (for alcohols) acetyl, benzoyl, benzyl, β-Methoxyethoxymethyl ether (MEM), Dimethoxytrityl, [bis-(4-methoxyphenyl)phenylmethyl] (DMT), methoxymethyl ether (MOM), methoxytrityl [(4-methoxyphenyl)diphenylmethyl, MMT), p-methoxybenzyl ether (PMB), methylthiomethyl ether, pivaloyl (Piv), tetrahydropyranyl (THP), tetrahydrofuran (THF), trityl (triphenylmethyl, Tr), silyl ethers (most popular ones include trimethylsilyl (TMS), tert-butyldimethylsilyl (TBDMS), triisopropylsilyloxymethyl (TOM), and triisopropylsilyl (TIPS) ethers, (for amines) tert-butyloxycarbonyl glycine, carbobenzyloxy (Cbz) group, p-methoxybenzyl carbonyl (Moz or MeOZ) group, tert-butyloxycarbonyl (BOC) group, 9-fluorenylmethyloxycarbonyl (FMOC) group, acetyl (Ac) group, benzoyl (Bz) group, benzyl (Bn), carbamate group, p-methoxybenzyl (PMB), 3,4-dimethoxybenzyl (DMPM), p-methoxyphenyl (PMP) group, tosyl (Ts) group, (for carbonyls) acetals and ketals, acylals, dithianes, (for carboxylic acids) methyl esters, benzyl esters, tert-butyl esters, esters of 2,6-disubstituted phenols (e.g. 2,6-dimethylphenol, 2,6-diisopropylphenol, 2,6-di-tert-butylphenol), silyl esters, orthoesters, oxazoline, (for phosphate) 2-cyanoethyl, and methyl. In the specific case of arginine (Arg) side chains, protection is important because of the propensity of the basic quanidinium group to produce side reactions. In cases described herein, effective protective groups include 2,2,5,7,8-pentamethylchroman (Pmc), 2,2,4,6,7-pentamethyldihydrobenzofurane (Pbf) and 1,2-dimethylindole-3-sulfonyl (MIS) groups.

Examples of functionalized cyclic olefins include without limitation 2-hydroxymethyl-5-norbornene, 2-[(2-hydroxyethyl)carboxylate]-5-norbornene, cydecanol, 5-n-hexyl-2-norbornene, 5-n-butyl-2-norbornene.

Cyclic olefins incorporating any combination of the abovementioned features (i.e., heteroatoms, substituents, multiple olefins, multiple rings) are suitable for the methods disclosed herein. Additionally, cyclic olefins incorporating any combination of the abovementioned features (i.e., heteroatoms, substituents, multiple olefins, multiple rings) are suitable for the invention disclosed herein.

The cyclic olefins useful in the methods disclosed herein may be strained or unstrained. It will be appreciated that the amount of ring strain varies for each cyclic olefin compound, and depends upon a number of factors including the size of the ring, the presence and identity of substituents, and the presence of multiple rings. Ring strain is one factor in determining the reactivity of a molecule towards ring-opening olefin metathesis reactions. Highly strained cyclic olefins, such as certain bicyclic compounds, readily undergo ring opening reactions with olefin metathesis catalysts. Less strained cyclic olefins, such as certain unsubstituted hydrocarbon monocyclic olefins, are generally less reactive. In some cases, ring opening reactions of relatively unstrained (and therefore relatively unreactive) cyclic olefins may become possible when performed in the presence of the olefinic compounds disclosed herein.

A plurality of cyclic olefins may be used with the present invention to prepare metathesis polymers. For example, two cyclic olefins selected from the cyclic olefins described hereinabove may be employed in order to form metathesis products that incorporate both cyclic olefins. Where two or more cyclic olefins are used, one example of a second cyclic olefin is a cyclic alkenol, i.e., a $C_5$-$C_{24}$ cyclic hydrocarbon wherein at least one of the hydrogen substituents is replaced with an alcohol or protected alcohol moiety to yield a functionalized cyclic olefin.

The use of a plurality of cyclic olefins, and in particular when at least one of the cyclic olefins is functionalized, allows for further control over the positioning of functional groups within the products. For example, the density of cross-linking points can be controlled in polymers and macromonomers prepared using the methods disclosed herein. Control over the quantity and density of substituents and functional groups also allows for control over the physical properties (e.g., melting point, tensile strength, glass transition temperature, etc.) of the products. Control over these and other properties is possible for reactions using only a single cyclic olefin, but it will be appreciated that the use of a plurality of cyclic olefins further enhances the range of possible metathesis products and polymers formed.

More preferred cyclic olefins include dicyclopentadiene; tricyclopentadiene; dicyclohexadiene; norbornene; 5-methyl-2-norbornene; 5-ethyl-2-norbornene; 5-isobutyl-2-norbornene; 5,6-dimethyl-2-norbornene; 5-phenylnorbornene; 5-benzylnorbornene; 5-acetylnorbornene; 5-methoxycarbonylnorbornene; 5-ethoxycarbonyl-1-norbornene; 5-methyl-5-methoxy-carbonylnorbornene; 5-cyanonorbornene; 5,5,6-trimethyl-2-norbornene; cyclo-hexenylnorbornene; endo, exo-5,6-dimethoxynorbornene; endo, endo-5,6-dimethoxynorbornene; endo, exo-5-6-dimethoxycarbonylnorbornene; endo, endo-5,6-dimethoxycarbonylnorbornene; 2,3-dimethoxynorbornene; norbornadiene; tricyclooundecene; tetracyclododecene; 8-methyltetracyclododecene; 8-ethyl-tetracyclododecene; 8-methoxycarbonyltetracyclododecene; 8-methyl-8-tetracyclo-dodecene; 8-cyanotetracyclododecene; pentacyclopentadecene; pentacyclohexadecene; higher order oligomers of cyclopentadiene such as cyclopentadiene tetramer, cyclopentadiene pentamer, and the like; and $C_2$-$C_{12}$ hydrocarbyl substituted norbornenes such as 5-butyl-2-norbornene; 5-hexyl-2-norbornene; 5-octyl-2-norbornene; 5-decyl-2-norbornene; 5-dodecyl-2-norbornene; 5-vinyl-2-norbornene; 5-ethylidene-2-norbornene; 5-isopropenyl-2-norbornene; 5-propenyl-2-norbornene; and 5-butenyl-2-norbornene, and the like. Even more preferred cyclic olefins include dicyclopentadiene, tricyclopentadiene, and higher order oligomers of cyclopentadiene, such as cyclopentadiene tetramer, cyclopentadiene pentamer, and the like, tetracyclododecene, norbornene, and $C_2$-$C_{12}$ hydrocarbyl substituted norbornenes, such as 5-butyl-2-norbornene, 5-hexyl-2-norbornene, 5-octyl-2-norbornene, 5-decyl-2-norbornene, 5-dodecyl-2-norbornene, 5-vinyl-2-norbornene, 5-ethylidene-2-norbornene, 5-isopropenyl-2-norbornene, 5-propenyl-2-norbornene, 5-butenyl-2-norbornene, and the like.

In certain embodiments, each of these Structures A-F may further comprise pendant substituents that are capable of crosslinking with one another or added crosslinking agents. For example, $R^{A1}$, $R^{A2}$, $R^{B1}$, $R^{B2}$, $R^{B3}$, $R^{B4}$, $R^{B5}$, $R^{B6}$, $R^{C1}$, $R^{C2}$, $R^{C3}$, $R^{C4}$, $R^{C5}$, $R^{C6}$, $R^{D1}$, $R^{D2}$, $R^{D3}$, $R^{D4}$, $R^{E1}$, $R^{E2}$, $R^{E3}$, $R^{E4}$, $R^{E5}$, $R^{E6}$, $R^{E7}$, $R^{E8}$, $R^{F1}$, $R^{F2}$, $R^{F3}$, and $R^{F4}$ may independently represent pendant hydrocarbyl chains containing olefinic or acetylenic bonds capable of crosslinking with themselves or other unsaturated moieties under metathesis conditions. Additionally, within Structures A-F, at least one pair of substituents, $R^{B1}$ and $R^{B2}$, $R^{B3}$ and $R^{B4}$, and $R^{B5}$ and $R^{B6}$, $R^{C1}$ and $R^{C2}$, $R^{C5}$ and $R^{C6}$, $R^{D2}$ and $R^{D3}$, $R^{E5}$ and $R^{E6}$, $R^{E7}$ and $R^{E8}$, $R^{F1}$ and $R^{F2}$, and $R^{F3}$ and $R^{F4}$, can together form an optionally substituted exocyclic double bond, for example/=CH($C_{1-6}$-Fn). This concept is specifically exemplified in the Examples, where a compound of Structure (F), where a is a single bond, g is 0, $R^{F1}$=$R^{F2}$=H and $R^{F3}$ and $R^{F4}$ together form/=CH(ethyl) is reacted with oligomers of cyclooctadiene.

When considering alternative olefinic precursors in the present methods, more preferred precursors may be those which, when incorporated into polyacetylene polymers or copolymers, modify the electrical or physical character of the resulting polymer. One general class of such precursors are substituted annulenes and annulynes, for example [18]annulene-1,4;7,10;13,16-trisulfide. When co-polymerized with acetylene, this precursor can form a block co-polymer as shown here:

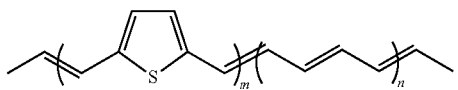

Substituted analogs of these trisulfides, as described below can also be used to provide corresponding substituted poly(thienylvinylene)-containing polymers or copolymers. For example, the 2,3,8,9,14,15-hexaoctyl derivative of [18]annulene-1,4;7,10;13,16-trisulfide is described in Horie, et al., "Poly(thienylvinylene) prepared by ring-opening metathesis polymerization: Performance as a donor in bulk heterojunction organic photovoltaic devices," *Polymer* 51 (2010) 1541-1547, which is incorporated by reference herein for all purposes

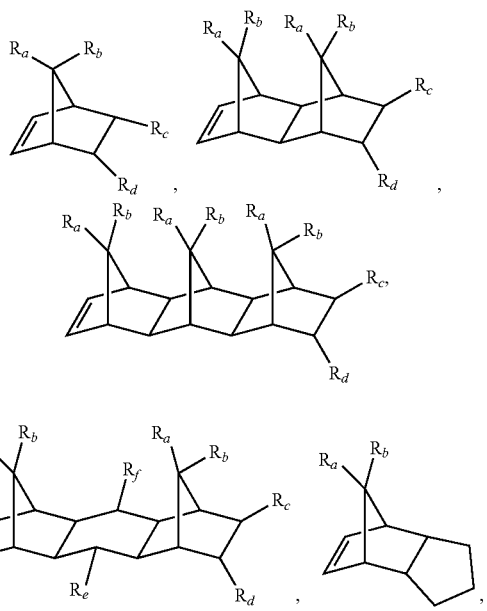

R = Octyl

In certain embodiments, the unsaturated organic precursor comprises a purely hydrocarbon compound having a structure:

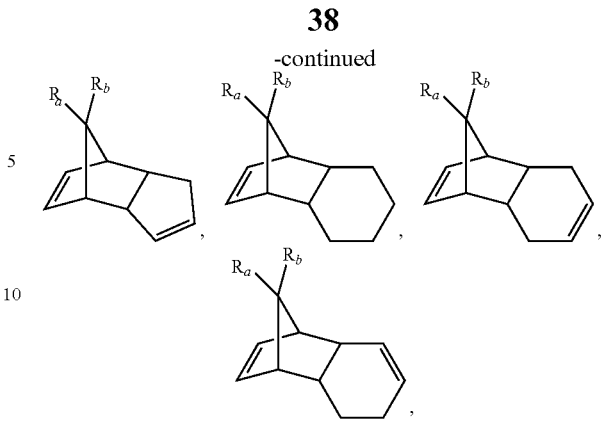

or a mixture thereof, wherein Ra, $R_b$, $R_c$, $R_d$, $R_e$, and $R_f$ are independently H or alkyl (preferably $C_{1-20}$ alkyl, more preferably $C_{1-10}$ alkyl).

The unsaturated organic precursor may also comprise a hydrocarbon compound having a dicyclopentadiene structure, for example:

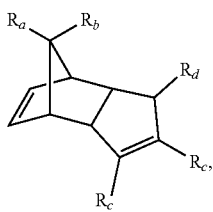

wherein Ra, $R_b$, $R_c$, $R_d$, $R_e$, and $R_f$ are independently H or alkyl (preferably $C_{1-20}$ alkyl, more preferably $C_{1-10}$ alkyl). One such polymer resulting from such precursors comprises units having a structure:

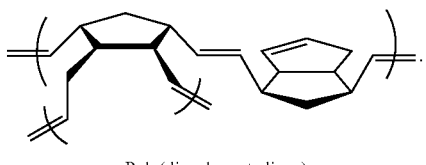

Poly(dicyclopentadiene)

Figure 3A:
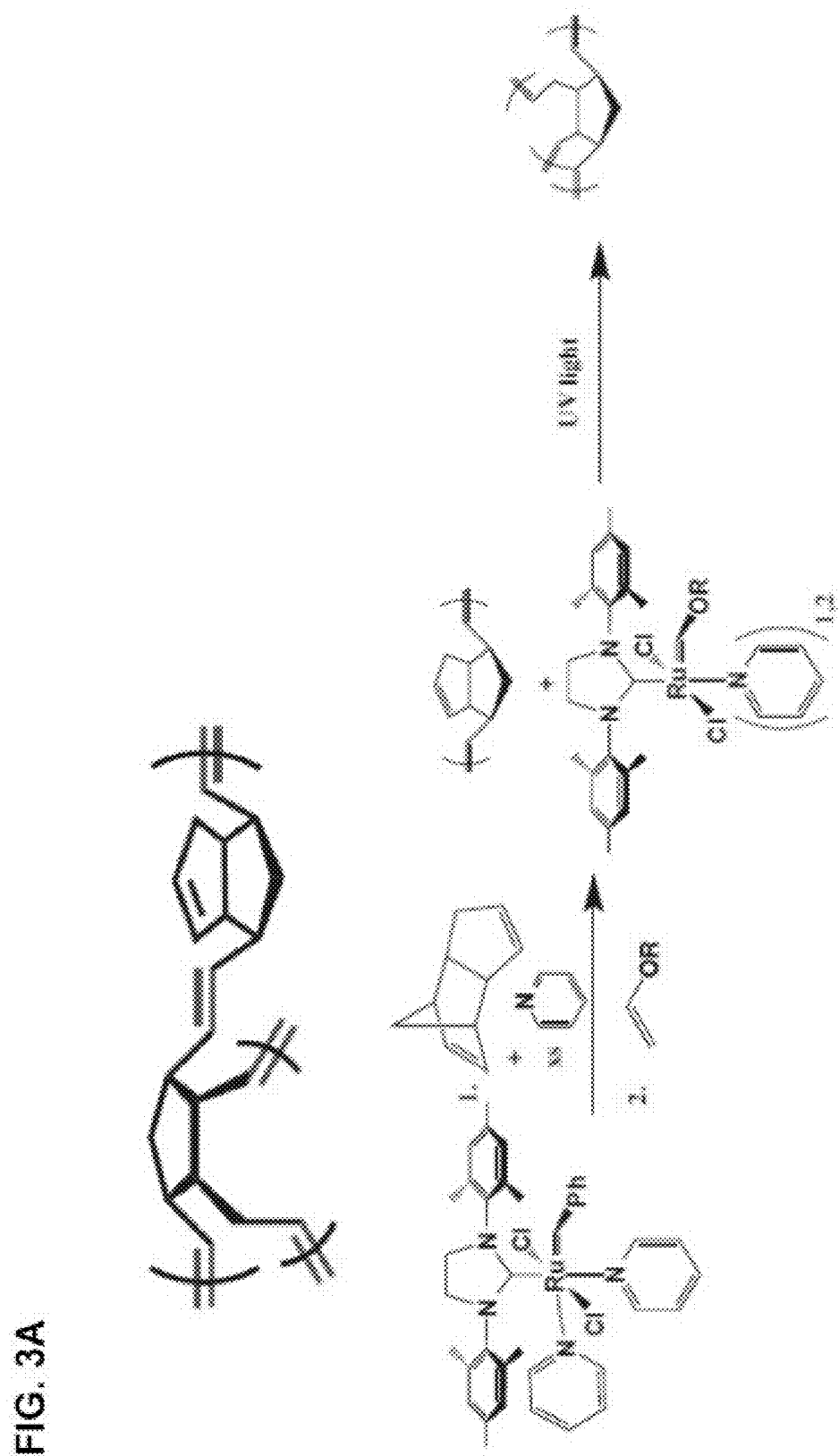

See FIG. 3A.

These hydrocarbon precursors are particularly attractive, for example, when the final polymerized product or article derived therefrom is to be subject to aggressive chemical conditions. For example, patterned products or article derived therefrom prepared from dicyclopentadiene structures are particularly effective in resisting aqueous HF, making them particularly attractive for use as etching masks in semi-conductor or other electronic processing. It is believe that the term "resistant to aqueous HF" carries a practical connotation understood by those skilled in the art; i.e., the patterned polymer layer is sufficiently robust as to withstand HF (or to slow the diffusion of fluoride ions from the protected surface) for a time sufficient to be practically useful in etch-processing or the polymer layer is not dissolved to a meaningful extent or the crosslinked polymer matrix is able to slow the diffusion of the HF (and fluoride ions) to protect the surface from these reactive species. Aqueous HF itself may be also characterized by its concentration, and in various embodiments, the concentration may be 5, 10, 15, 20, 25, 30, 35, 40, 45, or 48 wt %. For examples, in experiments using such compositions of the present disclosure, it was possible to selectively etch 30 micron posts in silicon dioxide (glass) in less than minute. Unless otherwise stated, the term "resistant to aqueous HF" is defined as being able to withstand exposure to aqueous HF at room temperatures (i.e., ca. 20-25° C.) for a period of 1 hour without measurable peeling from the substrate. Where specified, the term may also be defined in this way in terms of longer (e.g., 2, 3, 4, 5, 6, 12, 24, 48, or 96 hours) or shorter (e.g., 1, 5, 10, 20, 30, 40, or 50 minutes) exposure times. Such materials are also extremely tough and durable, and may be used in applications in bullet-proof vests and carbon fiber composites (e.g., as used in wind turbine blades)

Figure 4:
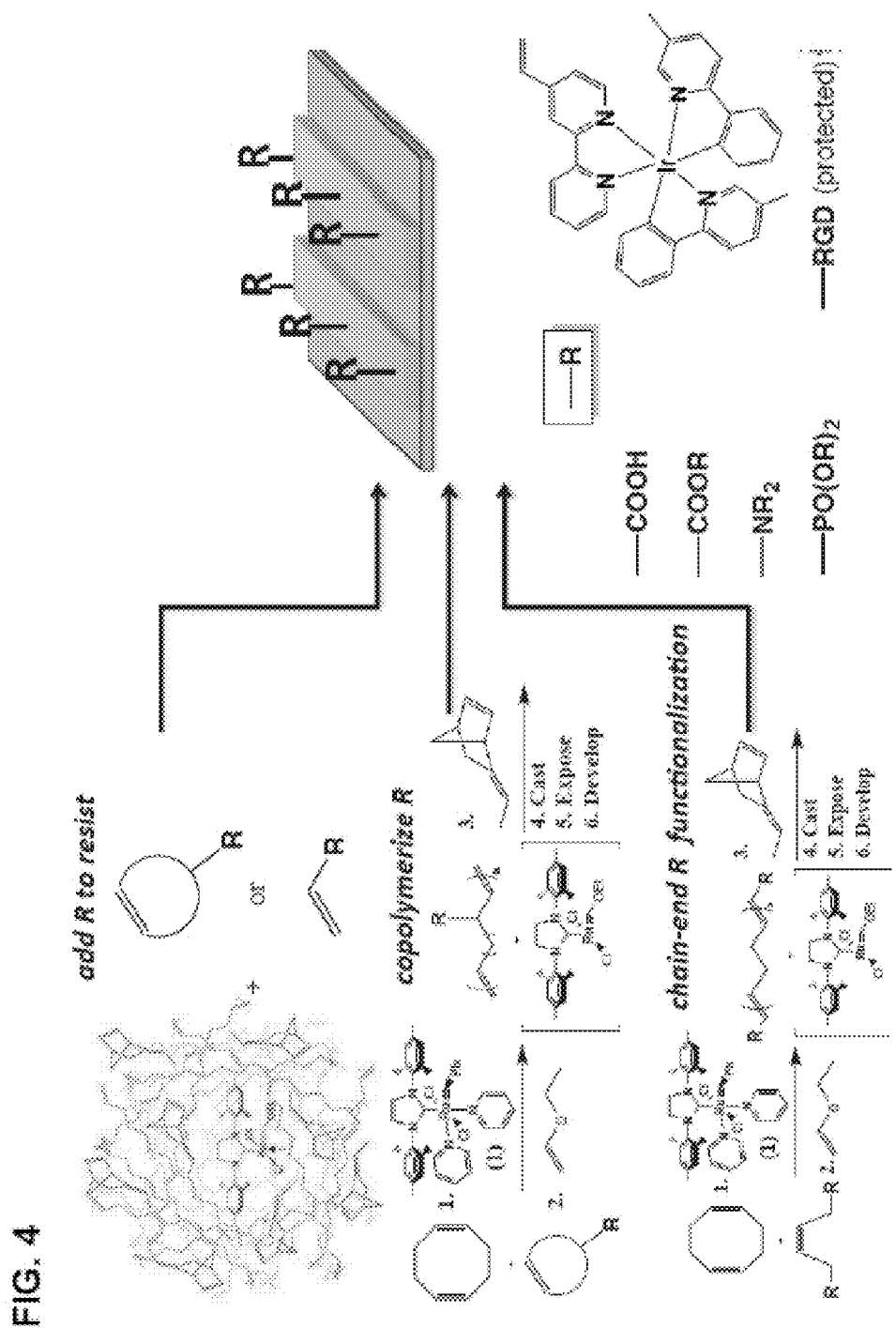
FIG. 4 illustrates several embodiments of the present disclosure.

In other embodiments, the unsaturated polymerizable material matrix may include mono-, di-, or polyfunctionalized cyclic or alicyclic alkenes or alkynes; i.e., which include functional groups, including for example, alcohols, amines, amides, carboxylic acids and esters, phosphines, phosphonates, sulfonates or the like. See, e.g., FIG. 4, Examples 9 through 12. Good results have been achieved using optionally substituted bicyclo[2.2.1]hept-5-ene-2,3,dicarboxylic acid diesters, 7-oxa-bicyclo[2.2.1]hept-5-ene-2,3,dicarboxylic acid diesters, 4-oxa-tricyclo[5.2.1.0$^{2,6}$]dec-8-ene-3,5-diones, 4,10-dioxa-tricyclo[5.2.1.0$^{2,6}$]dec-8-ene-3,5-diones, 4-aza-tricyclo[5.2.1.0$^{2,6}$]dec-8-ene-3,5-diones, 10-oxa-4-aza-tricyclo[5.2.1.0$^{2,6}$]dec-8-ene-3,5-diones, or simple di-substituted alkenes, including bisphosphines. In certain embodiments, these functionalized alkenes include those having structures such as:

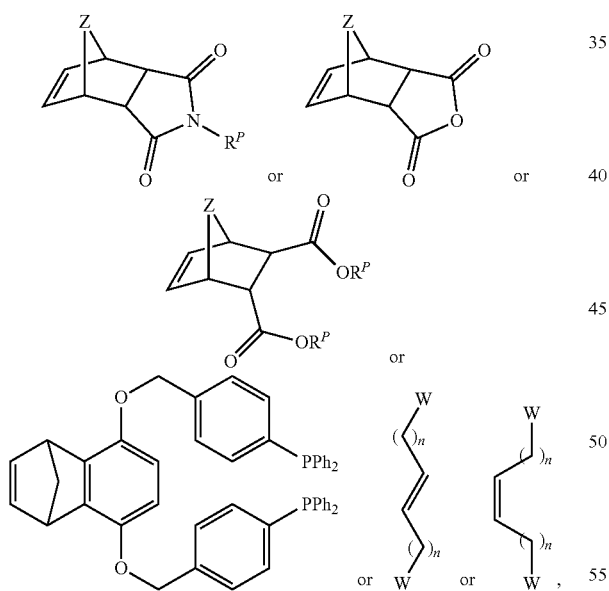

wherein
wherein
Z is —O— or C($R_a$)($R_b$);
$R^P$ is independently H; or $C_{1-6}$ alkyl optionally substituted at the terminus with —N(Ra)($R_b$), —O—$R_a$, —C(O)O—$R_a$, —OC(O)—($C_{1-6}$ alkyl), or —OC(O)—($C_{6-10}$ aryl); or an optionally protected sequence of 3 to 10 amino acids (preferably including R-G-D or arginine-glycine-aspartic acid);
W is independently —N(Ra)($R_b$), —O—$R_a$, or —C(O)O—$R_a$, —P(O)(O$R_a$)$_2$, —SO$_2$(O$R_a$), or SO$_3^-$;

$R_a$ and $R_b$ are independently H or $C_{1-6}$ alkyl;
the $C_{6-10}$ aryl is optionally substituted with 1, 2, 3, 4, or 5 optionally protected hydroxyl groups (the protected hydroxyl groups preferably being benzyl); and
n is independently 1, 2, 3, 4, 5, or 6.
Non-limiting examples of such functionalized materials include:

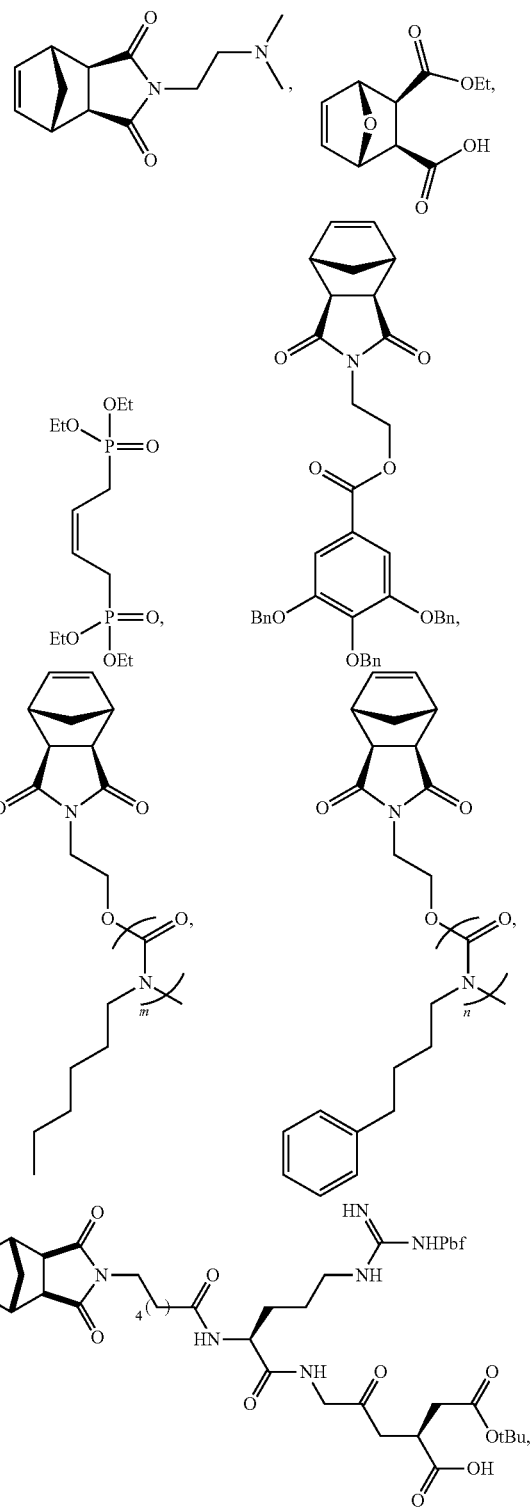

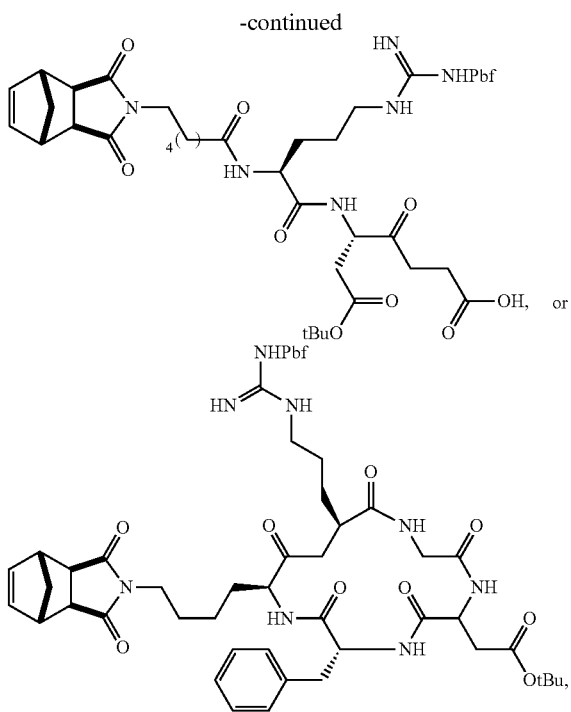

where Bn is benzyl, tBu is tert-butyl, and Pbf is 2,2,4,6,7-pentamethyldihydrobenzofuran. Other protecting groups may also be employed.

Incorporation of such functional groups provides for further functionalization of the pre-polymerized or polymerized compositions, thereby greatly expanding the utility options available for such compositions. Such functional groups, then, can be used as linking points for the additional of other materials, including, for example, natural or synthetic amino acid sequences. In certain embodiments, $R^P$ can be further functionalized to include:

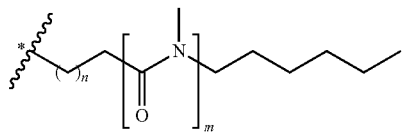

Polymerized products (either 2-dimensional optionally patterned coatings or optionally patterned 3-dimensional structures) prepared from the pre-polymerized compositions may be useful as scaffolds for drug delivery or tissue regeneration. Films or articles comprising pendant optionally protected sequence of 3 to 10 amino acids (preferably including R-G-D or arginine-glycine-aspartic acid) are known to be useful in tissue regeneration applications and the present inventive compositions and methods provide convenient routes to these materials Building upon this concept of incorporating functionalized materials into or pendant to polymer matrices (either films or 3-dimensional articles) derived from photosensitive polymerizable matrices, the present inventors have also discovered that it is possible to incorporate catalytic organometallic materials into such matrices. In particular, the present invention(s) contemplates photosensitive compositions comprising a Fischer-type carbene ruthenium metathesis catalyst admixed or dissolved within a polymerizable material matrix comprising at least one unsaturated organic precursor and at least one unsaturated tethered organometallic precursor, or ligand capable of coordinating to form an organometallic precursor (e.g., vinyl bipyridine, bisphosphines, and carbene precursors) each organic and organometallic precursor having at least one alkene or one alkyne bond.

As used herein, the term "unsaturated tethered organometallic precursor" is defined as referring to organometallic complex having a pendant alkene or alkyne group capable of being incorporated into the polymerized matrix. This concept of tethering organometallic materials, including catalytic materials is well understood in chemistry, as such tethering methods are frequently used to immobilize homogenous catalysts onto stationary matrices (e.g., silica or alumina) By "tethered" or "tethering group," it is appreciated by the person of skill in the art that this refers to linking groups, for example hydrocarbylene linking group such as an alkylene, substituted alkylene, heteroalkylene, substituted heteroalkene, arylene, substituted arylene, heteroarylene, or substituted heteroarylene linkage, including alkylene, arylene, amido, amino, or carboxylato. The specific nature of the linking group is not believed to be necessarily limiting, provided the group contains a reactive alkene or alkyne group capable of being incorporated into the polymerized matrix.

In some embodiments, the organometallic moiety comprises a Group 3 to Group 12 transition metal, preferably Fe, Co, Ni, Ti, Al, Cu, Zn, Ru, Rh, Ag, Ir, Pt, Au, or Hg. In preferred embodiments, the organometallic moiety comprises Fe, Co, Ni, Ru, Rh, Ag, Ir, Pt, or Au. The organometallic moieties may be attached by or contain monodentate, bidentate, or polydentate ligands, for example cyclopentadienyls, imidazoline (or their carbene precursors), phosphines, polyamines, polycarboxylates, nitrogen macrocycles (e.g., porphyrins or corroles), provided these ligands contain the pendant alkene or alkyne group capable of being incorporated into the polymerized matrix. Non-limiting examples of this concept include:

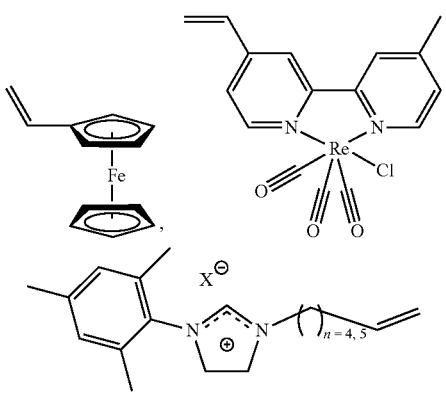

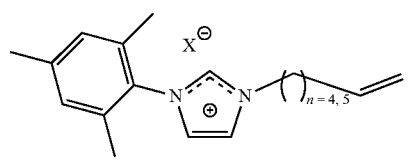

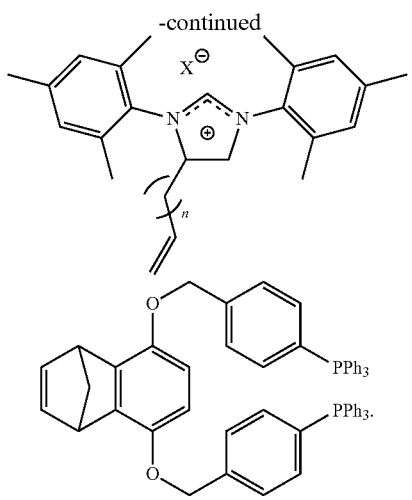

Representative chemistry of the polymerized product into which such an organometallic was incorporated is described in Examples 13 and 14.

In certain embodiments, the organometallic moiety is chosen to be capable of catalyzing the oxidation or reduction of an organic substrate under oxidizing or reducing conditions. The terms "oxidizing or reducing conditions" are likewise generally understood by chemists skilled in the art, and include those conditions comprising the presence of oxidizing (oxygen, peroxides, etc.) or reducing (hydrogen, hydrides, etc.) agents. Such oxidation reactions include, but are not limited to, oxidations of alkenes or alkynes to form alcohols, aldehydes, carboxylic acids or esters, ethers, or ketones, or the addition of hydrogen-halides or silanes across unsaturates. Such oxidation reactions include, but are not limited to, reduction of alkenes to alkanes and reduction of alkynes to alkenes or alkanes. Certain of these organometallic moieties may be used as pendant metathesis or cross-coupling catalysts or for splitting water.

Metatheses Reactions

The metathesis reactions contemplated by the present inventions include Ring-Opening Metathesis Polymerization (ROMP), Ring-Closing Metathesis (RCM), and Cross Metathesis (CM). While often described in terms of "olefin metathesis," it should also be understood that both olefinic and acetylenic bonds can participate in such reactions, and so as used herein, the term "olefin metathesis" is to be interpreted as involving the redistribution of olefinic or acetylenic bonds. Each of these types of reactions is well known to those skilled in the relevant art in this capacity.

In those contemplated embodiment related to photoresists (to be described further infra), the descriptions are generally provided in terms of selective polymerizations, for example by ROMP or cross-metathesis, so as to provide spatially specific regions of cross-linked polymers. But it should also be appreciated that this spatial and temporal selectivity available by the photoactivated catalysts may also be applied to change the solubility properties of the irradiated region without crosslinking—for example by only partial reaction of the precursors, cross metathesis of an olefinic precursor with a polymer, or through depolymerization.

Photosensitive Compositions, Including Photoresists

As should be appreciated by the descriptions herein, one of the several features of the present inventions is the ability to spatially and temporally control the catalytic activities of the systems with remarkable precision, owing to the high contrast in activity between the irradiated and unirradiated catalysts. The high activities of the irradiated catalysts allows for good activity, even at low embedded catalyst concentrations. In some embodiments, the Fischer-type carbene ruthenium metathesis catalyst is present at a concentration in a range of from about 0.001% to about 5% by weight, relative to the weight of the entire composition. This concentration range depends on the reactivities of the catalyst and the polymerizable material precursors, the desired handling conditions, and the desired rates of polymerization. In certain other embodiments, ruthenium carbene metathesis catalyst is present at a concentration in a range of from about 0.001% to about 0.01%, from about 0.01% to about 0.1%, from about 0.1% to about 1%, from about 1% to about 2%, from about 2% to about 3%, from about 3% to about 4%, from about 4% to about 5%, or a combination thereof, all by weight, relative to the weight of the entire composition. The systems also allow for higher concentrations, for example up to about 10 or 15% by weight, relative to the weight of the entire composition, but here cost begins to become dissuasive for most practical applications.

As described above, the methods of the present invention also consider that the Fischer-type carbene ruthenium metathesis catalyst, as described herein, may be dissolved in a solvent in the presence of at least one unsaturated organic precursor or are admixed or dissolved in at least one unsaturated organic precursor. In the circumstances where the user contemplates the use of these compositions as photoresists, the Fischer-type catalyst may be added to the organic precursor directly or generated in situ as described elsewhere herein. This in situ generation of the catalyst may involve providing a catalyst containing a Schrock-type carbene, which is subsequently quenched to form the Fischer-type carbene catalyst. If so, the generation of the catalyst may be accompanied by partial polymerization or crosslinking of the originally added organic precursor, and the intermediate viscosity of this partial polymerized or cross-linked composition may be controlled by the time before quenching. Raising the viscosity of the photosensitive compositions provides several advantages, including improving the oxidative stability of the otherwise potentially air-sensitive catalysts. The raised viscosity also controls the diffusion length of the active catalyst species through the composition, which in turn can improve the resolution of the lithographically defined structures.

In some embodiments, it is convenient to use a non-reactive solvent (low boiling solvents may be preferred, such as methylene chloride, tetrahydrofuran, diethyl ether, toluene, etc.) to provide and maintain lower initial viscosities, so as to allow for more efficient intimate mixing of the catalyst within the total composition. In the case of the phenanthroline-ligated catalysts derivatives described herein, use of more reactive solvents, including water, acetonitrile, and chloroform, may be tolerable. Once the catalyst is intimately distributed within the composition, the non-reactive solvent may be conveniently removed, for example under vacuum or with heat. In some cases, once the Fischer-type catalyst is added or prepared, additional or different organic precursor may be added to dilute the catalyst further. The viscosity of the final, unexposed product may be adjusted by the type and amount of the constituents. For example, in some embodiments, the viscosity is such that the composition is suitable for spin-coating, dip coating, or spraying. In other embodiments, the photosensitive composition can have the form of a gelled, solid, or semi-solid film. In various independent embodiments, the viscosity of the composition, at the contemplated temperature of application (preferably ambient room temperature) is in a range of from about 1 cSt to about 10 cSt, from about 10 cSt to about 50 cSt, from about 50 cSt to about 100 cSt, from about 100 cSt to about 250 cSt, from about 250 cSt to about 500 cSt, from about 500 cSt to about 1000 cSt, from about 1000 cSt to about 2000 cSt, from about 2000 cSt to about 5000 cSt, or higher. Higher viscosities appear provide increased oxidative stability of the ruthenium carbene catalysts.

Part of the challenge in developing an olefin metathesis-based photoresist is achieving a stark contrast between the reactivity of the catalyst in the light and the dark. Additionally, the requirements of ambient stability and processability present barriers to the industrial implementation of transition metal based photocatalysts. In the present invention, certain embodiments provide that a standard quenching procedure for ROMP or cross-metathesis reactions generates a photoactive latent catalyst. This serendipitous discovery allows for the facile synthesis of a new family of photocurable materials. The addition of substituted vinyl ethers is a widely employed method of quenching ROMP or cross-metathesis reactions. The regioselective formation of vinyl ether complexes, for example, is extremely rapid and irreversible under certain conditions, leading to the use of vinyl ether "trapping" as a tool for determining catalyst initiation rates. The resultant ruthenium Fischer-type carbenes are generally considered to be unreactive. While not intending to be bound by the correctness or incorrectness of any particular theory, it appears that quenching a living ROMP reaction yields a methylene-terminated polymer chain and a presumably 14-electron ruthenium vinyl ether. While the phosphine or pyridine ligands typically found on ruthenium ROMP catalysts could in principle re-coordinate to the quenched complex, the statistical likelihood of this is extremely low considering the concentration and stoichiometry of typical ROMP reactions. In addition, the air-sensitivity of the ruthenium vinyl ether complexes aids in the quenching process, through almost immediate decomposition of the alkylidene species. A typical quenching procedure utilizes excess vinyl ether and immediate precipitation of the polymer to remove the catalyst. Interestingly, the addition of the

ligands, such a phenanthrolines, appears to reduce the nascent reactivity of these catalysts even further, such that the metathesis reactivity is only unleashed by irradiation with light, or excessive heating. This enables moderate heating to be applied as part of the patterning process, enabling pre- or post-exposure baking steps to be implemented.

The photosensitive compositions, including photoresists, may additionally comprise other materials, so long as their presence does not interfere with the ability of the photoactivated catalysts to effect the metathesis reactions under irradiation conditions. For example, these compositions, including photoresists, may contain colorants, surfactants, and stabilizers, as well as functional particles including, for example, nanostructures (including carbon and inorganic nanotubes), magnetic materials (e.g., ferrites), and quantum dots.

Methods of Patterning a Polymer on a Substrate

Embodiments of the present invention also provide methods of providing patterned polymer layers using the Fischer-type carbene photocatalysts, which may be described as PhotoLithographic Olefin Metathesis Polymerization (PLOMP). In this procedure, a latent metathesis catalyst is activated by light to react with the olefins in the surrounding environment, providing for the development of a negative tone resist by using the photocatalyst to polymerize, crosslink, or both polymerize and crosslink a difunctional ROMP monomer or other unsaturated precursor within a polymerizable material matrix of linear polymer or polymer precursor. In principle, a positive tone resist can also be developed, by using light-triggered secondary metathesis events to increase the solubility of the irradiated regions. This can be considered a "chemically amplified" resist, in that the photoactive species is a catalyst for the crosslinking of the polymer matrix. The versatility of these ruthenium-mediated olefin metathesis reactions can now be utilized to photopattern a variety of functional materials via PLOMP, advancing the field of photoinitiated olefin metathesis from a curiosity to materials science applicable to mass microfabrication.

Some embodiments provide methods of patterning a polymeric image on a substrate, each method comprising;

(a) depositing a layer of photosensitive composition of any one of the compositions described herein on the substrate;

(b) irradiating a portion of the layer of photosensitive composition with a light having appropriate wavelength(s), as described elsewhere herein, thereby providing a patterned layer of polymerized and unpolymerized regions. Certain other embodiments further comprise removing the unpolymerized region of the pattern.

In principle, the substrates can comprise any metallic or non-metallic; organic or inorganic; conductive, semi-conductive, or non-conductive material, or any combination thereof. Even so, it is contemplated that these patterned polymer layers will find utility in electronic applications including those where semiconductor wafers comprising silicon, GaAs, and InP. One of the many advantages of these inventive systems, certainly over many commercial resists, is the ability to maintain surface adhesion to the native oxide surfaces of silicon wafers, for example, without any etching or surface derivatization. By contrast, many commercial photoresists require HF etching of the oxide and/or surface derivatization with reactive molecules such as hexamethyldisilazane. In this respect, the presently described photosensitive systems offer a safer and more versatile alternative, as the polymer composition can be easily tuned to modulate adhesion. For examples, in the examples described herein, the poly(COD) resist batches showed excellent adhesion to silicon coupons, which were first cleaned with piranha. Additionally, the PLOMP resists do not require post-exposure baking to develop. Currently, ruthenium-mediated ROMP is employed in a number of industrial scale applications, including high-modulus resins and extremely chemically resistant materials. PLOMP can provide UV-curable and patternable coatings with these desired materials properties. Finally, the ability to generate many batches of resist in a single workday enables rapid prototyping for future development.

In some embodiments, the patterned polymers may be processed to form single layer or multilayer polymer structures. In multilayer structures, each layer may be the same or different than any other of the deposited layer, and may be individually patterned as described herein. Similarly, each layer may be interleaved with intermediately deposited metal, metal oxide, or other material layer. These interlayers may be deposited for example by sputtering, or other chemical or vapor deposition technique, provided the processing of these interlayers does not adversely affect the quality of the patterned layers of deposited polymers.

The photosensitive compositions may be deposited by spin coating, dip coating, or spray coating, or alternatively, depending on the physical form of the photosensitive composition, may be deposited by laminating a gelled or solid film on the substrate.

The photosensitive compositions may be irradiated by any variety of methods known in the art. In certain embodiments, patterning may be achieved by photolithography, using a positive or negative image photomask. In other embodiments, patterning may be achieved by interference lithography (i.e., using a diffraction grating). In other embodiments, patterning may be achieved by proximity field nanopatterning. In still other embodiments, patterning may be achieved by diffraction gradient lithography. In still other embodiments, patterning may be used by a direct laser writing application of light, such as by multi-photon lithography. Additional embodiments provide that the patterning may be accomplished by nanoimprint lithography.

The Fischer-type carbene ruthenium metathesis catalysts can be activated using light having at least one wavelength in a range of from about 150 to about 800 nm or in a range of from about 220 to about 440 nm, from about 240 to about 260 nm, or from about 260 nm to about 340 nm, or from about 340 to about 360 nm, or from about 360 to about 800 nm or a combination thereof, more preferably in a range of from about 240 to about 260 nm or from about 340 to about 360 nm. As described above, the intensity of this at least wavelength is in a range of about 2 watts to about 6000 watts, preferably about 2 watts to about 10 watts. In certain aspects the catalysts can be activated using 2- or 3-photon energy sources at 700 to 800 nm, more specifically using a 790 nm laser. This two-photon energy is equivalent to 395 nm; the 3-photon energy is equivalent to about 263 nm).

The dimensions of the resulting features of the polymerized structures are, in part, dictated by the wavelength of the irradiating light, the method of irradiation, and the character of the photosensitive compositions. Higher viscosities and the optional presence of additional quenchants may usefully minimize diffusion of the catalyst in the composition, so as to provide for better resolution. In certain embodiments, the polymerized polymer exhibits features (e.g., channels, ridges, holes, or posts) having dimensions on the millimeter scale (e.g., from about 1 mm to about 10 mm, from about 10 mm to about 50 mm, from about 50 mm to about 100 mm, from about 100 mm to about 500 mm, from about 500 mm to about 1000 mm, or a combination thereof), the micron scale (e.g., from about 1 micron to about 10 microns, from about 10 microns to about 50 microns, from about 50 microns to about 100 microns, from about 100 microns to about 500 microns, from about 500 microns to about 1000 microns, or a combination thereof), or the nanometer scale (e.g., from about 1 nm to about 10 nm, from about 10 nm to about 50 nm, from about 50 nm to about 100 nm, from about 100 to about 200 nm, from about 200 to about 300 nm, from about 300 to about 400 nm, from about 400 to about 500 nm, from about 500 to about 600 nm, from about 600 to about 700 nm, from about 700 to about 800 nm, or a combination thereof. See, e.g., FIG. 3. Interference or diffraction gradient lithography may provide for polymer layers having continuous or discontinuous thicknesses.

The methods and derived polymer products may generally serve as masks or templates for chemical etching processes. Polymers made by these processes are qualitatively stable to dichloromethane, isopropanol, acetone, 2.5 M hydrochloric acid, and concentrated sulfuric acid after being submerged for approximately 24 hours.

Three-Dimensional Structures

The present invention(s) also provides compositions and methods suitable for making 3-dimensional structures comprising a plurality of polymer layers and 3-dimensional patterns. The ability to provide specifically dimensioned patterns makes these structures particularly useful, for example, in 3-dimensional photonic or chemochromic devices.

In certain embodiments, such structures are prepared by methods comprising:

(a) depositing at least two layers of a polymerizable material composition having at least one alkene or alkyne capable of undergoing a metathesis polymerization or crosslinking reaction, the deposition forming a stacked assembly;

(b) irradiating at least a portion of the stacked assembly with light, such that light penetrates and irradiates at least two layers of the stacked assembly, under conditions sufficient to polymerize or crosslink at least portions of adjacent layers of the stacked assembly;

wherein each layer comprises a Fischer-type carbene ruthenium metathesis catalyst admixed or dissolved therein. In related embodiments, the portions of the assembly not reacted may be subsequently removed.

These layers of polymerizable materials generally, but not necessarily, comprise mainly polymers, with the additional presence of small amounts of polymerizable precursors or crosslinkers. That is, each layer may comprise at least 50%, 60%, 70%, 80%, 90%, 95%, or 98% by weight of preformed polymer, the weight percentage based on the total weight of the layers of a polymerizable material.

In some embodiments, one or more of the at least two layers of a polymerizable material may contain residual ruthenium metathesis catalyst that was used to prepare that particular layer. That is, that layer may have already been derived from a ROMP-type catalysis synthesis, and have residual catalyst contained therein. Alternatively, additional or new ruthenium metathesis catalyst may be admixed or dissolved within a pre-prepared layer of a polymerizable material by dissolving it in the presence of a solvent (as described herein) or incorporating the catalyst into a solvent swelled.

Such layer or layers may also contain residual polymer precursor from the original (incomplete) polymerization or contain residual less reactive polymer precursors. Alternatively, the layer may have had additional polymerizable or crosslinkable materials added to it, for example by dissolving or swelling the layer in the presence of the additional polymerizable or crosslinkable material. Such residual precursors are akin to those described herein. Other chemical cross-linkers are known in the art.

The stacked assembly may be formed to comprise adjacent layers having materials of similar composition. Alternatively, adjacent layers may be compositionally different. Or the stacked assembly may comprise a combination of adjacent layers being compositionally the same and different. In preferred embodiments, each layer of the stacked assembly comprises a pre-formed polymer having different chemistries from other pre-formed polymer(s) in the other layer(s). Individual layers within the stacked assembly may have thickness of any practical dimension, but particular embodiments include those where the thickness of each layer is independently on the millimeter scale (e.g., from about 1 mm to about 10 mm, from about 10 mm to about 50 mm, from about 50 mm to about 100 mm, from about 100 mm to about 500 mm, from about 500 mm to about 1000 mm, or a combination thereof), the micron scale (e.g., from about 1 micron to about 10 microns, from about 10 microns to about 50 microns, from about 50 microns to about 100 microns, from about 100 microns to about 500 microns, from about 500 microns to about 1000 microns, or a combination thereof), or the nanometer scale. In the latter case, the layers may be independently in a range of from about 50 to about 100 nm, from about 100 to about 200 nm, from about 200 to about 300 nm, from about 300 to about 400 nm, from about 400 to about 500 nm, from about 500 to about 600 nm, from about 600 to about 700 nm, from about 700 to about 800 nm, from about 800 to about 900 nm, from about 900 to about 1000 nm, or a combination thereof. By selecting the thickness and optical characteristics of adjacent layers, it is possible to tune the optics of the entire device.

Figure 6:
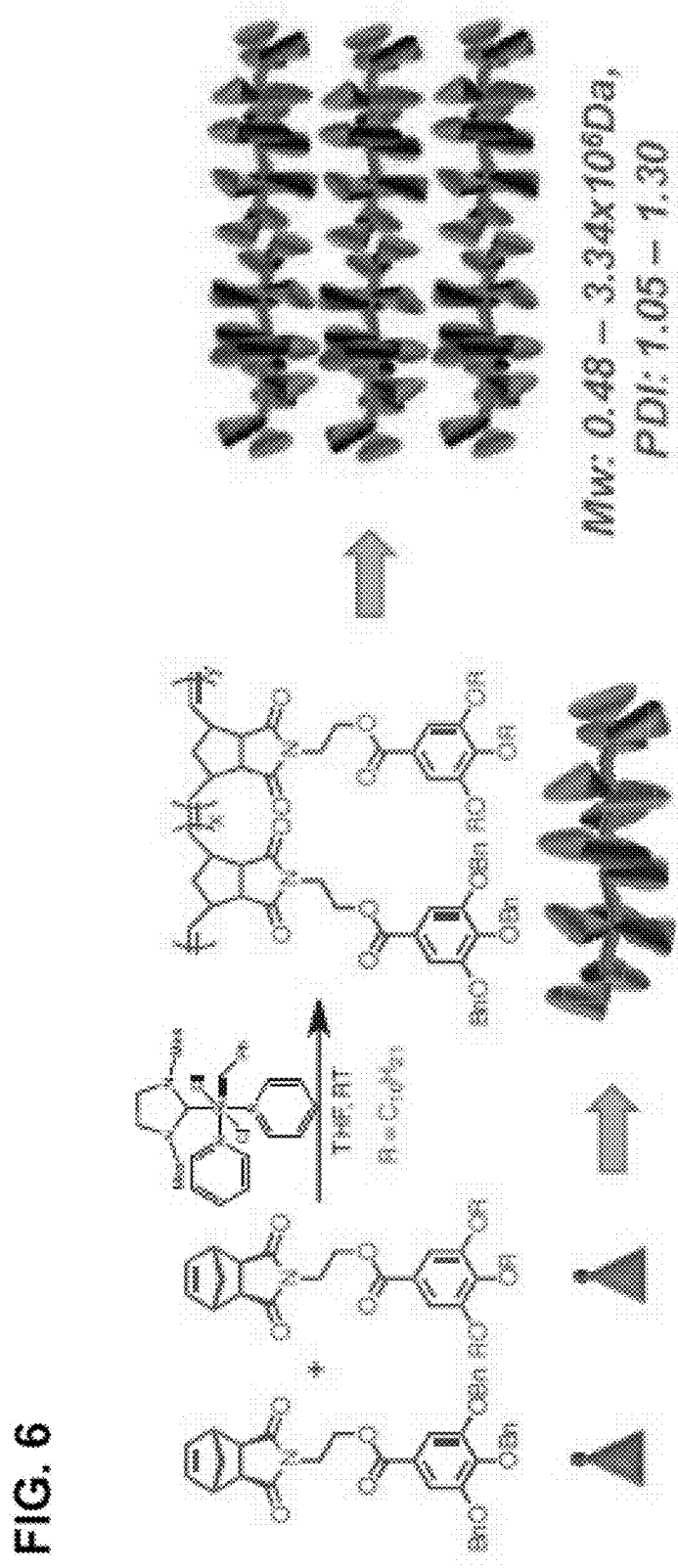
FIG. 6 shows a schematic representation of a self-assembled wedge copolymer.

In certain cases, the layers of the polymerizable material compositions may be deposited sequentially upon one another, or may be allowed to self-assemble to the stacked assembly when different materials are mixed together in a liquid. Self-assembly would appear to be a more intimate and useful way of forming such stacked structures, particularly at the nano-scale dimensions useful for photonic or chemochromic devices, but the ability to self-assemble effectively depends on the nature of the various layers. For example, certain block copolymers are able to self-assemble providing lateral and vertical domains having dimensions in a range of from about 5 to about 1500 nanometer, preferably in a range of from about 75 to about 300 nm domains. As such, layers comprising block copolymers are useful materials to be incorporated in these methods. Brush (graft) block, wedge-type block, and hybrid wedge and polymer block copolymers. See FIG. 6. Such block copolymers are described in copending U.S. Patent Application Publication Nos. 2014/0011958, 2013/0296491, and 2013/0324666 and in Piunova, et al., *J. Amer. Chem. Soc,* 2013, 135 (41), pp 15609-15616, Miyake, G. M., et al., *Angewandte Chemie International Edition* 2012, 51, 11246-11248, Sveinbjörnsson, B. R., et al., *PNAS* 2012, 109, 14332-14336, and Miyake, G. M., et al., *J. Am. Chem. Soc.* 2012, 134, 14249-14254, each of which is incorporated by reference for their description of the polymers and copolymers, are considered especially attractive materials to be used in these methods, though the methods are not limited to these choices of materials.

Once the stacked assembly is formed, at least a portion of it is subject to irradiation with light, under conditions described herein, such that light penetrates and irradiates at least two layers of the stacked assembly, under conditions sufficient to polymerize or crosslink at least portions of adjacent layers of the stacked assembly. Whereas the adjacent layers could be delaminated prior to irradiation, the application of light activates the incorporated ruthenium metathesis catalyst to crosslink these adjacent layers to a coherent structure. In other embodiments, the light is directed to pass through and irradiate at least a portion of all of the layers of the stacked assembly. In other embodiments, the entire structure is irradiated with light under conditions to crosslink the entire assembly.

Whereas a stacked assembly can be irradiated in its entirety, another set of embodiments provide that the irradiating is done by patterned exposure of light to the stacked assembly, so as to provide a three-dimensional pattern of polymerized and unpolymerized regions through the stacked assembly. Much like the compositions provide that patterned irradiation of planar polymer layers can give rise to nano- and micro-dimensioned patterns, for example by using a direct writing application of light or by interference, nanoimprint, or diffraction gradient lithography, so too can this same patterning technology be used to form similarly dimensioned patterns in 3-dimensions. Once selectively polymerized or crosslinked, the unreactive portions of the structure may be removed.

As expected, embodiments of the present invention include those structures prepared using these methods, and articles incorporating these structures. Photonic devices, including chemochromic sensors, solar cells, dielectric mirrors, and reflective coatings are contemplated embodiments.

ADDITIONAL EMBODIMENTS

The following listing of embodiments in intended to complement, rather than displace or supersede, the previous descriptions.

Embodiment 1

A photosensitive composition comprising a ruthenium carbene metathesis catalyst of Formula (II):

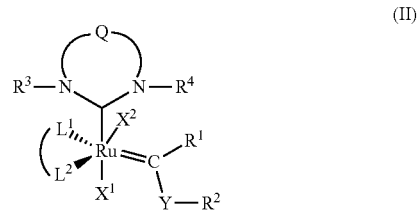

admixed within a polymerizable material matrix comprising at least one unsaturated organic precursor;

wherein $L^1$, and $L^2$ are independently neutral electron donor ligands, linked by a hydrocarbylene linking group such as an alkylene, substituted alkylene, heteroalkylene, substituted heteroalkene, arylene, substituted arylene, heteroarylene, or substituted heteroarylene linkage, such that when taken together with the Ru to which they are bound or coordinated, form a 5, 6, or 7-membered ring;

$X^1$ and $X^2$ are independent anionic ligands;

Y is O, N—$R^1$, or S, preferably O; and

Q is a two-atom linkage having the structure —$CR^{11}R^{12}$—$CR^{13}R^{14}$— or —$CR^{11}$=$CR^{13}$—, preferably —$CR^{11}R^{12}$—$CR^{13}R^{14}$—, wherein $R^{11}$, $R^{12}$, $R^{13}$, and $R^{14}$ are independently selected from hydrogen, hydrocarbyl, substituted hydrocarbyl, heteroatom-containing hydrocarbyl, substituted heteroatom-containing hydrocarbyl, and functional groups.

$R^1$ and $R^2$ are independently hydrogen, optionally substituted hydrocarbyl, optionally substituted heteroatom-containing hydrocarbyl, functional groups, or may be linked to form a cyclic group, which may be aliphatic or aromatic, and may contain substituents and/or heteroatoms; and $R^3$ and $R^4$ are independently optionally substituted hydrocarbyl, or optionally substituted heteroatom-containing hydrocarbyl, and may contain substituents and/or heteroatoms. The ruthenium carbene metathesis catalyst of Formula (II) may be added as described here or generated in situ as otherwise described herein. The independent $X^1$ and $X^2$ anionic ligands may be positioned cis with respect to one another.

Embodiment 2

The photosensitive composition of Embodiment 1, wherein the Ru=C(R$^1$)(Y—R$^2$) moiety is a substituted vinyl ether carbene.

Embodiment 3

The photosensitive composition of Embodiments 1 or 2, wherein R$^2$ is C$_{1-6}$ alkyl, preferably ethyl, propyl, or butyl.

Embodiment 4

The photosensitive composition of any one of Embodiments 1 to 3, wherein Q is —CH$_2$—CH$_2$— and either R$^3$ or R$^4$, or both R$^3$ and R$^4$ are phenyl groups, optionally substituted in the 2,6 positions with independent C$_{1-6}$ alkyl groups, preferably C$_{3-6}$ alkyl groups which may be branched or linear, e.g., including methyl, ethyl, n-propyl, iso-propyl, n-butyl, sec-butyl, tert-butyl. Additionally, the phenyl groups may be optionally substituted in the 4-positions with an electron-withdrawing or -donating group as described herein, for example, alkyl, alkoxy, nitro, or halo.

Embodiment 5

The photosensitive composition of any one of Embodiments 1 to 4, wherein Q is —CH$_2$—CH$_2$— and R$^3$ and R$^4$ are independently mesityl or optionally substituted adamantyl.

Embodiment 6

The photosensitive composition of any one of Embodiments 1 to 5, wherein

is an aromatic bidentate diamine.

Embodiment 7

The photosensitive composition of any one of Embodiments 1 to 6, wherein

is a phenanthroline, optionally substituted with electron-withdrawing or electron-donating groups.

Embodiment 8

The photosensitive composition of Embodiment 1, where the metathesis catalyst comprises a compound having a structure:

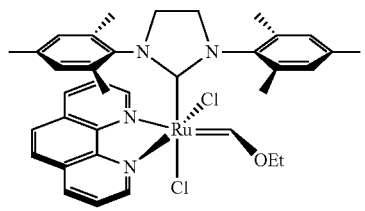

including a corresponding structure generated in situ.

Embodiment 9

The photosensitive composition of any one of Embodiments 1 to 8, wherein the ruthenium carbene catalyst, upon activation by irradiation of light of at least one wavelength in a range of from about 150 nm to about 800 nm, preferably in a range of from about 200 nm to about 380 nm, or about 240 nm to about 380 nm, can crosslink or polymerize at least one of the unsaturated organic precursor.

Embodiment 10

The photosensitive composition of any one of Embodiments 1 to 9, wherein the ruthenium carbene metathesis catalyst is present at a concentration in a range of from about 0.001% to about 5% by weight, or a subset thereof, relative to the weight of the entire composition.

Embodiment 11

The photosensitive composition of any one of Embodiments 1 to 10, wherein the unsaturated organic precursor comprises:

(a) a mono-unsaturated cyclic olefin represented by the structure (B)

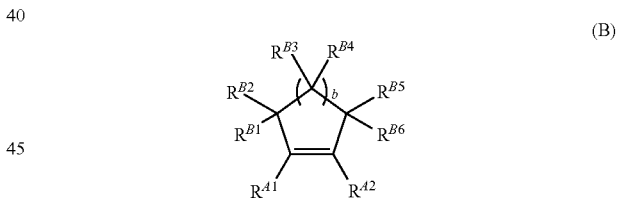

wherein b is an integer generally although not necessarily in the range of 1 to 10, typically 1 to 5, R$^{A1}$ and R$^{A2}$ are independently hydrogen, hydrocarbyl (e.g., C$_1$-C$_{20}$ alkyl, C$_5$-C$_{20}$ aryl, C$_5$-C$_{30}$ aralkyl, or C$_5$-C$_{30}$ alkaryl), substituted hydrocarbyl (e.g., substituted C$_1$-C$_{20}$ alkyl, C$_5$-C$_{20}$ aryl, C$_5$-C$_{30}$ aralkyl, or C$_5$-C$_{30}$ alkaryl), heteroatom-containing hydrocarbyl (e.g., C$_1$-C$_{20}$ heteroalkyl, C$_5$-C$_{20}$ heteroaryl, heteroatom-containing C$_5$-C$_{30}$ aralkyl, or heteroatom-containing C$_5$-C$_{30}$ alkaryl), and substituted heteroatom-containing hydrocarbyl (e.g., substituted C$_1$-C$_{20}$ heteroalkyl, C$_5$-C$_{20}$ heteroaryl, heteroatom-containing C$_5$-C$_{30}$ aralkyl, or heteroatom-containing C$_5$-C$_{30}$ alkaryl) and, if substituted hydrocarbyl or substituted heteroatom-containing hydrocarbyl, wherein the substituents may be functional groups ("Fn") such as alkene, alkyne, phosphonato, phosphoryl, phosphanyl, phosphino, sulfonato, C$_1$-C$_{20}$ alkylsulfanyl, C$_5$-C$_{20}$ arylsulfanyl, C$_1$-C$_{20}$ alkylsulfonyl, C$_5$-C$_{20}$ arylsulfonyl, C$_1$-C$_{20}$ alkylsulfinyl, C$_5$-C$_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group (wherein the metal may be, for example, Sn or Ge); and $R^{B1}$, $R^{B2}$, $R^{B3}$, $R^{B4}$, $R^{B5}$, and $R^{B6}$ are independently selected from the group consisting of hydrogen, hydrocarbyl, substituted hydrocarbyl, heteroatom-containing hydrocarbyl, substituted heteroatom-containing hydrocarbyl and —$(Z^*)_n$-Fn where $Z^*$ is a hydrocarbylene linking group such as an alkylene, substituted alkylene, heteroalkylene, substituted heteroalkene, arylene, substituted arylene, heteroarylene, or substituted heteroarylene linkage; and wherein if any of the $R^{B1}$ through $R^{B6}$ moieties is substituted hydrocarbyl or substituted heteroatom-containing hydrocarbyl, the substituents may include one or more —$(Z^*)_n$-Fn groups; or (b) a monocyclic diene represented by the structure (C)

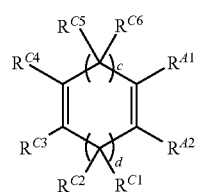

(C)

wherein c and d are independently integers in the range of 1 to about 8, typically 2 to 4, preferably 2 (such that the reactant is a cyclooctadiene);

$R^{C1}$, $R^{C2}$, $R^{C3}$, $R^{C4}$, $R^{C5}$, and $R^{C6}$ are defined as corresponding to $R^{B1}$ through $R^{B6}$; or (c) a bicyclic or polycyclic olefin represented by the structure (D)

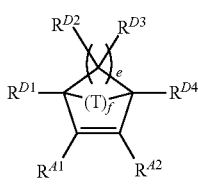

(D)

wherein
$R^{D1}$, $R^{D2}$, $R^{D3}$, and $R^{D4}$ are as defined as corresponding to $R^{B1}$ through $R^{B6}$,
e is an integer in the range of 1 to 8 (typically 2 to 4)
f is generally 1 or 2;

T is lower alkylene or alkenylene (generally substituted or unsubstituted methyl or ethyl), $CHR^{G1}$, $C(R^{G1})_2$, O, S, N—$R^{G1}$, P—$R^{G1}$, O=P—$R^{G1}$, Si$(R^{G1})_2$, B—$R^{G1}$, or As—$R^{G1}$ where $R^{G1}$ is alkyl, alkenyl, cycloalkyl, cycloalkenyl, aryl, alkaryl, aralkyl, or alkoxy. Furthermore, any of the $R^{D1}$, $R^{D2}$, $R^{D3}$, and $R^{D4}$ moieties can be linked to any of the other $R^{D1}$, $R^{D2}$, $R^{D3}$, and $R^{D4}$ moieties to provide a substituted or unsubstituted alicyclic group containing 4 to 30 ring carbon atoms or a substituted or unsubstituted aryl group containing 6 to 18 ring carbon atoms or combinations thereof and the linkage may include heteroatoms or functional groups, e.g. the linkage may include without limitation an ether, ester, thioether, amino, alkylamino, imino, or anhydride moiety; or (d) a norbornenes represented by the structure (E)

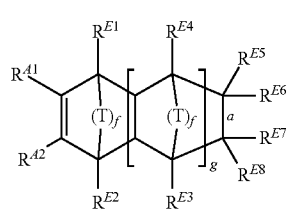

(E)

wherein
$R^{E1}$, $R^{E2}$, $R^{E3}$, $R^{E4}$, $R^{E5}$, $R^{E6}$, $R^{E7}$, and $R^{E8}$ are as defined as corresponding to $R^{B1}$ through $R^{B6}$;
"a" represents a single bond or a double bond;
f is 1 or 2;
g is an integer from 0 to 5, and when "a" is a double bond one of $R^{E5}$, $R^{E6}$ and one of $R^{E7}$, $R^{E8}$ is not present; or (e) a mixture thereof.

Embodiment 12

The photosensitive composition of any one of Embodiments 1 to 11, herein the unsaturated organic precursor comprises a compound having a structure:

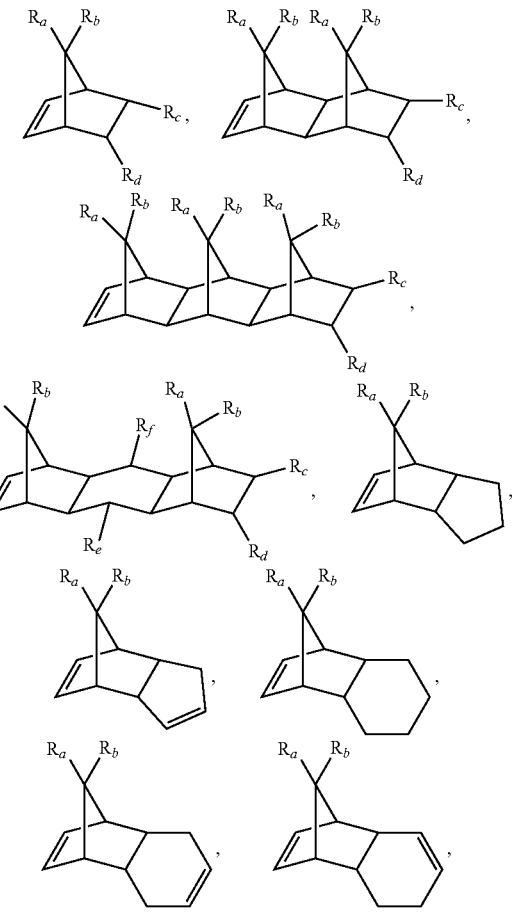

or a mixture thereof, wherein
$R_a$, $R_b$, $R_c$, $R_d$, $R_e$, and $R_f$ are independently H or alkyl (preferably $C_{1-20}$ alkyl, more preferably $C_{1-10}$ alkyl.

Embodiment 13

The photosensitive composition of any one of Embodiments 1 to 12, wherein the unsaturated organic precursor comprises a dicyclopentadiene of structure:

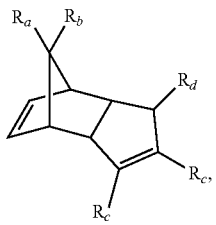

wherein
Ra, $R_b$, $R_c$, $R_d$, $R_e$, and $R_f$ are independently H or alkyl (preferably $C_{1-20}$ alkyl, more preferably $C_{1-10}$ alkyl.

Embodiment 14

The photosensitive composition of any one of Embodiments 1 to 13, wherein the composition has a viscosity capable of being spin coated, dip coated, or spray coated.

Embodiment 15

The photosensitive composition of any one of Embodiments 1 to 13, wherein the photosensitive composition is a gelled, semi-solid or solid film.
Method of Using Photosensitive Composition Comprising New Metathesis Catalyst Embodiment 16

A method of patterning a polymeric image on a substrate, said method comprising;
(a) depositing a layer of a photosensitive composition of any one of Embodiments 1 to 15 on a substrate;
(b) irradiating a portion of the layer of photosensitive composition with a light comprising at least one wavelength in a range of from about 150 to about 800 nm, preferably in a range of from about 240 to about 260 nm or from about 340 to about 360 nm, so as to polymerize the irradiated portion of the layer, thereby providing polymerized and unpolymerized regions in the layer.

Embodiment 17

The method of Embodiment 15, wherein the photosensitive composition is deposited by spin coating, dip coating, or spray coating.

Embodiment 18

The method of Embodiment 16 or 17, wherein photosensitive composition is a gelled, semi-solid or solid film and is deposited by laminating on the substrate.

Embodiment 19

The method of any one of Embodiments 16 to 18, wherein the irradiated portion is patterned through use of a photomask, by a direct writing application of light, or by interference, nanoimprint, or diffraction gradient lithography.

Embodiment 20

The method of any one of Embodiments 16 to 19, wherein the light has an intensity in a range of about 2 watts to about 6000 watts at least one wavelength in the range of from about 150 nm to 800 nm or from about 220 to 440 nm.

Embodiment 21

The method of any one of Embodiments 16 to 20, wherein the patterned layer comprises at least one feature having dimensions on the nanometer or micron scale.

Embodiment 22

The method of any one of Embodiments 16 to 21, further comprising removing the unpolymerized region of the pattern.
Coatings Containing Composition Comprising New Metathesis Catalyst Embodiment 23

A patterned polymer layer prepared according to any one of Embodiments 16 to 22, or an article containing said patterned polymer layer.

Embodiment 24

The polymer layer of Embodiment 23, the polymer layer being resistant to corrosive reagents.

Embodiment 25

A patterned polymer layer prepared according to Embodiment 23 or 24, or an article, the patterned polymer layer being resistant to strong acids, specifically aqueous HF, said patterned polymer being able to withstand exposure to aqueous HF at room temperatures for a period of 1, 2, 3, 4, 5, 6, 12, or 24 hours without measurable peeling from the substrate.
Photosensitive Composition Comprising Tethered Organometallic, Using any Ru-Carbene Catalyst Embodiment 26

A photosensitive composition comprising a Fischer-type carbene ruthenium metathesis catalyst admixed or dissolved within a polymerizable material matrix comprising at least one unsaturated organic precursor and at least one unsaturated tethered organometallic precursor, each organic and organometallic precursor having at least one alkene or one alkyne bond, wherein the ruthenium carbene catalyst can be activated by irradiation by light having at least one wavelength in a range of from about 150 to about 800 nm, or in a range of from about 220 nm to about 440 nm, or from about 240 nm to about 260 nm, or from about 260 nm to about 340 nm, or from about 340 to about 360 nm, or a combination thereof, more preferably in a range of from about 240 to about 260 nm or from about 340 to about 360 nm.

Embodiment 27

The photosensitive composition of Embodiment 26, wherein the at least one unsaturated organic precursor is a ROMP precursor.

Embodiment 28

The photosensitive composition of Embodiment 26 or 27, wherein the at least one unsaturated organic precursor comprises:

(a) a mono-unsaturated cyclic olefin represented by the structure (B)

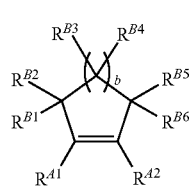

(B)

wherein b is an integer generally although not necessarily in the range of 1 to 10, typically 1 to 5, $R^{A1}$ and $R^{A2}$ are independently hydrogen, hydrocarbyl (e.g., $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), and substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl) and, if substituted hydrocarbyl or substituted heteroatom-containing hydrocarbyl, wherein the substituents may be functional groups ("Fn") such as alkene, alkyne, phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group (wherein the metal may be, for example, Sn or Ge); and $R^{B1}$, $R^{B2}$, $R^{B3}$, $R^{B4}$, $R^{B5}$, and $R^{B6}$ are independently selected from the group consisting of hydrogen, hydrocarbyl, substituted hydrocarbyl, heteroatom-containing hydrocarbyl, substituted heteroatom-containing hydrocarbyl and —(Z*)$_n$-Fn where Z* is a hydrocarbylene linking group such as an alkylene, substituted alkylene, heteroalkylene, substituted heteroalkene, arylene, substituted arylene, heteroarylene, or substituted heteroarylene linkage; and wherein if any of the $R^{B1}$ through $R^{B6}$ moieties is substituted hydrocarbyl or substituted heteroatom-containing hydrocarbyl, the substituents may include one or more —(Z*)$_n$-Fn groups; or (b) a monocyclic diene represented by the structure (C)

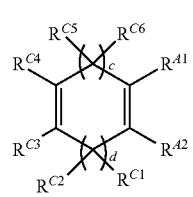

(C)

wherein c and d are independently integers in the range of 1 to about 8, typically 2 to 4, preferably 2 (such that the reactant is a cyclooctadiene);

$R^{C1}$, $R^{C2}$, $R^{C3}$, $R^{C4}$, $R^{C5}$, and $R^{C6}$ are defined as corresponding to $R^{B1}$ through $R^{B6}$; or (c) a bicyclic or polycyclic olefin represented by the structure (D)

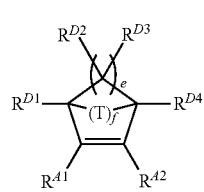

(D)

wherein
$R^{D1}$, $R^{D2}$, $R^{D3}$, and $R^{D4}$ are as defined as corresponding to $R^{B1}$ through $R^{B6}$, e is an integer in the range of 1 to 8 (typically 2 to 4)

f is generally 1 or 2;

T is lower alkylene or alkenylene (generally substituted or unsubstituted methyl or ethyl), $CHR^{G1}$, $C(R^{G1})_2$, O, S, N—$R^{G1}$, P—$R^{G1}$, O=P—$R^{G1}$, Si($R^{G1}$)$_2$, B—$R^{G1}$, or As—$R^{G1}$, where $R^{G1}$ is alkyl, alkenyl, cycloalkyl, cycloalkenyl, aryl, alkaryl, aralkyl, or alkoxy. Furthermore, any of the $R^{D1}$, $R^{D2}$, $R^{D3}$, and $R^{D4}$ moieties can be linked to any of the other $R^{D1}$, $R^{D2}$, $R^{D3}$, and $R^{D4}$ moieties to provide a substituted or unsubstituted alicyclic group containing 4 to 30 ring carbon atoms or a substituted or unsubstituted aryl group containing 6 to 18 ring carbon atoms or combinations thereof and the linkage may include heteroatoms or functional groups, e.g. the linkage may include without limitation an ether, ester, thioether, amino, alkylamino, imino, or anhydride moiety; or (d) a norbornenes represented by the structure (E)

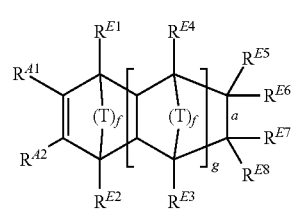

(E)

wherein
$R^{E1}$, $R^{E2}$, $R^{E3}$, $R^{E4}$, $R^{E5}$, $R^{E6}$, $R^{E7}$, and $R^{E8}$ are as defined as corresponding to $R^{B1}$ through $R^{B6}$;

"a" represents a single bond or a double bond;

f is 1 or 2;

g is an integer from 0 to 5, and when "a" is a double bond one of $R^{E5}$, $R^{E6}$ and one of $R^{E7}$, $R^{E8}$ is not present; or (e) a mixture thereof.

Embodiment 29

The photosensitive composition of any one of Embodiments 26 to 28, wherein the organometallic moiety comprises a Group 3 to Group 12 transition metal, preferably Fe, Co, Ni, Ti, Al, Cu, Zn, Ru, Rh, Ag, Ir, Pt, Au, or Hg.

Embodiment 30

The photosensitive composition of any one of Embodiments 26 to 60, wherein the organometallic moiety comprises a catalyst capable of catalyzing metathesis or cross-coupling reactions or splitting water of splitting water.

Embodiment 31

The photosensitive composition of any one of Embodiments 26 to 60, wherein the organometallic moiety is capable of catalyzing the oxidation or reduction of an organic substrate under oxidizing or reducing conditions.
Photosensitive Composition Comprising Pendant Functional Groups, Using any Ru-Carbene Catalyst

Embodiment 32

A photosensitive composition comprising a Fischer-type carbene ruthenium metathesis catalyst admixed or dissolved within a polymerizable material matrix comprising at least one unsaturated organic precursor, each organic having at least one mono-, di, or poly-functionalized cyclic or alicyclic alkene or one alkyne bond;

wherein the ruthenium carbene catalyst can be activated by irradiation by light having at least one wavelength in a range of from about 150 to about 800 nm, preferably in a range of from about 240 to about 260 nm, or from about 260 nm to about 340 nm, or from about 340 to about 360 nm, or a combination thereof, more preferably in a range of from about 240 to about 260 nm or from about 340 to about 360 nm. In particular embodiments, the at least one unsaturated organic precursor comprises a compound having a structure:

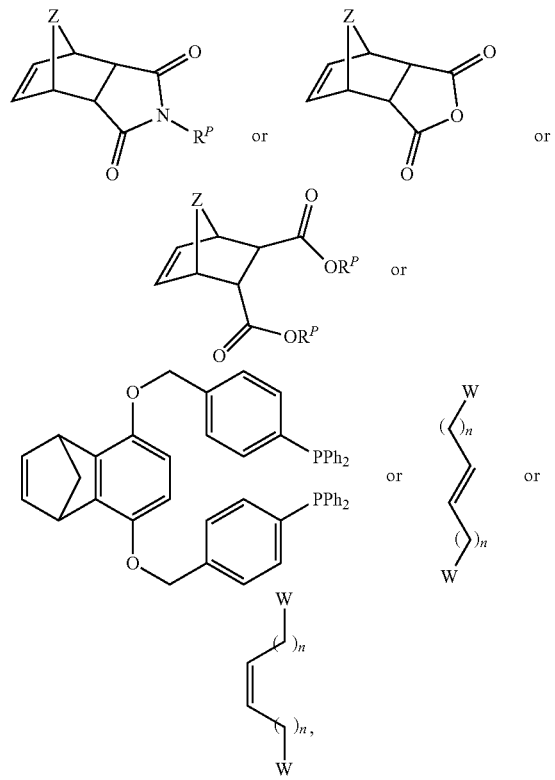

wherein
Z is —O— or $C(R_a)(R_b)$;
$R^P$ is independently H; or $C_{1-6}$ alkyl optionally substituted at the terminus with —N(Ra)($R_b$), —O—$R_a$, —C(O)O—$R_a$, —OC(O)—($C_{1-6}$ alkyl), or —OC(O)—($C_{6-10}$ aryl); or an optionally protected sequence of 3 to 10 amino acids (preferably including R-G-D or arginine-glycine-aspartic acid);

W is independently —N(Ra)($R_b$), —O—$R_a$, or —C(O)O—$R_a$, —P(O)(O$R_a$)$_2$, —SO$_2$(O$R_a$), or SO$_3^-$;

$R_a$ and $R_b$ are independently H or $C_{1-6}$ alkyl;

the $C_{6-10}$ aryl is optionally substituted with 1, 2, 3, 4, or 5 optionally protected hydroxyl groups (the protected hydroxyl groups preferably being benzyl); and n is independently 1, 2, 3, 4, 5, or 6.

Embodiment 33

The composition of Embodiment 32, wherein the at least one unsaturated organic precursor comprising a compound has a structure

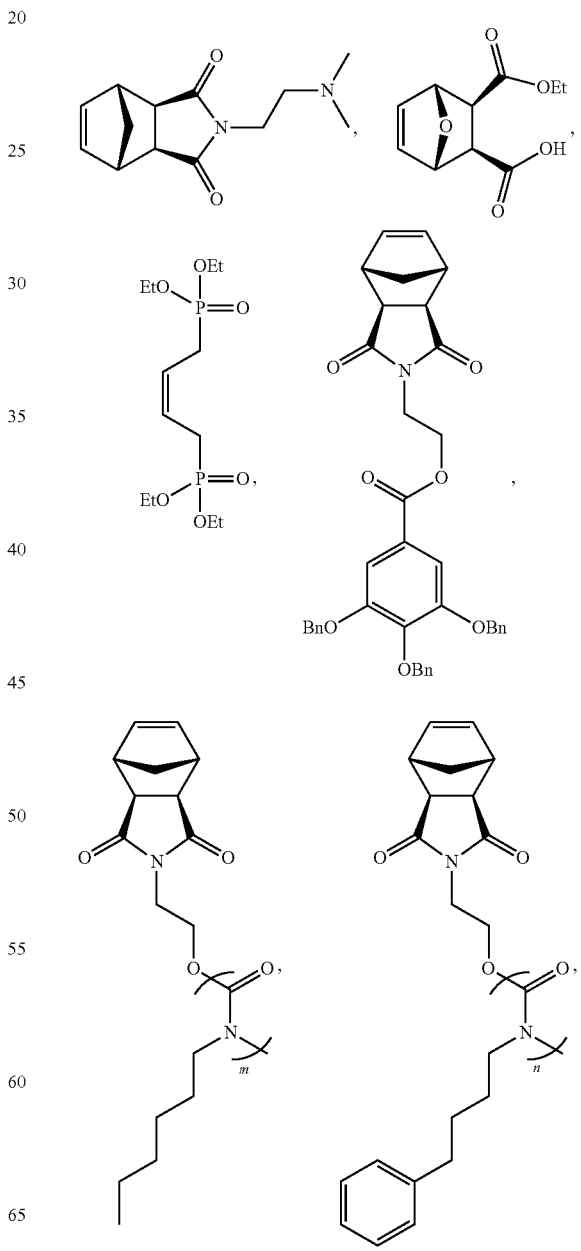

-continued

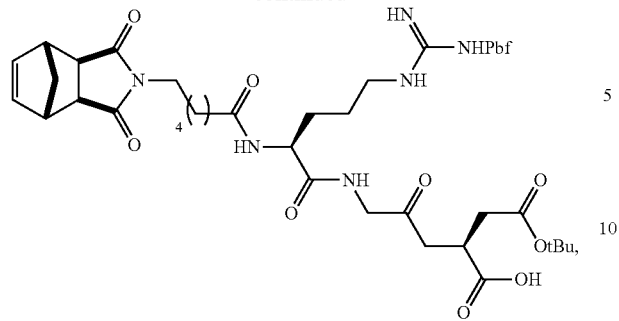

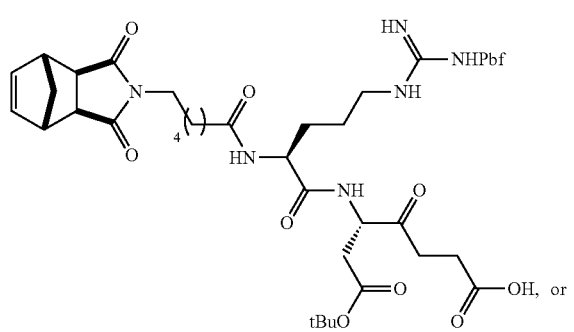

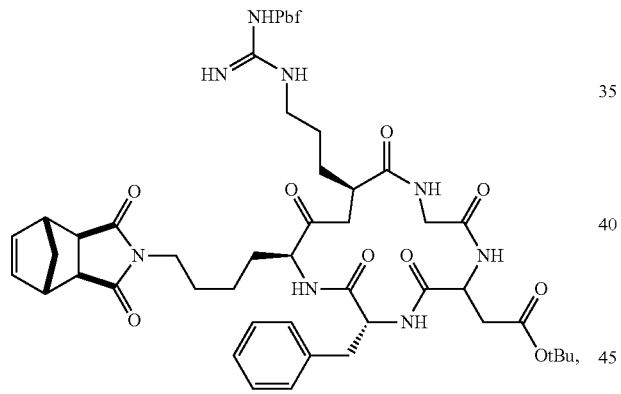

where Bn is benzyl, tBu is tert-butyl, and Pbf is 2,2,4,6,7-pentamethyldihydrobenzofuran.

Embodiment 34

The photosensitive composition of any one of Embodiments 26 to 33, wherein the Fischer-type carbene ruthenium metathesis catalyst is either:

(a) a catalyst generated in situ by the reaction between:
a quenching agent of

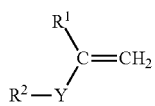

and a metathesis catalyst of Formula (IA), (IB), (IIIA), or (IIIB)

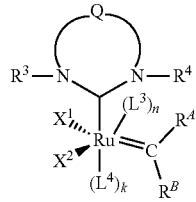
(IA)

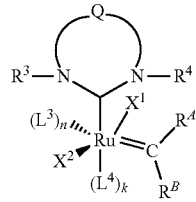
(IB)

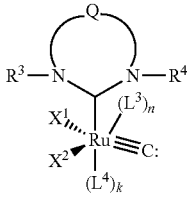
(IIIA)

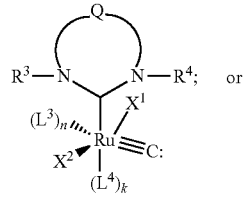
(IIIB)

(b) a catalyst generated in situ by the reaction between

a quenching agent of

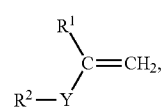

and a metathesis catalyst of Formula (IA), (IB), (IIIA), or (IIIB); or (c) a metathesis catalyst of Formula (II)

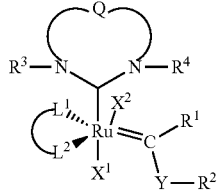
(II)

wherein:

L¹, L², L³, and L⁴ are neutral electron donor ligands;

L¹ and L² are linked by a hydrocarbylene linking group such as an alkylene, substituted alkylene, heteroalkylene, substituted heteroalkene, arylene, substituted arylene, heteroarylene, or substituted heteroarylene linkage, such that when taken together with the Ru to which they are bound or coordinated, form a 5, 6, or 7-membered ring;

k and n are independently 0 or 1;

X¹ and X² are anionic ligands;

Y is O, N—R¹, or S; and

Q is a two-atom linkage having the structure —CR¹¹R¹²—CR¹³R¹⁴— or —CR¹¹=R¹³—, preferably —CR¹¹R¹²—CR¹³R¹⁴—, wherein R¹¹, R¹², R¹³, and R¹⁴ are independently selected from hydrogen, hydrocarbyl, substituted hydrocarbyl, heteroatom-containing hydrocarbyl, substituted heteroatom-containing hydrocarbyl, and functional groups.

R¹, R², $R^A$, and $R^B$ are independently hydrogen, optionally substituted hydrocarbyl, optionally substituted heteroatom-containing hydrocarbyl, functional groups, or may be linked to form a cyclic group, which may be aliphatic or aromatic, and may contain substituents and/or heteroatoms;

R³ and R⁴ are independently optionally substituted hydrocarbyl, or optionally substituted heteroatom-containing hydrocarbyl; and wherein any two or more of X¹, X², L¹, L², L³, R¹, and R² can be taken together to form one or more cyclic groups.

Embodiment 35

The photosensitive composition of any one of Embodiments 26 to 34, wherein the metathesis catalyst is represented by the structure of Formula (II):

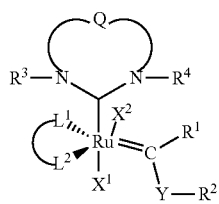

(II)

More specifically, where compound is

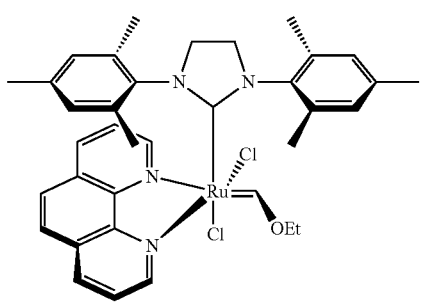

Embodiment 36

The photosensitive composition of any one of Embodiments 26 to 35, wherein the metathesis catalyst is generated in situ by the reaction between:

a quenching agent of

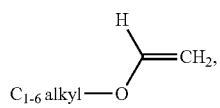

preferably

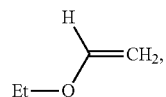

and a metathesis catalyst of structure:

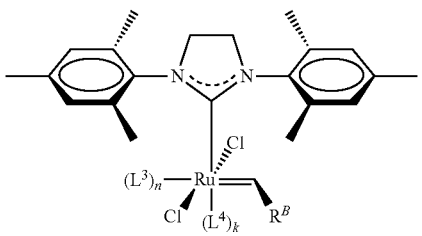

Embodiment 37

The photosensitive composition of any one of Embodiments 26 to 36, wherein the at least one unsaturated organic precursor comprises at least one alkene, alkyne, or both alkene and alkyne moieties and is capable of polymerizing when metathesized.

Embodiment 38

The photosensitive composition of any one of Embodiments 26 to 37, wherein the ruthenium metathesis catalyst is present at a concentration in a range of from about 0.001% to about 5% by weight, relative to the weight of the entire composition.

Embodiment 39

The photosensitive composition of any one of Embodiment 26 to 38, wherein the composition has a viscosity suitable for spin coating, dip coating, or spraying, for example with a viscosity of the composition, at the contemplated temperature of application (preferably ambient room temperature) is in a range of from about 1 cSt to about 10 cSt, from about 10 cSt to about 50 cSt, from about 50 cSt to about 100 cSt, from about 100 cSt to about 250 cSt, from about 250 cSt to about 500 cSt, from about 500 cSt to about 1000 cSt, from about 1000 cSt to about 2000 cSt, from about 2000 cSt to about 5000 cSt, or higher.

Embodiment 40

The photosensitive composition of any one of Embodiments 26 to 38, wherein the composition has a form of a viscous, gelled, semi-solid or solid film.

Methods of Using Photosensitive Composition Comprising Tethered Organometallic, Using any Ru-Carbene Catalyst

Embodiment 41

A method of patterning a polymeric image on a substrate, said method comprising;
(a) depositing at least one layer of a photosensitive composition of any one of Embodiments 26 to 40 on a substrate;
(b) irradiating a portion of the layer of photosensitive composition with a light comprising a wavelength in a range of from about 150 to about 800 nm, preferably in a range of from about 220 to about 440 nm or from about 240 to about 260 nm or from about 340 to about 360 nm, so as to polymerize the irradiated portion of the layer, thereby providing a patterned layer of polymerized and unpolymerized regions.

Embodiment 42

The method of Embodiment 41 comprising depositing a plurality of layers of a photosensitive composition of any one of Embodiments 26 to 40 on a substrate before irradiation.

Embodiment 43

The method of Embodiment 41 or 42, wherein the at least one layer of photosensitive composition is deposited by spin coating, dip coating, or spray coating.

Embodiment 44

The method of Embodiment 41 or 42, wherein photosensitive composition is a gelled, semi-solid or solid film and is deposited by laminating on the substrate.

Embodiment 45

The method of any one of Embodiments 41 to 44, wherein the irradiated portion is patterned by a photomask, by a direct writing application of light, or by interference, nanoimprint, or diffraction gradient lithography.

Embodiment 46

The method of any one of Embodiments 41 to 45, wherein the light has an intensity in a range of about 2 watts to about 6000 watts at least one wavelength in the range of about 150 to about 800 nm, or about from about 220 to about 440 nm.

Embodiment 47

The method of any one of Embodiments 41 to 46, wherein the patterned layer comprises at least one feature having dimensions on the nanometer or micron scale.

Embodiment 48

The method of any one of Embodiments 41 to 47, further comprising removing the unpolymerized region of the pattern.

Polymerized Composition Containing a Tethered Organometallic Moiety

Embodiment 49

A polymerized composition prepared according to any one of Embodiments 41 to 48, or an article of manufacture comprising the polymerize composition.

Embodiment 50

The polymerized composition of Embodiment 49, wherein the composition is a patterned layer.

Embodiment 51

A tissue scaffold comprising a polymerized composition of Embodiment 49 or 50.

Embodiment 52

The tissue scaffold of Embodiment 51, further comprising at least one cell population.

Method of Forming 3-D Structures of Laminated Photosensitive Compositions, Using any Ru-Carbene Catalyst

Embodiment 53

A method comprising;
(a) depositing at least two layers of a composition having at least one alkene or alkyne capable of undergoing a metathesis polymerization or crosslinking reaction, said deposition forming a stacked assembly;
(b) irradiating at least a portion of the stacked assembly with light, such that light penetrates and irradiates at least two layers of the stacked assembly, under conditions sufficient to polymerize or crosslink at least portions of adjacent layers of the stacked assembly;
wherein each layer comprises a Fischer-type carbene ruthenium metathesis catalyst admixed or dissolved therein.

Embodiment 54

The method of Embodiment 53, wherein the Fischer-type carbene ruthenium metathesis catalyst is:
(a) a catalyst generated in situ by the reaction between:
a quenching agent of

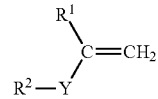

and a metathesis catalyst of Formula (IA), (IB), (IIIA), or (IIIB)

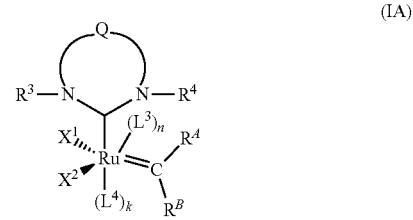

-continued

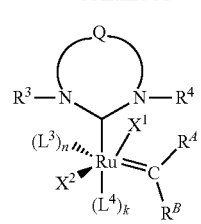 (IB)

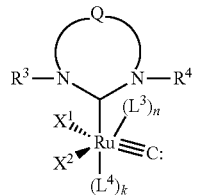 (IIIA)

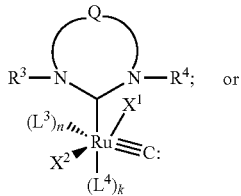 (IIIB)

(b) a catalyst generated in situ by the reaction between

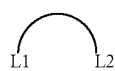

and a metathesis catalyst of Formula (IA), (IB), (IIIA), or (IIIB);

(d) a catalyst generated in situ by the reaction between

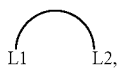

a quenching agent of

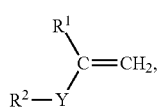

and a metathesis catalyst of Formula (IA), (IB), (IIIA), or (IIIB); or (e) a metathesis catalyst of Formula (II)

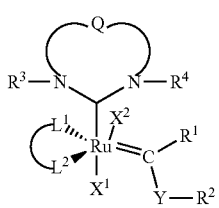 (II)

wherein:
$L^1$, $L^2$, $L^3$, and $L^4$ are independently neutral electron donor ligands;
$L^1$, and $L^2$ are linked by a hydrocarbylene linking group such as an alkylene, substituted alkylene, heteroalkylene, substituted heteroalkene, arylene, substituted arylene, heteroarylene, or substituted heteroarylene linkage, such that when taken together with the Ru to which they are bound or coordinated, form a 5, 6, or 7-membered ring;
k and n are independently 0 or 1;
$X^1$ and $X^2$ are anionic ligands;
Y is O, N—$R^1$, or S; and
Q is a two-atom linkage having the structure —$CR^{11}R^{12}$—$CR^{13}R^{14}$— or —$CR^{11}$=$CR^{13}$—, preferably —$CR^{11}R^{12}$—$CR^{13}R^{14}$—, wherein $R^{11}$, $R^{12}$, $R^{13}$, and $R^{14}$ are independently selected from hydrogen, hydrocarbyl, substituted hydrocarbyl, heteroatom-containing hydrocarbyl, substituted heteroatom-containing hydrocarbyl, and functional groups.
$R^1$, $R^2$, $R^A$, and $R^B$ are independently hydrogen, optionally substituted hydrocarbyl, optionally substituted heteroatom-containing hydrocarbyl, functional groups, or may be linked to form a cyclic group, which may be aliphatic or aromatic, and may contain substituents and/or heteroatoms;
$R^3$ and $R^4$ are independently optionally substituted hydrocarbyl, or optionally substituted heteroatom-containing hydrocarbyl; and
wherein any two or more of $X^1$, $X^2$, $L^1$, $L^2$, $L^3$, $R^1$, and $R^2$ can be taken together to form one or more cyclic groups.

Embodiment 55

The method of Embodiment 53 or 54, wherein the metathesis catalyst is represented by the structure of Formula (II):

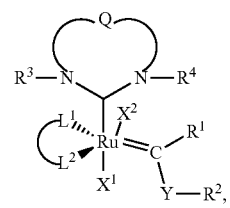 (II)

preferably, where compound is

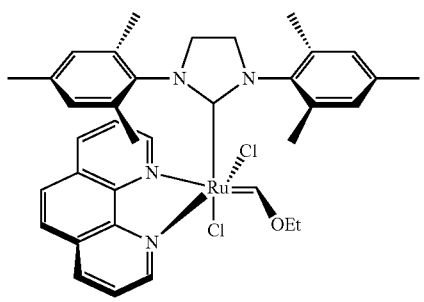

Embodiment 56

The method of Embodiment 53 or 54, wherein the metathesis catalyst is generated in situ by the reaction between a quenching agent of structure:

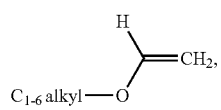

preferably

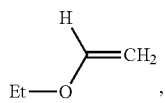

and a metathesis catalyst of structure:

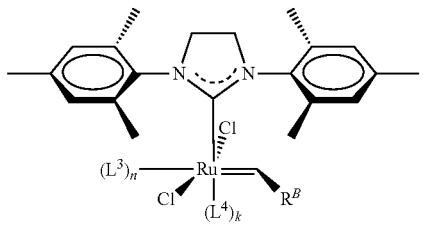

Embodiment 57

The method of any one of Embodiments 53 to 56, wherein the light comprises at least one wavelength in a range of from about 150 to about 800 nm, or from about 150 to about 200 nm or from about 220 to about 240 nm or from about 220 to about 240 nm or from about 240 to about 260 nm or from about 340 to about 360 nm, or a combination thereof.

Embodiment 58

The method of any one of Embodiments 53 to 57, wherein light passes through and irradiates at all layers of the stacked assembly, under conditions sufficient to polymerize or cross-link at least portions of adjacent layers of the stacked assembly.

Embodiment 59

The method of any one of Embodiments 53 to 58, wherein the irradiating is done by patterned exposure of light to the stacked composition, so as to provide a three-dimensional pattern of polymerized and unpolymerized regions through the stacked assembly.

Embodiment 60

The method of Embodiment 59, wherein the irradiation is patterned through use of a photomask, by a direct writing application of light, or by interference, nanoimprint, or diffraction gradient lithography

Embodiment 61

The method of any one of Embodiments 53 to 60, wherein each layer of comprises a pre-formed polymer which may be the same or different from other pre-formed polymer(s) in the other layer(s).

Embodiment 62

The method of any one of Embodiments 53 to 61, wherein the thickness of each layer is independently on the millimeter scale (e.g., from about 1 mm to about 10 mm, from about 10 mm to about 50 mm, from about 50 mm to about 100 mm, from about 100 mm to about 500 mm, from about 500 mm to about 1000 mm, or a combination thereof), the micron scale (e.g., from about 1 micron to about 10 microns, from about 10 microns to about 50 microns, from about 50 microns to about 100 microns, from about 100 microns to about 500 microns, from about 500 microns to about 1000 microns, or a combination thereof), or the nanometer scale (e.g., in a range of from about 50 to about 100 nm, from about 100 to about 200 nm, from about 200 to about 300 nm, from about 300 to about 400 nm, from about 400 to about 500 nm, from about 500 to about 600 nm, from about 600 to about 700 nm, from about 700 to about 800 nm, from about 800 to about 900 nm, from about 900 to about 1000 nm, or a combination thereof.)

Embodiment 63

The method of any one of Embodiments 53 to 62, wherein the polymer in at least one layer is a block copolymer.

Embodiment 64

The method of any one of Embodiments 53 to 63, wherein the polymer is at least one layer of block copolymer, the block copolymer being a dendritic (wedge) or brush (graft, bottlebrush) copolymer.

Embodiment 65

The method of any one of Embodiments 53 to 64, wherein the polymer is at least one layer of block copolymer exhibiting domains having dimensions in a range of from about 5 to about 1500 nanometer domains, or in a range of from about 75 to about 300 nm.

Embodiment 66

The method of any one of Embodiments 53 to 65, wherein the polymer is derived from polymerization of a polymer precursor, and wherein unreacted polymer precursor in the layer provides the at least one alkene or alkyne in the composition.

Embodiment 67

The method of any one of Embodiment 53 to 66, wherein adjacent layers of at least two sequentially deposited layers are compositionally different.

Embodiment 68

The method of any one of Embodiments 53 to 67, wherein adjacent layers of at least two sequentially deposited layers are compositionally the same.

Embodiment 69

A stacked polymer composition prepared according to any one of Embodiments 51 to 68, or an article containing said stacked polymer composition.

Embodiment 70

A photonic structure prepared according to any one of Embodiments 53 to 69.

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

Example 1: Materials and Methods

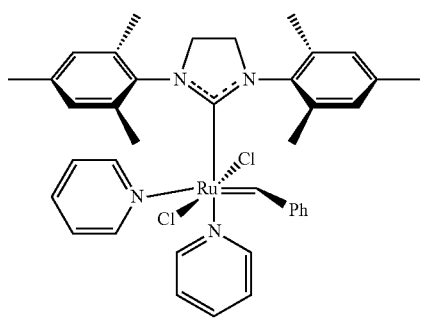

1

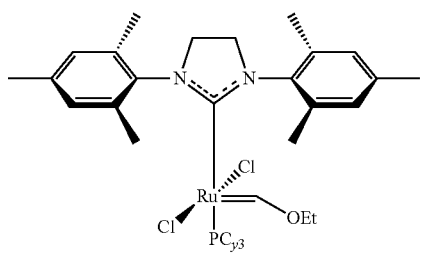

2

($H_2$IMes)(PPh$_3$)(Cl)$_2$RuCHPh was received as a research gift from Materia Inc. and converted to 1 & 2 via literature procedure. (Love, J. A.; Morgan, J. P.; Trnka, T. M.; Grubbs, R. H. *Angew.* 504 *Chem., Int. Ed.* 2002, 41, 4035-4037, Louie, J.; Grubbs, R. H. *Organometallics* 2002, 21, 2153-2164). All other chemicals were purchased from Sigma Aldrich. Printed photomasks were purchased from CAD/Art Services, Inc. (http://outputcity.com). Silicon coupons were ordered as a pre-diced 4" wafer from Ted Pella (Part #16006). Dichloromethane, ethyl vinyl ether and 5-ethylidene-2-norbornene were first degassed by bubbling argon through for 15 minutes. The lamp used was an 8-watt "MRL-58 Multiple Ray Lamp" from Ultra Violet Products (#UVP 95-0313-01). The 254 nm bulb used was a General Electric germicidal bulb (#GEG8T5, from http://bulbtronics.com). The 352 nm bulb was an Eiko blacklight bulb (#WKF8T5BL, from http://bulbtronics.com). Samples were placed approximately 1.5" away from the bulb during exposure.

Profilometry was performed on a Bruker DektakXT stylus profiler. Optical micrographs were obtained on a Zeiss Axio Observer inverted microscope equipped with a 10× objective. NMR spectra were recorded at room temperature on a Varian Inova 500 (at 500 MHz). The NMR spectra were analyzed on MestReNova software and are reported relative to CD2Cl2 (δ=5.320).

Example 2: Photoinitiated Ring-Opening Metathesis Polymerization (ROMP) of 5-ethylidene-2-norbornene (ENBE) and Dicyclopentadiene A 20 mL vial was charged with 1.3 mg solid catalyst 1, and subsequently injected with 1.5 mL 1,5-cyclooctadiene while stirring rapidly. The mixture gelled almost immediately, and was quenched with 3 mL ethyl vinyl ether after ~10 seconds, and sonicated for ~1 hr. This mixture was concentrated en vacuo to a pale yellow solid and subsequently dissolved in 10 mL 5-ethylidene-2-norbornene by stirring and further sonication. This viscous, pale yellow solution was successfully used as a negative photoresist with a UV lamp (UVP, MRL 58, P/N 95-0313-01, 8 watt/115 V~60 Hz/0.16 Amps) at both 254 nm and 352 nm (Hg-arc lamps, USHIO). Films of the pre-exposed resist were made by spin-coating or simply by confining the viscous liquid on a surface. Both shadow masks and printed photomasks (OutputCity) proved successful. As well, the photoresist solution was found to remain active and usable for approximately 3 weeks without any apparent change in color or viscosity, when stored in the dark at room temperature. As well, there was no apparent difference in the fidelity of the resulting patterns over the course of this time period. The resist was developed in hexanes, or in a mixture of dichloromethane and hexanes.

Example 2

In a nitrogen-filled glovebox, two 4 mL vials were each charged with 2.5 mg of complex 2 and 1.0 g of dicyclopentadiene resin 1260B from Materia, Inc. Both vials were removed from the glovebox, one was covered in electrical tape and kept in the dark. The second was placed on its side under a UV lamp (352 nm). The irradiated sample was completely solidified after 45 minutes of irradiation, while the dark sample showed no apparent change in viscosity or color over this same time period.

Example 3: A Representative PLOMP Resist Recipe

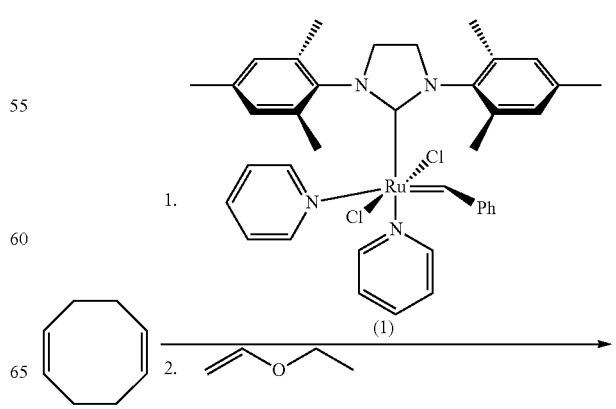

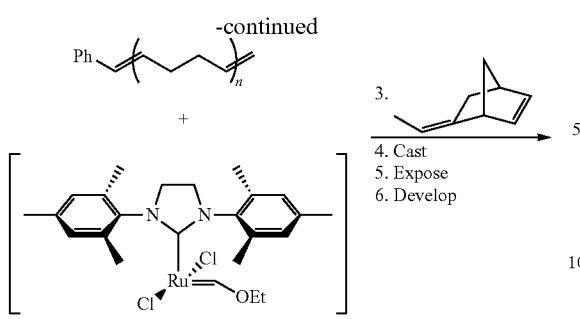

Compound 1 (1.3 mg) was placed under argon and dissolved in 2 mL dichloromethane. To this catalyst solution was quickly added 1.5 mL 1,5-cyclooctadiene, the solution became a semi-solid in 10 seconds and was allowed to react for 1 minute before quenching with 3 mL ethyl vinyl ether. The viscous solution was slowly stirred for 5 minutes, sealed under argon, and sonicated for 1 hour. The volatiles were removed on a rotary evaporator, to yield semisolid poly (COD), colored light yellow by the quenched catalyst (the photoactive vinyl ether complex). Ethylidene norbornene (10 mL) was added to this mixture, which was cooled to 0° C. and sonicated for 1 hour. The partially dissolved mixture was placed on an ice bath and stirred until fully dissolved, while allowing the bath to warm to room temperature. The result is a light yellow, viscous solution weighing approximately 10 grams.

This one-pot preparation from commercially available starting materials can be completed in the span of a few hours. It should be noted that the photoactive vinyl ether complex is sensitive to oxygen, heat and light. Preparation of the resist should be carried out under an inert atmosphere for best results. First, complex 1 is employed to afford the ROMP of 1,5-cyclooctadiene (COD) (Scheme). This reaction was sufficiently complete in minutes, and was subsequently quenched with ethyl vinyl ether. After removing the volatiles in vacuo, the linear poly(COD) was dissolved in a difunctional monomer, such as 5-ethylidene-2-norbornene (ENBE). The chemical composition and molecular weight of the linear polymer, the amount of ENBE and the excess of vinyl ether can all be modulated to tune the properties of the photoresist. The presence of some excess vinyl ether was beneficial for mitigating dark polymerization of the resist material. In these PLOMP resists, the high viscosity of the solution as well as the possibility of dative bonding from the surrounding olefins likely contributed to stabilizing the photocatalyst (FIG. 1). Despite the sensitivity of the ruthenium vinyl ether complexes, the viscous resist solutions could be used successfully under ambient benchtop conditions for many weeks.

Example 4: General Film Casting Procedures

Silicon coupons (1 cm×1 cm) were cleaned in a piranha solution (3:1 concentrated $H_2SO_4$:30% $H_2O_2$), rinsed with copious amounts of deionized water ("Nanopure"), isopropanol and acetone. (Caution Piranha solution reacts violently with organic matter.) Before spin casting, the coupons were heated to 140-150° C. for 1-2 minutes to drive off adventitious moisture, cooled to room temperature under a stream of argon gas, and quickly loaded onto the spinner. While this pre-heating step was not always necessary, it led to the most reproducible results. Approximately 0.1 mL of the resist solution was deposited on each 1 cm² coupon and the samples were spun between 1500-7000 RPM for 60 seconds to achieve films of varying thickness. These cast films should be exposed and developed quickly, prolonged delay after spinning lead to inconsistent results.

Figure 2A:
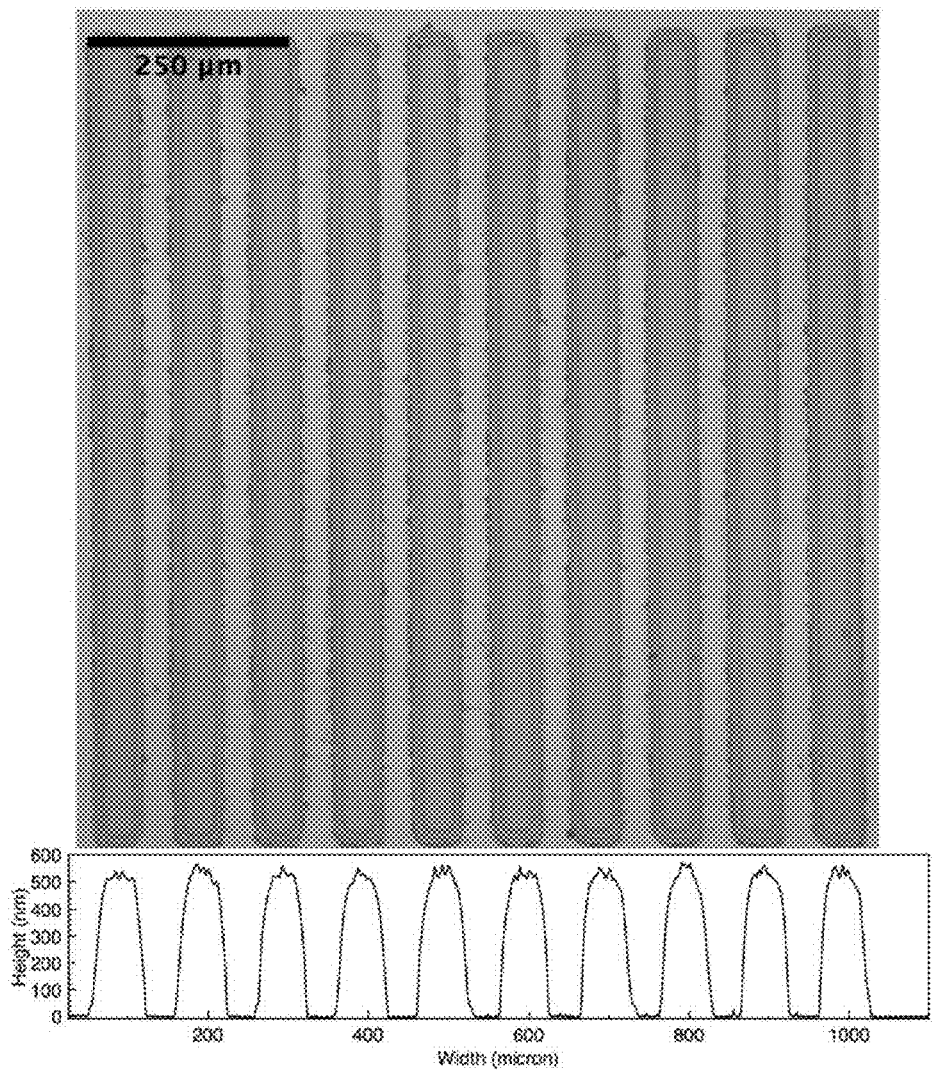
FIG. 2A and FIG. 2B provide micrographs patterns of 1 mm long bars, with widths of 50 microns (FIG. 2A) and 30 microns (FIG. 2B) made by the present invention. The height profiles of the same bar arrays are shown beneath micrograph, as measured by profilometry.
Figure 2B:
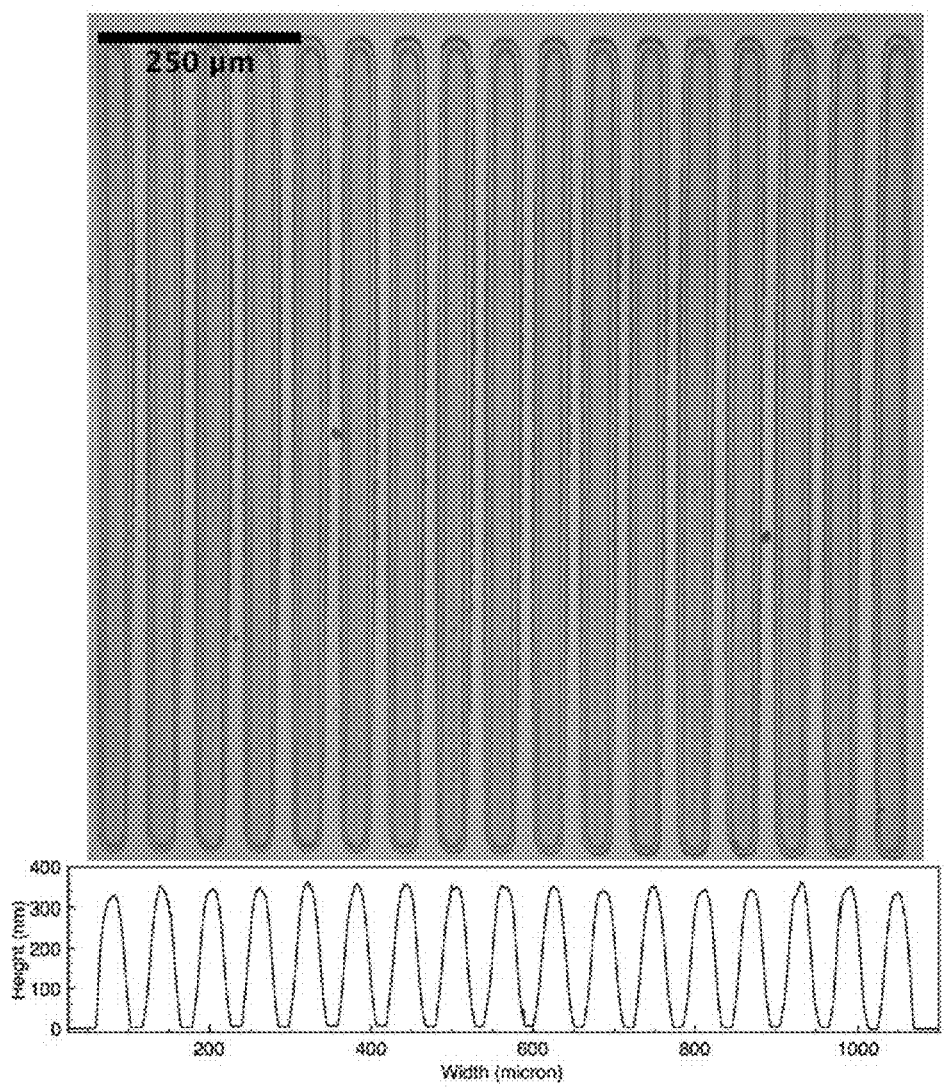

Example 5: Specific Conditions for the Samples in FIG. 2 and FIG. 2B

These compositions proved to be competent UV photoresists, at both 254 nm and 352 nm. The samples in FIG. 3 and FIG. 2B were prepared by using various dilutions of the standard resist preparation outlined above. For FIG. 3, 1.00 mL of the standard resist described above was diluted with 0.1 mL ENBE. Approximately 0.1 mL of this solution was used to cover the 1 cm² coupons, which were spun at 7000 RPM for 60 seconds. The films were irradiated through the grid test mask for 10 minutes, and developed in 10% dichloromethane/hexanes for 2 minutes. For FIG. 2B, 1.25 mL of the standard resist described above was diluted with 0.75 mL ENBE. The wafer was cleaned using the procedure outlined for the coupons, heated to 150° C. for 2 minutes and cooled under a stream of argon. Approximately 1.2 mL of the solution was used to cover the entire wafer, which was spun at 4000 RPM for 60 seconds. The film was irradiated through the Caltech logo mask for 11.5 minutes, and developed in hexanes for 2 minutes.

Example 6: Supplementary Experiments

To show that the catalyst is necessary for the resist to function, the standard resist preparation was used except the polymer was precipitated into methanol to extract the quenched catalyst. Compound 1 (1.3 mg) was placed under argon and dissolved in 2 mL dichloromethane. To this catalyst solution was quickly added 1.5 mL 1,5-cyclooctadiene, the solution became a semi-solid in 10 seconds and was allowed to react for 1 minute before quenching with 3 mL ethyl vinyl ether. The viscous solution was very slowly stirred for 5 minutes, after which 5 mL methanol was added. The suspension was sonicated for 20 minutes, the brown solution was decanted and the off-white solid polymer was washed three times with 10 mL of methanol. The polymer was dried in vacuo, and dissolved in 10 mL 5-ethylidene-2-norbornene to afford a very pale yellow, viscous solution. This solution was cast as before and exposed for 6 minutes at 254 nm (4 times the standard exposure for the analogous resist) with no evidence of pattern formation. After developing with hexanes, a clean Si surface was recovered. Additionally, prolonged irradiation of pure ENBE at both 254 nm and 352 nm did not render any change in viscosity or other evidence of crosslinking. To support the hypothesis that the ruthenium vinyl ether complex was intact inside the PLOMP resist, the ¹H NMR spectra of a PLOMP resist and complex 2 were compared. The resist was prepared by the standard recipe above. The spectra strongly supported the proposed composition of the PLOMP photoresist; the alkylidene protons in each spectrum were less than 1 ppm apart.

Example 7

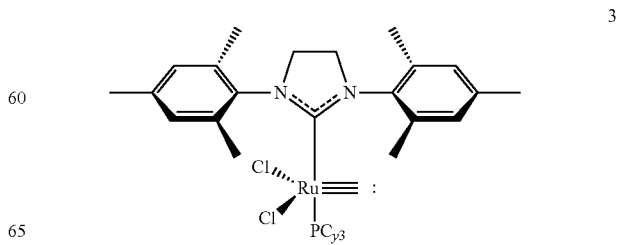

The ruthenium carbide 3 (2.9 mg) was added to a small vial with a magnetic stir bar and dissolved in an inert atmosphere in 100 microliters of methylene chloride. Materia DCPD (dicyclopentadiene) Resin 1260B (1.050 g) was added, and the solution was stirred in the dark for 3 minutes. A 2 cm×2 cm Si coupon with a 290 nm thermal oxide was coated with 0.25 mL of the resulting solution, and spun at 1500 rpm for 30 seconds. The DCPD resin did not wet the substrate well, but a thin film was observed around the edges. Another piece of silicon was used as a mask, placed diagonally across the substrate. The assembly was placed about 1 inch below a UV-C lamp (peak λ≈254 nm) and exposed for 8 minutes. After exposure, the area under the mask remained liquid, while the exposed areas polymerized to a solid film. The unpolymerized DCPD was rinsed gently with acetone to yield a lithographically defined thin film of poly-DCPD.

Example 8

A solution of 95% dicyclopentadiene and 5% ethylidene norbornene (10 mL total, % by volume) was added to a scintillation vial and degassed with argon. The 'Grubbs 2' catalyst shown above (2.1 mg) was dissolved in 100 microliters of degassed chloroform, and this catalyst solution was added to the dicyclopentadiene solution while stirring under argon. At 27.5 minutes, the solution reached the desired viscosity, and the ring-opening metathesis polymerization was quenched by 2.5 mg 1,10-phenanthroline in 0.5 mL ethyl vinyl ether. The solution was stirred for 5 minutes to ensure homogeneous quenching and then stored under argon in the dark overnight before using for photolithography. This 'parent' photoresist could be functionalized with a wide variety of molecules without disrupting the PLOMP patterning process.

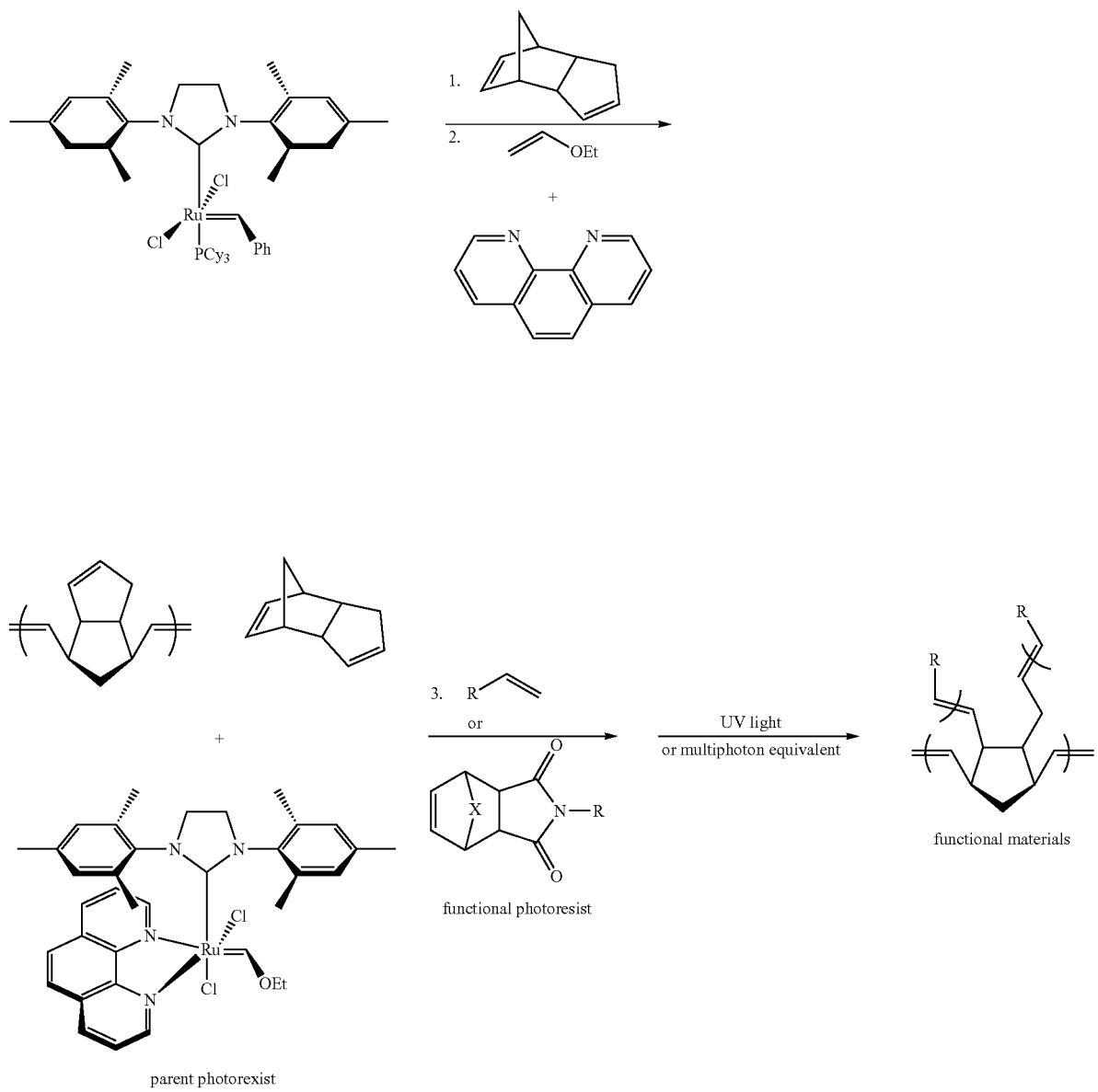

Example 9

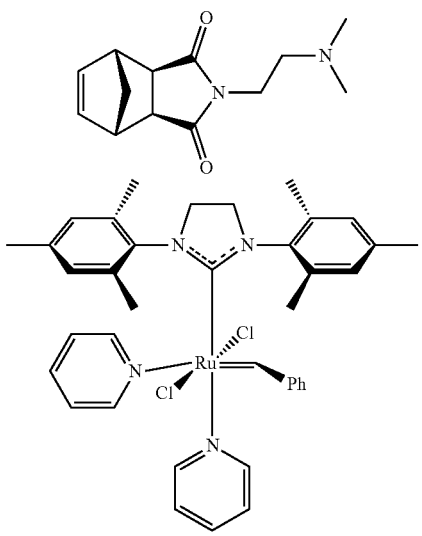

7.5 mg of 4-(2-dimethylamino-ethyl)-4-aza-tricyclo[5.2.1.0$^{2,6}$]dec-ene-3,5-dione was dissolved in 0.1 mL of 5-ethylidene-2-norbornene. This solution was added to 0.1 mL of a resist formulation described above. The resulting solution was spun-cast onto a silicon coupon and irradiated through an array of holes with a 254 nm light source for 2 minutes. After developing the resist in hexanes, the patterned array of holes was observed.

Example 10

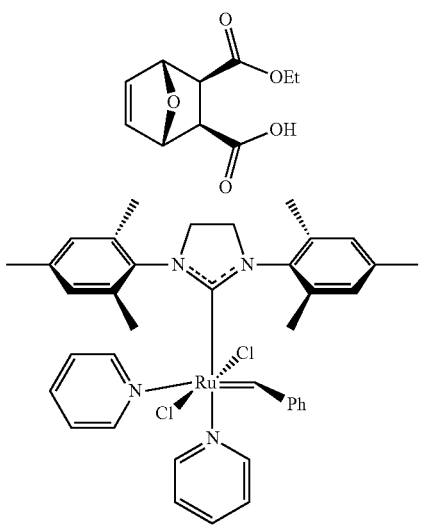

175 mg of 7-oxa-bicyclo[2.2.1]hept-5-ene-2,3-dicarboxylic acid monoethyl ester and 1.3 mL of 1,5-cyclooctadiene were dissolved in 2 mL of dichloromethane, under Ar. 2.5 mg of the "third generation" bispyridine Grubbs-type catalyst (shown above) was dissolved in 1 mL of dichloromethane and added to the monomer solution. After 2 minutes, the viscous reaction mixture was quenched with 1 mL of ethyl vinyl ether. The mixture was concentrated and redissolved in 0.25 mL ethyl vinyl ether and 7 mL of 5-ethylidine-2-norbornene to yield a viscous yellow solution weighing 7.63 grams. This solution was diluted with 0.4 mL 5-ethylidine-2-norbornene, spun cast, and irradiated through an array of holes with a 254 nm light source for 1.5 minutes. After developing the resist with 10% dichloromethane in hexanes, the pattern was observed.

Example 11

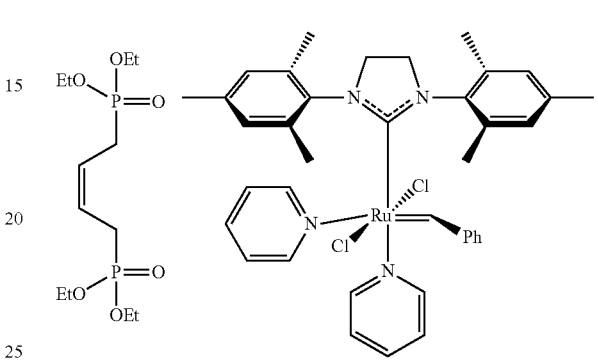

0.21 grams of the diphosphonate chain transfer agent shown above as dissolved in 1.5 mL of 1,5-cyclooctadiene under argon. 1.3 mg of the "third generation" bispyridine Grubbs-type catalyst (shown above) was dissolved in 3 mL dichloromethane and added to the monomer solution. After 2 minutes, the viscous reaction mixture was quenched with 3 mL of ethyl vinyl ether. The mixture was concentrated and redissolved in 1 mL ethyl vinyl ether and 5 mL of 5-ethylidene-2-norbornene to yield a viscous yellow solution. This solution was spun cast onto a silicon substrate and irradiated through an array of hoes with a 254 nm light source for 4 minutes. The exposed sample was heated to 50° C. for 1 minute. After developing the resist in hexanes, the pattern was observed.

Example 12: Peptide Example

A norbornene monomer functionalized with a short, protected amino acid sequence: R-G-D (arginine-glycine-aspartic acid) was added to a batch of PLOMP photoresist prepared by a procedure of Example 3. A patterned, peptide-functionalize surface was generated by spin casting this mixture onto a silicon chip, irradiating the film with a germicidal UV lamp (~250 nm light) through a mask for 2 minutes, and developing the resist in 10% dichloromethane in hexanes.

Example 13

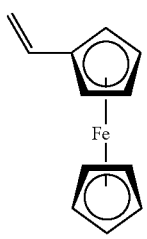

The procedure of Example 11 was repeated, with the ferrocene derivative shown above replacing the diphosphonate chain transfer agent. After developing the resist in hexanes, the pattern was observed.

Example 14

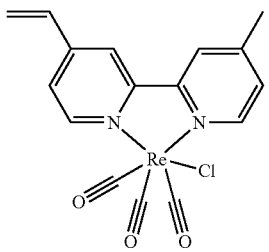

To a small vial was added 3.0 mg of the above rhenium complex, dissolved in 1.5 mL acetonitrile. A 100 microliter aliquot of this solution was added to 1 mL 5-ethylidene-2-norbornene, along with 100 microliters of the PLOMP photoresist. A thin film was formed on a glassy carbon electrode by spin-coating, and irradiated for 2 minutes at ~250 nanometers with a germicidal UV bulb. Crosslinking of the film was confirmed by insolubility in organic solvents.

Example 15: Hierarchical Assembly Example

A hierarchically-patterned structure was generated by adding a dendritic "wedge-type" block copolymer, as described in Piunova, et al., J. Amer. Chem. Soc, 2013, 135 (41), pp 15609-15616 to a PLOMP photoresist of Example 3, spin casting the film onto a silicon surface, irradiating with UV light (~250 nm) through a mask, and developing in a mixture of dichloromethane and hexanes.

Example 16: Nanoimprint Lithography (See FIG. 5)

Nanopatterned PDMS stamps were fabricated using the method published by Verschuuren, M. A. "Substrate Conformal Imprint Lithography for Nanophotonics". Ph.D. Thesis, University Utrecht, The Netherlands, 2010. The PLOMP photoresist was prepared as above, the viscosity was adjusted as necessary to access various film thicknesses by diluting with ethylidene norbornene. Thin films of the resist were cast onto silicon chips (1×1 cm) using a spin-coater. The nanopatterned side of the PDMS stamp was brought into contact with the PLOMP resist, and the two sides were compressed together using binder clips. The films were exposed using a blacklight (~360 nm) UV lamp, which illuminated the resist by transmitting through the PDMS stamp, for 20-30 minutes. After curing, the stamp was peeled away, leaving a nanopatterned crosslink polymer film on the surface.

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes.

What is claimed:

1. A photosensitive composition comprising a ruthenium carbene metathesis catalyst of Formula (II):

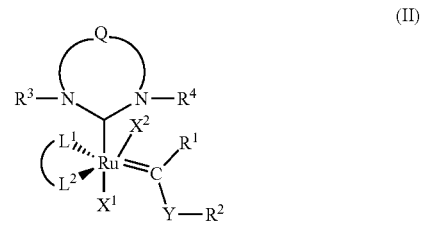

(II)

admixed within a polymerizable material matrix comprising at least one unsaturated organic precursor;
wherein

is an aromatic bidentate diamine ligand coordinated to Ru, which, when taken together with the Ru to which it is coordinated, forms a 5, 6, or 7-membered ring;
$X^1$ and $X^2$ are independent anionic ligands;
Y is O, N-R', or S; and
Q is a two-atom linkage having the structure -$CR^{11}R^{12}$-$_{CR}$$^{13}R^{14}$- or -$CR^{11}$=$CR^{13}$-, wherein $R^{11}$, $R^{12}$, $R^{13}$, and $R^{14}$ are independently hydrogen, hydrocarbyl, substituted hydrocarbyl, heteroatom-containing hydrocarbyl, or substituted heteroatom-containing hydrocarbyl;
$R^1$ and $R^2$ are independently hydrogen, optionally substituted hydrocarbyl, optionally substituted heteroatom-containing hydrocarbyl, or may be linked to form a cyclic group, which may be aliphatic or aromatic, and may contain substituents and/or heteroatoms; and
$R^3$ and $R^4$ are independently optionally substituted hydrocarbyl or optionally substituted heteroatom-containing hydrocarbyl and may contain substituents and/or heteroatoms.

2. The photosensitive composition of claim 1, wherein $R^2$ is $C_{1-6}$ alkyl.

3. The photosensitive composition of claim 1, wherein Q is —$CH_2$-$CH_2$— and either $R^3$ or $R^4$, or both $R^3$ and $R^4$ are phenyl groups, optionally substituted in the 2, 6 positions with independent $C_{1-6}$ alkyl groups.

4. The photosensitive composition of claim 1, wherein Q is —$CH_2$-$CH_2$— and $R^3$ and $R^4$ are independently mesityl or optionally substituted adamantyl.

5. The photosensitive composition of claim 1, wherein

is a phenanthroline, optionally substituted with at least one electron-withdrawing or electron-donating group.

6. The photosensitive composition of claim 5, where the ruthenium carbene metathesis catalyst is represented by a structure:

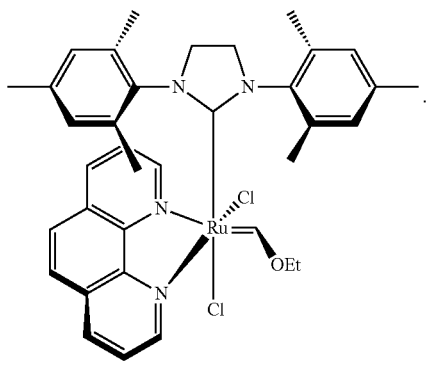

7. The photosensitive composition of claim 1, wherein the ruthenium carbene metathesis catalyst, upon activation by irradiation of light of at least one wavelength in a range of from about 150 nm to about 800 nm can crosslink or polymerize at least one of the unsaturated organic precursor.

8. The photosensitive composition of claim 1, wherein the unsaturated organic precursor comprises a mono-unsaturated cyclic olefin; a monocyclic diene; or a bicyclic or polycyclic olefin.

9. The photosensitive composition of claim 8, herein the unsaturated organic precursor comprises a compound having a structure:

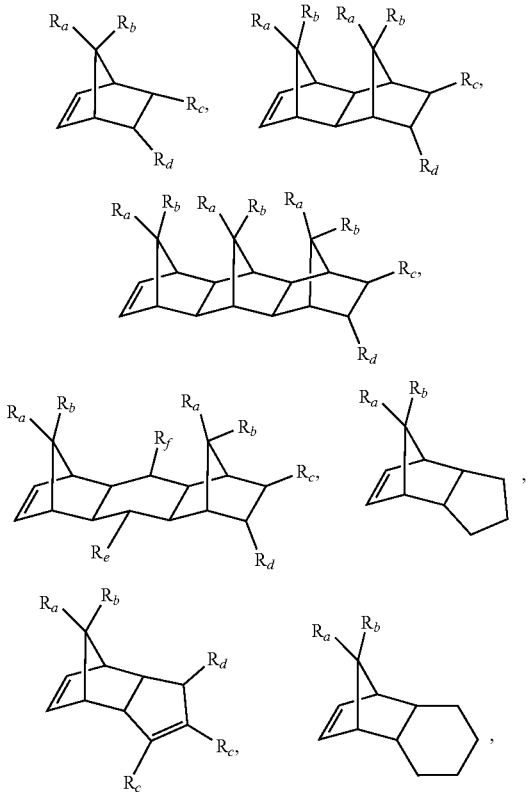

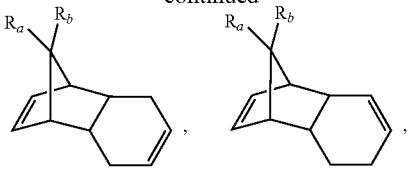

or a mixture thereof, wherein $R_a$, $R_b$, $R_c$, $R_d$, $R_e$, and $R_f$ are independently H or $C_{1-20}$ alkyl.

10. A method of patterning a polymeric image on a substrate, said method comprising;
(a) depositing a layer of a photosensitive composition of claim 1 on a substrate;
(b) irradiating a portion of the layer of photosensitive composition with a light comprising at least one wavelength in a range of from about 150 to about 800 nm, so as to polymerize the irradiated portion of the layer, thereby providing polymerized and unpolymerized regions in the layer.

11. The method of claim 10, wherein the photosensitive composition is deposited by spin coating, dip coating, or spray coating or wherein photosensitive composition is a gelled, semi-solid or solid film and is deposited by laminating on the substrate.

12. The method of claim 10, wherein the irradiated portion is patterned through use of a photomask, by a direct writing application of light, or by interference or diffraction gradient lithography.

13. The method of claim 10, further comprising removing the unpolymerized region of the pattern.

14. A patterned polymer layer prepared according to claim 12, or an article containing said patterned polymer layer.

15. The polymer layer of claim 14, the polymer layer being resistant to aqueous HF, said patterned polymer being able to withstand exposure to aqueous HF at room temperatures for a period of 1 hour without measurable peeling from the substrate.

16. A photosensitive composition of claim 1 wherein the polymerizable material matrix comprises at least one unsaturated organic precursor and at least one different unsaturated precursor comprising a tethered organometallic catalyst, each unsaturated organic and tethered precursor having at least one alkene or one alkyne bond, wherein the ruthenium carbene metathesis catalyst can be activated by irradiation by light having at least one wavelength in a range of from about 150 to about 800 nm.

17. The photosensitive composition of claim 16, wherein the at least one unsaturated organic precursor is a ROMP (Ring-Opening Metathesis Polymerization) precursor.

18. The photosensitive composition of claim 16, wherein the organometallic catalyst comprises a Group 3 to Group 12 transition metal, preferably Fe, Co, Ni, Ti, Al, Cu, Zn, Ru, Rh, Ag, Ir, Pt, Au, or Hg.

19. The photosensitive composition of claim 18, wherein the tethered organometallic catalyst is capable of catalyzing metathesis or cross-coupling reactions or splitting water.

20. The photosensitive composition of claim 18, wherein the organometallic catalyst is capable of catalyzing the oxidation or reduction of an organic substrate under oxidizing or reducing conditions.

21. A photosensitive composition comprising a Fischer-type carbene ruthenium metathesis catalyst admixed or dissolved within a polymerizable material matrix comprising at least one unsaturated organic precursor, each organic having at least one alkene or one alkyne bond;

wherein the Fischer-type carbene ruthenium metathesis catalyst can be activated by irradiation by light having at least one wavelength in a range of from about 150 to about 800 nm;

said at least one unsaturated organic precursor comprising a compound having a structure:

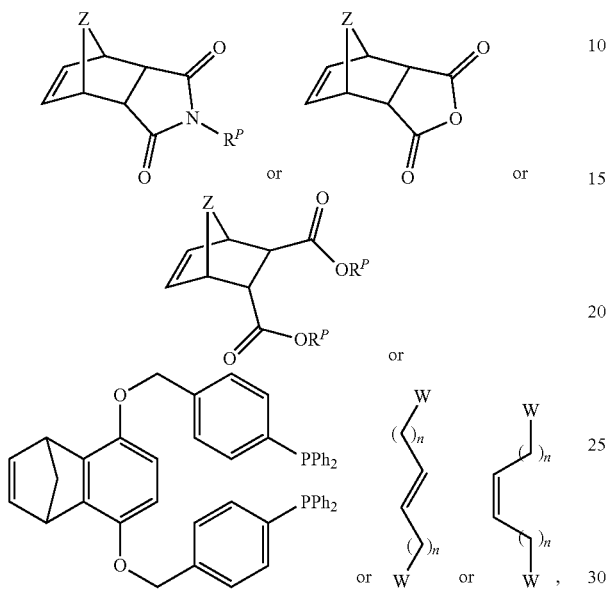

wherein
Z is —O— or $C(R_a)(R_b)$;
$R^P$ is independently H; or $C_{1-6}$ alkyl optionally substituted at the terminus with $-N(R_a)(R_b)$, $-O-R_a$, $-C(O)O-R_a$, $-OC(O)-(C_{1-6}$ alkyl), or $-OC(O)-(C_{6-10}$ aryl); or an optionally protected sequence of 3 to 10 amino acids;
W is independently $-N(R_a)(R_b)$, $-O-R_a$, or $-C(O)O-R_a$, $-P(O)(OR_a)_2$, $-SO_2(OR_a)$, or $SO_3"$;
$R_a$ and $R_b$ are independently H or $C_{1-6}$ alkyl;
the $C_{6-10}$ aryl is optionally substituted with 1, 2, 3, 4, or 5 optionally protected hydroxyl groups; and
n is independently 1, 2, 3, 4, 5, or 6;
wherein the Fischer-type carbene ruthenium metathesis catalyst is:
a metathesis catalyst of Formula (II), optionally generated in situ:

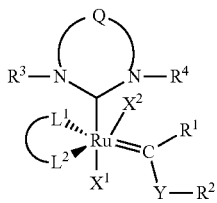

(II)

wherein:

$L^1$ and $L^2$ is an aromatic bidentate diamine ligand coordinated to Ru, which when taken-together with the Ru to which it is-coordinated, forms a 5, 6, or 7-membered ring;
$X^1$ and $X^2$ are anionic ligands;
Y is O, $N-R^1$, or S; and
Q is a two-atom linkage having the structure $-CR^{11}R^{12}-CR^{13}R^{14}-$ or $-CR^{11}=CR^{13}-$, wherein $R^{11}$, $R^{12}$, $R^{13}$, and $R^{14}$ are independently selected from hydrogen, hydrocarbyl, substituted hydrocarbyl, heteroatom-containing hydrocarbyl, and substituted heteroatom-containing hydrocarbyl;
$R^1$ and $R^2$ are independently hydrogen, optionally substituted hydrocarbyl, optionally substituted heteroatom-containing hydrocarbyl, functional groups, or may be linked to form a cyclic group, which may be aliphatic or aromatic, and may contain substituents and/or heteroatoms;
$R^3$ and $R^4$ are independently optionally substituted hydrocarbyl or optionally substituted heteroatom-containing hydrocarbyl; and
wherein any two or more $X^1$, $X^2$, $L^1$, $L^2$, $R^1$, and $R^2$ can be taken together to form one or more cyclic groups.

22. The photosensitive composition of claim 21, wherein the metathesis catalyst is represented by the structure:

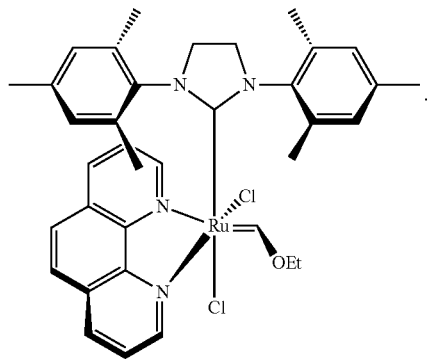

23. A method of patterning a polymeric image on a substrate, said method comprising;
(a) depositing at least one layer of a photosensitive composition of claim 21 on a substrate;
(b) irradiating a portion of the layer of photosensitive composition with a light comprising a wavelength in a range of from about 150 to about 800 nm, so as to polymerize the irradiated portion of the layer, thereby providing a patterned layer of polymerized and unpolymerized regions.

24. The method of claim 23, wherein the irradiated portion is patterned by a photomask, by a direct writing application of light, or by interference or diffraction gradient lithography.

25. The method of claim 23, further comprising removing the unpolymerized region of the pattern.

26. A polymerized composition prepared according to claim 23, or an article of manufacture comprising the polymerize composition.

27. The polymerized composition of claim 26, wherein the composition is a patterned layer.

28. A tissue scaffold comprising a polymerized composition of claim 26.

29. The tissue scaffold of claim 28, further comprising at least one cell population.

30. A method comprising;
(a) depositing at least two layers of a composition having at least one alkene or alkyne capable of undergoing a metathesis polymerization or crosslinking reaction, said deposition forming a stacked assembly;
(b) irradiating at least a portion of the stacked assembly with light, such that light penetrates and irradiates at least two layers of the stacked assembly, under conditions sufficient to polymerize or crosslink at least portions of adjacent layers of the stacked assembly, such that at least portions of adjacent layers to polymerize or crosslink;
wherein each layer comprises a Fischer-type carbene ruthenium metathesis catalyst admixed or dissolved therein, the Fischer-type carbene ruthenium metathesis catalyst comprising a non-persistent ruthenium carbene moiety of structure:

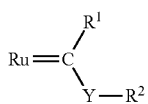

wherein the Fischer-type carbene ruthenium metathesis catalyst is:
a metathesis catalyst of Formula (II), optionally generated in situ:

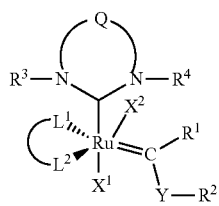

(II)

wherein:

$L^1$ and $L^2$ is an aromatic bidentate diamine ligand coordinated to Ru, which when taken together with the Ru to which it is coordinated, forms a 5, 6, or 7-membered ring;
$X^1$ and $X^2$ are anionic ligands;
Y is O, N-$R^1$, or S; and
Q is a two-atom linkage having the structure -$CR^{11}R^{12}$-$CR^{13}R^{14}$- or -$CR^{11}$=$CR^{13}$-,, wherein $R^{11}$, $R^{12}$, $R^{13}$, and $R^{14}$ are independently hydrogen, hydrocarbyl, substituted hydrocarbyl, heteroatom-containing hydrocarbyl, or substituted heteroatom-containing hydrocarbyl;
$R^1$ and $R^2$ are independently hydrogen, optionally substituted hydrocarbyl, optionally substituted heteroatom-containing hydrocarbyl, or may be linked to form a cyclic group, which may be aliphatic or aromatic and may contain substituents and/or heteroatoms;
$R^3$ and $R^4$ are independently optionally substituted hydrocarbyl, or optionally substituted heteroatom-containing hydrocarbyl; and
wherein any two or more of $X^1$, $X^2$, $L^1$, $L^2$, $R^1$, and $R^2$ can be taken together to form one or more cyclic groups.

31. The method of claim 30, wherein the metathesis catalyst is represented by the structure of:

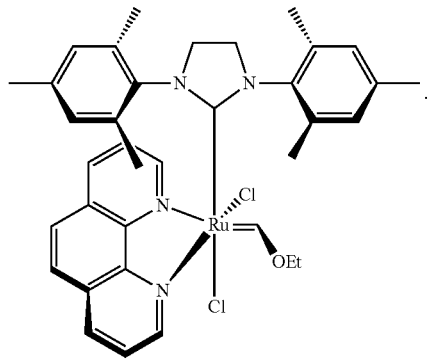

32. The method of claim 30, wherein light passes through and irradiates at all layers of the stacked assembly, under conditions sufficient to polymerize or crosslink at least portions of adjacent layers of the stacked assembly, such that at least portions of adjacent layers of the stacked assembly are polymerized or crosslinked.
33. The method of claim 30, wherein the irradiating is done by patterned exposure of light to the stacked composition, so as to provide a three-dimensional pattern of polymerized and unpolymerized regions through the stacked assembly.
34. The method of claim 30, wherein the irradiation is patterned through use of a photomask, by a direct writing application of light, or by interference or diffraction gradient lithography.
35. The method of claim 30, wherein the polymer in at least one layer is a block copolymer.
36. The method of claim 35, wherein the block copolymer is a dendritic (wedge) or brush (graft, bottlebrush) copolymer.
37. The method of claim 30, wherein the thickness of each layer is independently in a range of from about 50 nm to about 50 mm.
38. The method of claim 30, wherein adjacent layers of at least two sequentially deposited layers are compositionally different.
39. A stacked polymer composition prepared according to claim 30, or an article containing said stacked polymer composition.
40. A photonic structure comprising a stacked polymer composition of claim 39.
41. The photosensitive composition of claim 1, wherein

is a phenanthroline or bipyridine.
42. The photosensitive composition of claim 1, wherein:

is a phenanthroline or bipyridine;
$X^1$ and $X^2$ are chloro;
Y is O;
Q is a two-atom linkage having the structure -$CR^{11}R^{12}$-$CR^{13}R^{14}$- or -$CR^{11}$=$CR^{13}$-,, wherein $R^{11}$, $R^{12}$, $R^{13}$, and $R^{14}$ are independently hydrogen, $C_{1-6}$ alkyl, or phenyl;

$R^1$ is hydrogen and $R^2$ is $C_{1-6}$ alkyl; and $R^3$ and $R^4$ are independently adamantly or phenyl groups, optionally substituted in the 2,4, and 6 positions with independent $C_{1-6}$ alkyl groups; and wherein the unsaturated organic precursor comprises a mono-unsaturated cyclic olefin; a monocyclic diene; or a bicyclic or polycyclic olefin.

43. The photosensitive composition of claim 21, wherein

is a phenanthroline or bipyridine.

44. The photosensitive composition of claim 21, wherein:

a phenanthroline or bipyridine;

$X^1$ and $X^2$ are chloro;

Y is O;

Q is a two-atom linkage having the structure $-CR^{11}R^{12}-CR^{13}R^{14}-$ or $-CR^{11}\!\!=\!\!CR^{13}-$, wherein $R^{11}$, $R^{12}$, $R^{13}$, and $R^{14}$ are independently hydrogen, $C_{1-6}$ alkyl, or phenyl;

$R^1$ is hydrogen and $R^2$ is $C_{1-6}$ alkyl; and $R^3$ and $R^4$ are independently adamantly or phenyl groups, optionally substituted in the 2,4, and 6 positions with independent $C_{1-6}$ alkyl groups.

45. The method of claim 30, wherein

is a phenanthroline or bipyridine.

46. The method of claim 30, wherein:

is a phenanthroline or bipyridine;

$X^1$ and $X^2$ are chloro;

Y is O;

Q is a two-atom linkage having the structure $-CR^{11}R^{12}-CR^{13}R^{14}-$ or $-CR^{11}\!\!=\!\!CR^{13}-$, wherein $R^{11}$, $R^{12}$, $R^{13}$, and $R^{14}$ are independently hydrogen, $C_{1-6}$ alkyl, or phenyl;

$R^1$ is hydrogen and $R^2$ is $C_{1-6}$ alkyl; and $R^3$ and $R^4$ are independently adamantly or phenyl groups, optionally substituted in the 2,4, and 6 positions with independent $C_{1-6}$ alkyl groups.

47. The photosensitive composition of claim 1, wherein

is a bipyridine.

48. The photosensitive composition of claim 47, wherein the compound of Formula (II) is represented by a structure (IIA) or (IIB):

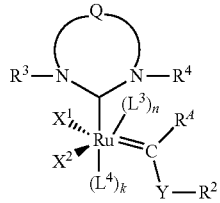

(IIA)

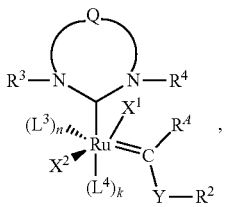

(IIB)

wherein $R^A$ is $R^1$; and $(L^3)_n$ and $(L^4)_k$ together is a bipyridine.

49. The photosensitive composition of claim 1, wherein:

is a bipyridine;

$X^1$ and $X^2$ are chloro;

Y is O;

Q is a two-atom linkage having the structure $-CR^{11}R^{12}-CR^{13}R^{14}-$ or $-CR^{11}\!\!=\!\!CR^{13}-$, wherein $R^{11}$, $R^{12}$, $R^{13}$, and $R^{14}$ are independently hydrogen, $C_{1-6}$ alkyl, or phenyl;

$R^1$ is hydrogen and $R^2$ is $C_{1-6}$ alkyl; and $R^3$ and $R^4$ are independently adamantly or phenyl groups, optionally substituted in the 2,4, and 6 positions with independent $C_{1-6}$ alkyl groups; and wherein the unsaturated organic precursor comprises a mono-unsaturated cyclic olefin; a monocyclic diene; or a bicyclic or polycyclic olefin.

50. The photosensitive composition of claim 49, wherein the compound of Formula (II) is represented by a structure (IIA) or (IIB):

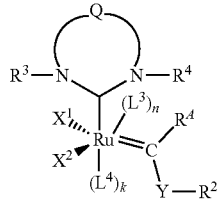

(IIA)

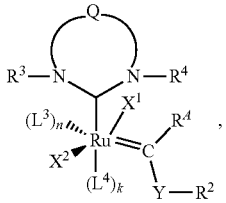

(IIB)

wherein $R^A$ is $R^1$; and $(L^3)_n$ and $(L^4)_k$ together is a bipyridine.

51. The photosensitive composition of claim 21, wherein

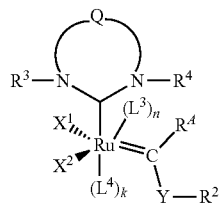

is a bipyridine.

52. The photosensitive composition of claim 51, wherein the compound of Formula (II) is represented by a structure (IIA) or (IIB):

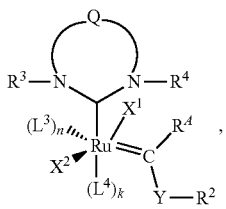

(IIA)

(IIB)

wherein $R^A$ is $R^1$; and
$(L^3)_n$ and $(L^4)_k$ together is a bipyridine.

53. The photosensitive composition of claim 21, wherein:

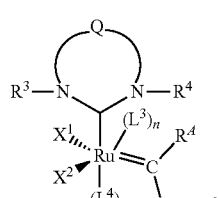

is a bipyridine;
$X^1$ and $X^2$ are chloro;
Y is O;
Q is a two-atom linkage having the structure -CR$^{11}$R$^{12}$-CR$^{13}$R$^{14}$- or -CR$^{11}$=CR$^{13}$-, wherein R$^{11}$, R$^{12}$, R$^{13}$, and R$^{14}$ are independently hydrogen, C$_{1-6}$ alkyl, or phenyl;
$R^1$ is hydrogen and $R^2$ is C$_{1-6}$ alkyl; and
$R^3$ and $R^4$ are independently adamantly or phenyl groups, optionally substituted in the 2,4, and 6 positions with independent C$_{1-6}$ alkyl groups.

54. The photosensitive composition of claim 53, wherein the compound of Formula (II) is represented by a structure (IIA) or (IIB):

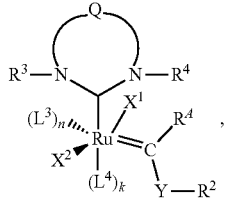

(IIA)

(IIB)

wherein $R^A$ is $R^1$; and
$(L^3)_n$ and $(L^4)_k$ together is a bipyridine.

55. The method of claim 30, wherein

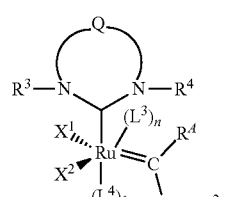

is a bipyridine.

56. The photosensitive composition of claim 55, wherein the compound of Formula (II) is represented by a structure (IIA) or (IIB):

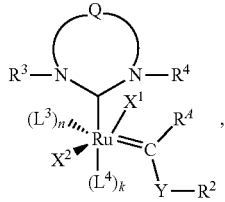

(IIA)

(IIB)

wherein $R^A$ is $R^1$; and
$(L^3)_n$ and $(L^4)_k$ together is a bipyridine.

57. The method of claim 30, wherein:

is a bipyridine;
$X^1$ and $X^2$ are chloro;
Y is O;
Q is a two-atom linkage having the structure -CR$^{11}$R$^{12}$-CR$^{13}$R$^{14}$- or -CR$^{11}$=CR$^{13}$-, wherein R$^{11}$, R$^{12}$, R$^{13}$, and R$^{14}$ are independently hydrogen, C$_{1-6}$ alkyl, or phenyl;
$R^1$ is hydrogen and $R^2$ is C$_{1-6}$ alkyl; and
$R^3$ and $R^4$ are independently adamantly or phenyl groups, optionally substituted in the 2,4, and 6 positions with independent C$_{1-6}$ alkyl groups.

58. The photosensitive composition of claim 57, wherein the compound of Formula (II) is represented by a structure of Formula (IIA) or (IIB):

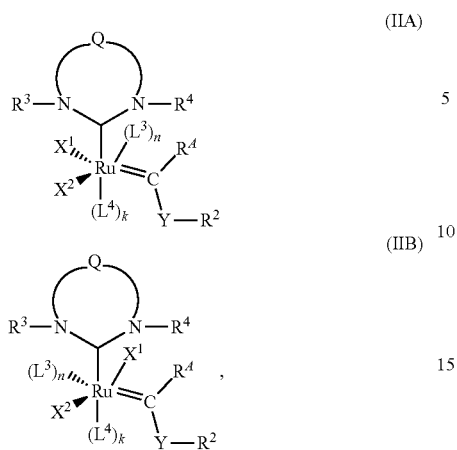
(IIA)
(IIB)
wherein $R^A$ is $R^1$; and
$(L^3)_n$ and $(L^4)_k$ together is a bipyridine.
\* \* \* \* \*